United States Patent [19]
Levens et al.

[11] Patent Number: 5,580,760
[45] Date of Patent: Dec. 3, 1996

[54] FUSE BINDING PROTEIN AND CDNA THEREFOR

[75] Inventors: David L. Levens, Bethesda; Robert C. Duncan, Mt. Rainer; Mark I. Avigan, Silver Spring, all of Md.

[73] Assignee: The United States of America as represented by the Department of Health and Human Services, Washington, D.C.

[21] Appl. No.: 21,608

[22] Filed: Feb. 22, 1993

[51] Int. Cl.$^6$ .......................... C12P 19/34; C07H 21/04; C12N 5/10; C12N 15/63
[52] U.S. Cl. .................... 435/91.2; 536/23.1; 536/24.31; 435/240.2; 435/252.3; 435/320.1
[58] Field of Search ........................ 435/320.1, 6, 240.2, 435/252.3, 91.2; 536/23.1, 23.5, 24.31, 24.33

[56] References Cited
PUBLICATIONS

Sigma Molecular Biology 1989; pp. 51 and 52; Published by Sigma Chemical Company, St. Louis, MO; 1989.
Avigan et al. (1990) J Biolog Chem. 265(30), 18538–18545.
Briggs et al. (1986) Science, 234, 47–52.
Gould et al. (1989) Proc. Natl Acad, Sci, USA 86, 1934–1938.
Matsudaira (1987) J. Biolog. Chem. 262(21), 10035–10038.
Flavin et al. (1991) DNA & Cell Biol. 10(2), 113–118.
Tseng et al. (1994), Cancer Gene Therapy 1(1), 65–71.
Uhlmann et al. (1990). Chem. Rev, 90(4), 543–584.
R. Duncan et al., "The human c–myc FUSE element binds a differentiation regulated protein with a novel structure". 5th International Congress on differntiation therapy, Villasimius, Italy, 2–5 Sep., 1992: *Biomed Pharmacother.*, vol. 46, 5–7 (1992), p. 243, abstract No. 11.
M. Takimoto et al., "A positive cis–element of the human c–myc gene with homo–purine/homo–pyridine–like sequence binds proteins with unusual properties", 5th International Congress on Differentiation Therapy, Villasimius, Italy, 2–5 Sep., 1992; *Biomed. Pharmacother.*, vol. 46, 5–7 (1992), p. 243, abstract No. 10.

M. I. Avignan et al., "A far upstream element stimulates c–myc expression in undifferentiated leukemia cells", *J. Biol. Chem.*, vol. 265, (1990) pp. 18538–18545.

A. D. Bergemann and E. M. Johnson, "The HeLa Pur factor binds single–stranded DNA at a specific element conserved in gene flanking regions and origins of DNA replication", *Mol. Cell. Biol.*, vol. 12, (1992) pp. 1257–1265.

R. Duncan et al., "A sequence–specific, single–strand binding protein activates the far upstream element of c–myc and defines a new DNA–binding motif", *Genes Dev.*, vol. 8, (1994) pp. 465–480. (This reference is published after the filing date and is not prior art).

R. Duncan et al., "Cloning of the cellular factor which binds the far upstream element (FUSE) of c–myc gene", Keystone Symposium on Transcription Regulation, Tamorron, Colorado, USA, 13–20 Jan.; *J. Cell. Biochem.*, vol. 50, Suppl. 0 (16 part A), 1992, p. 83, abstract No. B 211.

*Primary Examiner*—George C. Elliott
*Attorney, Agent, or Firm*—Morgan & Finnegan

[57] ABSTRACT

The Far Upstream Element (FUSE) of the human c-myc gene, stimulates expression in undifferentiated cells. A FUSE binding protein (FBP), also referred to as DROME (DNA-binding regulator of c-myc expression), is active in undifferentiated but not differentiated cell extracts. Cloned FBP exhibits the same DNA-binding specificity as the purified human protein and can trans-activate in a FUSE dependent manner. Sequence-specific binding to the FUSE oligonucleotide required at least two copies of a repeat-helix unit which defines a new DNA-binding motif. Expression of FBP mRNA declined in parallel with decreased FUSE binding activity upon differentiation suggesting transcriptional regulation of FBP. Features were identified in clones which suggested FBP is also regulated by RNA processing, translation and post-translational mechanisms.

50 Claims, 9 Drawing Sheets

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
|1|V|P|D|G|M|V|G|F|I|I|G|R|G|G|E|Q|I|S|R|I|Q|Q|E|S|G|C|K|I|Q|I|
|2|I|P|A|S|K|A|G|L|V|I|G|K|G|G|E|T|I|K|Q|L|Q|E|R|A|G|V|K|M|V|M|
|3|I|P|R|F|A|V|G|I|V|I|G|R|N|G|E|M|I|K|K|I|Q|N|D|A|G|V|R|I|Q|F|
|4|V|P|T|G|K|T|G|L|I|I|G|K|G|G|E|T|I|K|S|I|S|Q|Q|S|G|A|R|I|E|L|

5,580,760

SEQUENCE LISTING ( 1 ) GENERAL INFORMATION:

( i i i ) NUMBER OF SEQUENCES: 24

( 2 ) INFORMATION FOR SEQ ID NO: 1:

( i ) SEQUENCE CHARACTERISTICS:
        ( A ) LENGTH: 2384
        ( B ) TYPE: Nucleic acid
        ( C ) STRANDEDNESS: Double
        ( D ) TOPOLOGY: Unknown ( i i ) MOLECULE TYPE: cDNA ( i i i ) HYPOTHETICAL: No ( i v ) ANTI-SENSE: YES ( v i ) ORIGINAL SOURCE:
        ( A ) ORGANISM: Human
        ( H ) CELL LINE: HL60

( i x ) FEATURE:
        ( D ) OTHER INFORMATION: 473 bp
            variable region where R is A or G.

( x i ) SEQUENCE DESCRIPTION: SEQ ID NO: 1:

```
GCGGCAGCGG  CTCTTATAGT  GCAACC  ATG  GCA  GAC  TAT  TCA  ACA           4 4

GTG  CCT  CCC  CCC  TCT  TCT  GGC  TCA  GCT  GGT  GGC  GGT  GGT        8 3

GGC  GGC  GGT  GGT  GGT  GGA  GGA  GTT  AAC  GAC  GCT  TTC  AAA        1 2 2

GAT  GCA  CTG  CAG  AGA  GCC  CGG  CAG  ATT  GCA  GCA  AAA  ATT        1 6 1

GGA  GGT  GAT  GCA  GGG  ACA  TCA  CTG  AAT  TCA  AAT  GAC  TAT        2 0 0
```

| | | | | | | | | | | | | | |
|---|---|---|---|---|---|---|---|---|---|---|---|---|---|
|GGT|TAT|GGG|GGA|CAA|AAA|AGA|CCT|TTA|GAA|GAT|GGA|GAT|239|
|CAA|CCA|GAT|GCT|AAG|AAA|GTT|GCT|CCT|CAA|AAT|GAC|TCT|278|
|TTT|GGA|ACA|CAG|TTA|CCA|CCG|ATG|CAT|CAG|CAG|CAA|AGC|317|
|AGA|TCT|GTA|ATG|ACA|GAA|GAA|TAC|AAA|GTT|CCA|GAT|GGA|356|
|ATG|GTT|GGA|TTC|ATA|ATT|GGC|AGA|GGA|GGT|GAA|CAG|ATC|395|
|TCA|CGC|ATA|CAA|CAG|GAA|TCT|GGA|TGC|AAA|ATA|CAG|ATA|434|
|GCT|CCT|GAC|AGT|GGT|GGC|CTT|CCA|GAA|AGG|TCC|TGT|ATR|473|
|TTA|ACT|GGA|ACA|CCT|GAA|TCT|GTC|CAG|TCA|GCA|AAA|CGG|512|
|TTA|CTG|GAC|CAG|ATT|GTT|GAA|AAA|GGA|AGA|CCA|GCT|CCT|551|
|GGC|TTC|CAT|CAT|GGC|GAT|GGA|CCG|GGA|AAT|GCA|GTT|CAA|590|
|GAA|ATC|ATG|ATT|CCA|GCT|AGC|AAG|GCA|GGA|TTA|GTC|ATT|629|
|GGA|AAA|GGG|GGA|GAA|ACT|ATT|AAA|CAG|CTT|CAG|GAA|CGG|668|
|GCT|GGA|GTT|AAA|ATG|GTT|ATG|ATT|CAA|GAC|GGG|CCG|CAG|707|
|AAC|ACT|GGT|GCT|GAC|AAA|CCT|CTT|AGG|ATT|ACA|GGA|GAC|746|
|CCA|TAT|AAA|GTT|CAA|CAA|GCC|AAG|GAA|ATG|GTG|TTA|GAG|785|
|TTA|ATT|CGT|GAT|CAA|GGC|GGT|TTC|AGA|GAA|GTT|CGG|AAT|824|
|GAG|TAT|GGG|TCA|AGA|ATA|GGA|GGA|AAT|GAA|GGG|ATA|GAT|863|
|GTC|CCC|ATT|CCA|AGA|TTT|GCT|GTT|GGC|ATT|GTA|ATA|GGA|902|
|AGA|AAT|GGA|GAG|ATG|ATC|AAA|AAA|ATA|CAA|AAT|GAT|GCT|941|
|GGT|GTT|CGC|ATT|CAG|TTT|AAG|CCA|GAT|GAT|GGG|ACA|ACA|980|
|CCC|GAA|AGG|ATA|GCA|CAA|ATA|ACA|GGA|CCT|CCA|GAC|CGA|1019|
|TGT|CAA|CAT|GCT|GCA|GAA|ATT|ATT|ACA|GAC|CTT|CTT|CGA|1058|
|AGT|GTT|CAG|GCT|GGT|AAT|CCT|GGT|GGA|CCT|GGA|CCT|GGT|1097|
|GGT|CGA|GGA|AGA|GGT|AGA|GGT|CAA|GGC|AAC|TGG|AAC|ATG|1136|
|GGA|CCA|CCT|GGT|GGA|TTA|CAG|GAA|TTT|AAT|TTT|ATT|GTG|1175|
|CCA|ACT|GGG|AAA|ACT|GGA|TTA|ATA|ATA|GGA|AAA|GGA|GGT|1214|
|GAA|ACC|ATA|AAA|AGC|ATA|AGC|CAG|CAG|TCT|GGT|GCA|AGA|1253|
|ATA|GAA|CTT|CAG|AGA|AAT|CCT|CCA|CCA|AAT|GCA|GAT|CCT|1292|
|AAT|ATG|AAG|TTA|TTT|ACA|ATT|CGT|GGC|ACT|CCA|CAA|CAG|1331|
|ATA|GAC|TAT|GCT|CGG|CAA|CTC|ATA|GAA|GAA|AAG|ATT|GGT|1370|
|GGC|CCA|GTA|AAT|CCT|TTA|GGG|CCA|CCT|GTA|CCC|CAT|GGG|1409|
|CCC|CAT|GGT|GTC|CCA|GGC|CCC|CAT|GGA|CCT|CCT|GGG|CCT|1448|
|CCA|GGG|CCT|GGA|ACT|CCA|ATG|GGA|CCA|TAC|AAC|CCT|GCA|1487|
|CCT|TAT|AAT|CCT|GGA|CCA|CCA|GGC|CCG|GCT|CCT|CAT|GGT|1526|
|CCT|CCA|GCC|CCA|TAT|GCT|CCC|CAG|GGA|TGG|GGA|AAT|GCA|1565|
|TAT|CCA|CAC|TGG|CAG|CAG|CAG|GCT|CCT|CCT|GAT|CCA|GCT|1604|
|AAG|GCA|GGA|ACG|GAT|CCA|AAT|TCA|GCA|GCT|TGG|GCT|GCT|1643|
|TAT|TAC|GCT|CAC|TAT|TAT|CAA|CAG|CAA|GCA|CAG|CCA|CCA|1682|
|CCA|GCA|GCC|CCT|GCA|GGT|GCA|CCA|ACT|ACA|ACT|CAA|ACT|1721|
|AAT|GGA|CAA|GGA|GAT|CAG|CAG|AAT|CCA|GCC|CCA|GCT|GGA|1760|

-continued

| | | | | | | | | | | | | |
|---|---|---|---|---|---|---|---|---|---|---|---|---|
| CAG | GTT | GAT | TAT | ACC | AAG | GCT | TGG | GAA | GAG | TAC | TAC | AAG | 1799 |
| AAA | ATG | GGT | CAG | GCA | GTT | CCT | GCT | CCG | ACT | GGG | GCT | CCT | 1838 |
| CCA | GGT | GGT | CAG | CCA | GAT | TAT | AGT | GCA | GCC | TGG | GCT | GAG | 1877 |
| CAT | TAT | AGA | CAA | CAA | GCA | GCC | TAT | TAT | GCC | CAG | ACA | AGT | 1916 |
| CCC | CAG | GGA | ATG | CCA | CAG | CAT | CCT | CCA | GCA | CCT | CAG | GGC | 1955 |
| CAA | TAA | TAA | GAAGTGGACA | | ATACAGTATT | | TGCTTCATTG | | | | | | 1994 |

```
TGTGGGGGAA  AAAAACCTTT  GTTAAATATA  TGGATGCAGA                        2034
CGACTTGATG  AAGATCTTAA  TTTTGTTTTT  GGTTTAAAAT                        2074
AGTGTTTCCT  TTTTTTTTTT  TTTTTTTTTG  AAAATGTACA                        2114
AAATATCTAT  CACTACTGAT  AGGAGGTTAA  TATTTCTGTG                        2154
TAGAAATGAA  AATTGGTTTG  TTTTAGTAT   TTAGTGTAGA                        2194
TGTACACATT  CCAGCAAATG  TATTTGCAAT  TATGTGGTTG                        2234
ATGCTTTGTG  ATATAAATGT  ACTTTTCAA   TGTATACTTT                        2274
CACTTTCCAA  ATGCCTGTTT  TGTGCTTTAC  AATAAATGAT                        2314
ATGAAACCTC  AAAAAAAAAA  AAAAAAAAAA  AAAAAAAAAA                        2354
AAAAAAAAAA  AAAAAAAAAA  AAAAAAAAA                                     2384
```

(2) INFORMATION FOR SEQ ID NO: 2:

(i) SEQUENCE CHARACTERISTICS:
        (A) LENGTH: 644
        (B) TYPE: Amino Acid
        (C) STRANDEDNESS: Single
        (D) TOPOLOGY: Unknown (ii) MOLECULE TYPE: Peptide/Protein (iii) HYPOTHETICAL: No (vi) ORIGINAL SOURCE:
        (A) ORGANISM: Human
        (H) CELL LINE: HL60

(ix) FEATURE:
        (D) OTHER INFORMATION:
            Amino Acid 149 (Xaa) is Met or Ile (xi) SEQUENCE DESCRIPTION: SEQ ID NO: 2:

```
Met  Ala  Asp  Tyr  Ser  Thr  Val  Pro  Pro  Pro  Ser  Ser  Gly
 1              5                   10
Ser  Ala  Gly  Gly  Gly  Gly  Gly  Gly  Gly  Gly  Gly  Gly  Gly
     15                  20                       25
Val  Asn  Asp  Ala  Phe  Lys  Asp  Ala  Leu  Gln  Arg  Ala  Arg
               30                  35
Gln  Ile  Ala  Ala  Lys  Ile  Gly  Gly  Asp  Ala  Gly  Thr  Ser
40                       45                  50
Leu  Asn  Ser  Asn  Asp  Tyr  Gly  Tyr  Gly  Gly  Gln  Lys  Arg
          55                  60                            65
Pro  Leu  Glu  Asp  Gly  Asp  Gln  Pro  Asp  Ala  Lys  Lys  Val
                    70                       75
Ala  Pro  Gln  Asn  Asp  Ser  Phe  Gly  Thr  Gln  Leu  Pro  Pro
     80                       85                            90
Met  His  Gln  Gln  Gln  Ser  Arg  Ser  Val  Met  Thr  Glu  Glu
               95                       100
Tyr  Lys  Val  Pro  Asp  Gly  Met  Val  Gly  Phe  Ile  Ile  Gly
```

|     |     |     | 105 |     |     |     | 110 |     |     |     | 115 |     |
| --- | --- | --- | --- | --- | --- | --- | --- | --- | --- | --- | --- | --- |
| Arg | Gly | Gly | Glu | Gln | Ile | Ser | Arg | Ile | Gln | Gln | Glu | Ser |
|     |     | 120 |     |     |     |     | 125 |     |     |     |     | 130 |
| Gly | Cys | Lys | Ile | Gln | Ile | Ala | Pro | Asp | Ser | Gly | Gly | Leu |
|     |     |     |     | 135 |     |     |     |     | 140 |     |     |     |
| Pro | Glu | Arg | Ser | Cys | Xaa | Leu | Thr | Gly | Thr | Pro | Glu | Ser |
|     | 145 |     |     |     |     | 150 |     |     |     |     | 155 |     |
| Val | Gln | Ser | Ala | Lys | Arg | Leu | Leu | Asp | Gln | Ile | Val | Glu |
|     |     |     | 160 |     |     |     |     | 165 |     |     |     |     |
| Lys | Gly | Arg | Pro | Ala | Pro | Gly | Phe | His | His | Gly | Asp | Gly |
| 170 |     |     |     |     | 175 |     |     |     |     | 180 |     |     |
| Pro | Gly | Asn | Ala | Val | Gln | Glu | Ile | Met | Ile | Pro | Ala | Ser |
|     |     | 185 |     |     |     |     | 190 |     |     |     |     | 195 |
| Lys | Ala | Gly | Leu | Val | Ile | Gly | Lys | Gly | Gly | Glu | Thr | Ile |
|     |     |     |     | 200 |     |     |     |     | 205 |     |     |     |
| Lys | Gln | Leu | Gln | Glu | Arg | Ala | Gly | Val | Lys | Met | Val | Met |
|     | 210 |     |     |     |     | 215 |     |     |     |     | 220 |     |
| Ile | Gln | Asp | Gly | Pro | Gln | Asn | Thr | Gly | Ala | Asp | Lys | Pro |
|     |     |     | 225 |     |     |     |     | 230 |     |     |     |     |
| Leu | Arg | Ile | Thr | Gly | Asp | Pro | Tyr | Lys | Val | Gln | Gln | Ala |
| 235 |     |     |     |     | 240 |     |     |     |     | 245 |     |     |
| Lys | Glu | Met | Val | Leu | Glu | Leu | Ile | Arg | Asp | Gln | Gly | Gly |
|     |     | 250 |     |     |     |     | 255 |     |     |     |     | 260 |
| Phe | Arg | Glu | Val | Arg | Asn | Glu | Tyr | Gly | Ser | Arg | Ile | Gly |
|     |     |     |     | 265 |     |     |     |     | 270 |     |     |     |
| Gly | Asn | Glu | Gly | Ile | Asp | Val | Pro | Ile | Pro | Arg | Phe | Ala |
|     | 275 |     |     |     |     | 280 |     |     |     |     | 285 |     |
| Val | Gly | Ile | Val | Ile | Gly | Arg | Asn | Gly | Glu | Met | Ile | Lys |
|     |     |     | 290 |     |     |     |     | 295 |     |     |     |     |
| Lys | Ile | Gln | Asn | Asp | Ala | Gly | Val | Arg | Ile | Gln | Phe | Lys |
| 300 |     |     |     |     | 305 |     |     |     |     | 310 |     |     |
| Pro | Asp | Asp | Gly | Thr | Thr | Pro | Glu | Arg | Ile | Ala | Gln | Ile |
|     |     | 315 |     |     |     |     | 320 |     |     |     |     | 325 |
| Thr | Gly | Pro | Pro | Asp | Arg | Cys | Gln | His | Ala | Ala | Glu | Ile |
|     |     |     |     | 330 |     |     |     |     | 335 |     |     |     |
| Ile | Thr | Asp | Leu | Leu | Arg | Ser | Val | Gln | Ala | Gly | Asn | Pro |
|     | 340 |     |     |     |     | 345 |     |     |     |     | 350 |     |
| Gly | Gly | Pro | Gly | Pro | Gly | Gly | Arg | Gly | Arg | Gly | Arg | Gly |
|     |     |     | 355 |     |     |     |     | 360 |     |     |     |     |
| Gln | Gly | Asn | Trp | Asn | Met | Gly | Pro | Pro | Gly | Gly | Leu | Gln |
| 365 |     |     |     |     | 370 |     |     |     |     | 375 |     |     |
| Glu | Phe | Asn | Phe | Ile | Val | Pro | Thr | Gly | Lys | Thr | Gly | Leu |
|     |     | 380 |     |     |     |     | 385 |     |     |     |     | 390 |
| Ile | Ile | Gly | Lys | Gly | Gly | Glu | Thr | Ile | Lys | Ser | Ile | Ser |
|     |     |     |     | 395 |     |     |     |     | 400 |     |     |     |
| Gln | Gln | Ser | Gly | Ala | Arg | Ile | Glu | Leu | Gln | Arg | Asn | Pro |
|     | 405 |     |     |     |     | 410 |     |     |     |     | 415 |     |
| Pro | Pro | Asn | Ala | Asp | Pro | Asn | Met | Lys | Leu | Phe | Thr | Ile |
|     |     |     | 420 |     |     |     |     | 425 |     |     |     |     |
| Arg | Gly | Thr | Pro | Gln | Gln | Ile | Asp | Tyr | Ala | Arg | Gln | Leu |
| 430 |     |     |     |     | 435 |     |     |     |     | 440 |     |     |
| Ile | Glu | Glu | Lys | Ile | Gly | Gly | Pro | Val | Asn | Pro | Leu | Gly |
|     |     | 445 |     |     |     |     | 450 |     |     |     |     | 455 |

```
Pro  Pro  Val  Pro  His  Gly  Pro  His  Gly  Val  Pro  Gly  Pro
               460                      465

His  Gly  Pro  Pro  Gly  Pro  Pro  Gly  Pro  Gly  Thr  Pro  Met
     470                 475                      480

Gly  Pro  Tyr  Asn  Pro  Ala  Pro  Tyr  Asn  Pro  Gly  Pro  Pro
               485                 490

Gly  Pro  Ala  Pro  His  Gly  Pro  Pro  Ala  Pro  Tyr  Ala  Pro
495                      500                      505

Gln  Gly  Trp  Gly  Asn  Ala  Tyr  Pro  His  Trp  Gln  Gln  Gln
               510                 515                      520

Ala  Pro  Pro  Asp  Pro  Ala  Lys  Ala  Gly  Thr  Asp  Pro  Asn
                    525                      530

Ser  Ala  Ala  Trp  Ala  Ala  Tyr  Tyr  Ala  His  Tyr  Tyr  Gln
     535                      540                      545

Gln  Gln  Ala  Gln  Pro  Pro  Pro  Ala  Ala  Pro  Ala  Gly  Ala
               550                      555

Pro  Thr  Thr  Thr  Gln  Thr  Asn  Gly  Gln  Gly  Asp  Gln  Gln
560                      565                      570

Asn  Pro  Ala  Pro  Ala  Gly  Gln  Val  Asp  Tyr  Thr  Lys  Ala
          575                 580                           585

Trp  Glu  Glu  Tyr  Tyr  Lys  Lys  Met  Gly  Gln  Ala  Val  Pro
               590                      595

Ala  Pro  Thr  Gly  Ala  Pro  Pro  Gly  Gly  Gln  Pro  Asp  Tyr
     600                 605                      610

Ser  Ala  Ala  Trp  Ala  Glu  His  Tyr  Arg  Gln  Gln  Ala  Ala
               615                      620

Tyr  Tyr  Ala  Gln  Thr  Ser  Pro  Gln  Gly  Met  Pro  Gln  His
625                      630                      635

Pro  Pro  Ala  Pro  Gln  Gly  Gln
          640
```

( 2 ) INFORMATION FOR SEQ ID NO:3:

( i ) SEQUENCE CHARACTERISTICS:
          ( A ) LENGTH: 27
          ( B ) TYPE: Nucleic acid
          ( C ) STRANDEDNESS: Single
          ( D ) TOPOLOGY: Unknown ( i i ) MOLECULE TYPE: cDNA ( i i i ) HYPOTHETICAL: No ( v i ) ORIGINAL SOURCE:
          ( A ) ORGANISM: Human ( i x ) FEATURE:
          ( A ) NAME/KEY:
          ( B ) LOCATION:
          ( C ) IDENTIFICATION METHOD:
          ( D ) OTHER INFORMATION: N at positions
              11, 14, and 23 is inosine (I);
              Y is either T or C; R is either
              A or G; N at position 25 is either
              I or T.

( i x ) SEQUENCE DESCRIPTION: SEQ ID NO: 3:

CAGAATTCGG NGGNAAYGAR GGNANCG          27

( 2 ) INFORMATION FOR SEQ ID NO:4:

( i ) SEQUENCE CHARACTERISTICS:
          ( A ) LENGTH: 26

(B) TYPE: Nucleic acid
(C) STRANDEDNESS: Single
(D) TOPOLOGY: Unknown (ii) MOLECULE TYPE: cDNA (iii) HYPOTHETICAL: No (vi) ORIGINAL SOURCE:
    (A) ORGANISM: Human (ix) FEATURE:
    (D) OTHER INFORMATION: N is inosine;
        R is either A or G; Y is
        either C or T.

(xi) SEQUENCE DESCRIPTION: SEQ ID NO: 4:

```
GAGTCGACRT CRTCRTCNGG YTTRAA                                              26
```

(2) INFORMATION FOR SEQ ID NO: 5:

(i) SEQUENCE CHARACTERISTICS:
    (A) LENGTH: 1097
    (B) TYPE: Nucleic acid
    (C) STRANDEDNESS: Double
    (D) TOPOLOGY: Unknown (ii) MOLECULE TYPE: cDNA (iii) HYPOTHETICAL: No (iv) ANTI-SENSE: YES (vi) ORIGINAL SOURCE:
    (A) ORGANISM: Human
    (H) CELL LINE: HL60

(xi) SEQUENCE DESCRIPTION: SEQ ID NO: 5:

```
GGAATTCCGG ATA GAT GTC CCC ATT CCA AGA TTT GCT GTT                        40
GGC ATT GTA ATA GGA AGA AAT GGA GAG ATG ATC AAA AAA                       79
ATA CAA AAT GAT GCT GGT GTT CGC ATT CAG TTT AAG CCA                      118
GAT GAT GGG ACA ACA CCC GAA AGG ATA GCA CAA ATA ACA                      157
GGA CCT CCA GAC CGA TGT CAA CAT GCT GCA GAA ATT ATT                      196
ACA GAC CTT CTT CGA AGT GTT CAG GCT GGT AAT CCT GGT                      235
GGA CCT GGA CCT GGT GGT CGA GGA AGA GGT AGA GGT CAA                      274
GGC AAC TGG AAC ATG GGA CCA CCT GGT GGA TTA CAG GAA                      313
TTT AAT TTT ATT GTG CCA ACT GGG AAA ACT GGA TTA ATA                      352
ATA GGA AAA GGA GGT GAA ACC ATA AAA AGC ATA AGC CAG                      391
CAG TCT GGT GCA AGA ATA GAA CTT CAG AGA AAT CCT CCA                      430
CCA AAT GCA GAT CCT AAT ATG AAG TTA TTT ACA ATT CGT                      469
GGC ACT CCA CAA CAG ATA GAC TAT GCT CGG CAA CTC ATA                      508
GAA GAA AAG ATT GGT GGC CCA GTA AAT CCT TTA GGG CCA                      547
CCT GTA CCC CAT GGG CCC CAT GGT GTC CCA GGC CCC CAT                      586
GGA CCT CCT GGG CCT CCA GGG CCT GGA ACT CCA ATG GGA                      625
CCA TAC AAC CCT GCA CCT TAT AAT CCT GGA CCA CCA GGC                      664
CCG GCT CCT CAT GGT CCT CCA GCC CCA TAT GCT CCC CAG                      703
GGA TGG GGA AAG GAA ATT GAG CAG AAG GTA CAG GAG TAA                      742
TAG CAATTCCCTG TAGCTCTCAA AGCAAATTTT GAGCTCATTT                          785
```

```
TTCTTTTTCT  GCAAGCTCAG  CAGCAGAATG  CCCAGAGTCT                      825

TCCCTGGTAG  ATGCAGGTTC  CATAGCGACG  TTCTCCTGCA                      865

ATGCACGCTG  GTATTCTGCA  ATAGCAGGCC  ATGTTTTCCT                      905

TGAGCCTGGA  TGCTTTGGAG  CCAAGCTTTC  GTCCCATGCA                      945

AGGGAAACAA  CCACTTCTGG  GATGTCCGCT  GCAATCTGCT                      985

CCGGGGCTGC  AGCAACCTCA  TCAGCTCTCT  TGCCTGGAGT                     1025

GGCTCAGCCT  GGCCTGCAGG  GCCACCAGGA  GAATGGCAGC                     1065

AAGGATGGCG  AGGGTCCTCA  TGGCTGGAAT  TC                             1097
```

( 2 ) INFORMATION FOR SEQ ID NO: 6:

( i ) SEQUENCE CHARACTERISTICS:
        ( A ) LENGTH: 243
        ( B ) TYPE: Amino Acid
        ( C ) STRANDEDNESS: Single
        ( D ) TOPOLOGY: Unknown ( i i ) MOLECULE TYPE: Peptide/Protein ( i i i ) HYPOTHETICAL: No ( v i ) ORIGINAL SOURCE:
        ( A ) ORGANISM: Human
        ( G ) CELL TYPE: HL60

( i x ) SEQUENCE DESCRIPTION: SEQ ID NO: 6:

```
            Ile  Asp  Val  Pro  Ile  Pro  Arg  Phe  Ala  Val
             1                   5                        10

Gly  Ile  Val  Ile  Gly  Arg  Asn  Gly  Glu  Met  Ile  Lys  Lys
                     15                    20

Ile  Gln  Asn  Asp  Ala  Gly  Val  Arg  Ile  Gln  Phe  Lys  Pro
          25                    30                    35

Asp  Asp  Gly  Thr  Thr  Pro  Glu  Arg  Ile  Ala  Gln  Ile  Thr
                40                         45

Gly  Pro  Pro  Asp  Arg  Cys  Gln  His  Ala  Ala  Glu  Ile  Ile
 50                      55                         60

Thr  Asp  Leu  Leu  Arg  Ser  Val  Gln  Ala  Gly  Asn  Pro  Gly
               65                    70                        75

Gly  Pro  Gly  Pro  Gly  Gly  Arg  Gly  Arg  Gly  Arg  Gly  Gln
                     80                    85

Gly  Asn  Trp  Asn  Met  Gly  Pro  Pro  Gly  Gly  Leu  Gln  Glu
     90                    95                        100

Phe  Asn  Phe  Ile  Val  Pro  Thr  Gly  Lys  Thr  Gly  Leu  Ile
               105                   110

Ile  Gly  Lys  Gly  Gly  Glu  Thr  Ile  Lys  Ser  Ile  Ser  Gln
115                   120                        125

Gln  Ser  Gly  Ala  Arg  Ile  Glu  Leu  Gln  Arg  Asn  Pro  Pro
          130                   135                        140

Pro  Asn  Ala  Asp  Pro  Asn  Met  Lys  Leu  Phe  Thr  Ile  Arg
                    145                   150

Gly  Thr  Pro  Gln  Gln  Ile  Asp  Tyr  Ala  Arg  Gln  Leu  Ile
     155                        160                   165

Glu  Glu  Lys  Ile  Gly  Gly  Pro  Val  Asn  Pro  Leu  Gly  Pro
               170                   175

Pro  Val  Pro  His  Gly  Pro  His  Gly  Val  Pro  Gly  Pro  His
180                        185                   190
```

```
Gly  Pro  Pro  Gly  Pro  Pro  Gly  Pro  Gly  Thr  Pro  Met  Gly
          195                      200                     205

Pro  Tyr  Asn  Pro  Ala  Pro  Tyr  Asn  Pro  Gly  Pro  Pro  Gly
               210                      215

Pro  Ala  Pro  His  Gly  Pro  Pro  Ala  Pro  Tyr  Ala  Pro  Gln
          220                 225                     230

Gly  Trp  Gly  Lys  Glu  Ile  Glu  Gln  Lys  Val  Gln  Glu
               235                      240
```

(2) INFORMATION FOR SEQ ID NO: 7:

(i) SEQUENCE CHARACTERISTICS:
        (A) LENGTH: 1803
        (B) TYPE: Nucleic acid
        (C) STRANDEDNESS: Double
        (D) TOPOLOGY: Unknown (ii) MOLECULE TYPE: cDNA (iii) HYPOTHETICAL: No (iv) ANTI-SENSE: YES (vi) ORIGINAL SOURCE:
        (A) ORGANISM: Human
        (H) CELL LINE: HL60

(xi) SEQUENCE DESCRIPTION: SEQ ID NO: 7:

```
GAATTCCGGA CGACAGCGGC TCTG AGA GCC CGG CAG ATT GCA                    42

GCA AAA ATT GGA GGT GAT GCA GGG ACA TCA CTG AAT TCA                   81

AAT GAC TAT GGT TAT GGG GGA CAA AAA AGA CCT TTA GAA                   120

GAT GGA GAT GGC TCT TGG ACA AGT CCG AGC AGT ACA ACA                   159

CAC TGG GAG GGA ATG CCC TCT CCT TTT AAA GAT CAA CCA                   198

GAT GCT AAG AAA GTT GCT CCT CAA AAT GAC TCT TTT GGA                   237

ACA CAG TTA CCA CCG ATG CAT CAG CAG CAA AGA TCT GTA                   276

ATG ACA GAA GAA TAC AAA GTT CCA GAT GGA ATG GTT GGA                   315

TTC ATA ATT GGC AGA GGA GGT GAA CAG ATC TCA CGC ATA                   354

CAA CAG GAA TCT GGA TGC AAA ATA CAG ATA GCT CCT GAC                   393

AGT GGT GGC CTT CCA GAA AGG TCC TGT ATG TTA ACT GGA                   432

ACA CCT GAA TCT GTC CAG TCA GCA AAA CGG TTA CTG GAC                   471

CAG ATT GTT GAA AAA GGA AGA CCA GCT CCT GGC TTC CAT                   510

CAT GGC GAT GGA CCG GGA AAT GCA GTT CAA GAA ATC ATG                   549

ATT CCA GCT AGC AAG GCA GGA TTA GTC ATT GGA AAA GGG                   588

GGA GAA ACT ATT AAA CAG CTT CAG GAA CGG GCT GGA GTT                   627

AAA ATG GTT ATG ATT CAA GAC GGG CCG CAG AAC ACT GGT                   666

GCT GAC AAA CCT CTT AGG ATT ACA GGA GAC CCA TAT AAA                   705

GTT CAA CAA GCC AAG GAA ATG GTG TTA GAG TTA ATT CGT                   744

GAT CAA GGC GGT TTC AGA GAA GTT CGG AAT GAG TAT GGG                   783

TCA AGA ATA GGA GGA AAT GAA GGG ATA GAT GTC CCC ATT                   822

CCA AGA TTT GCT GTT GGC ATT GTA ATA GGA AGA AAT GGA                   861

GAG ATG ATC AAA AAA ATA CAA AAT GAT GCT GGT GTT CGC                   900
```

| | | | | | | | | | | | | |
|---|---|---|---|---|---|---|---|---|---|---|---|---|
|ATT|CAG|TTT|AAG|CCA|GAT|GAT|GGG|ACA|ACA|CCC|GAA|AGG|939|
|ATA|GCA|CAA|ATA|ACA|GGA|CCT|CCA|GAC|CGA|TGT|CAA|CAT|978|
|GCT|GCA|GAA|ATT|ATT|ACA|GAC|CTT|CTT|CGA|AGT|GTT|CAG|1017|
|GCT|GGT|AAT|CCT|GGT|GGA|CCT|GGA|CCT|GGT|GGT|CGA|GGA|1056|
|AGA|GGT|AGA|GGT|CAA|GGC|AAC|TGG|AAC|ATG|GGA|CCA|CCT|1095|
|GGT|GGA|TTA|CAG|GAA|TTT|AAT|TTT|ATT|GTG|CCA|ACT|GGG|1134|
|AAA|ACT|GGA|TTA|ATA|ATA|GGA|AAA|GGA|GGT|GAA|ACC|ATA|1173|
|AAA|AGC|ATA|AGC|CAG|CAG|TCT|GGT|GCA|AGA|ATA|GAA|CTT|1212|
|CAG|AGA|AAT|CCT|CCA|CCA|AAT|GCA|GAT|CCT|AAT|ATG|AAG|1251|
|TTA|TTT|ACA|ATT|CGT|GGC|ACT|CCA|CAA|CAG|ATA|GAC|TAT|1290|
|GCT|CGG|CAA|CTC|ATA|GAA|GAA|AAG|ATT|GGT|GGC|CCA|GTA|1329|
|AAT|CCT|TTA|GGG|CCA|CCT|GTA|CCC|CAT|GGG|CCC|CAT|GGT|1368|
|GTC|CCA|GGC|CCC|CAT|GGA|CCT|CCT|GGG|CCT|CCA|GGG|CCT|1407|
|GGA|ACT|CCA|ATG|GGA|CCA|TAC|AAC|CCT|GCA|CCT|TAT|AAT|1446|
|CCT|GGA|CCA|CCA|GGC|CCG|GCT|CCT|CAT|GGT|CCT|CCA|GCC|1485|
|CCA|TAT|GCT|CCC|CAG|GGA|TGG|GGA|AAT|GCA|TAT|CCA|CAC|1524|
|TGG|CAG|CAG|CAG|GCT|CCT|CCT|GAT|CCA|GCT|AAG|GCA|GGA|1563|
|ACG|GAT|CCA|AAT|TCA|GCA|GCT|TGG|GCT|GCT|TAT|TAC|GCT|1602|
|CAC|TAT|TAT|CAA|CAG|CAA|GCA|CAG|CCA|CCA|CCA|GCA|GCC|1641|
|CCT|GCA|GGT|GCA|CCA|ACT|ACA|ACT|CAA|ACT|AAT|GGA|CAA|1680|
|GGA|GAT|CAG|CAG|AAT|CCA|GCC|CCA|GCT|GGA|CAG|GTT|GAT|1719|
|TAT|ACC|AAG|GCT|TGG|GAA|GAG|TAC|TAC|AAG|AAA|ATG|GGG|1758|
|CCA|ATA|ATA|AGA|AGT|GGA|CAA|TAC|AGT|ATT|TGC|TTC| |1794|
|AGGAATTCC| | | | | | | | | | | | |1803|

( 2 ) INFORMATION FOR SEQ ID NO: 8:

( i ) SEQUENCE CHARACTERISTICS:
        ( A ) LENGTH: 590
        ( B ) TYPE: Amino Acid
        ( C ) STRANDEDNESS: Single
        ( D ) TOPOLOGY: Unknown ( i i ) MOLECULE TYPE: Peptide/Protein ( i i i ) HYPOTHETICAL: No ( v i ) ORIGINAL SOURCE:
        ( A ) ORGANISM: Human
        ( H ) CELL LINE: HL60

( x i ) SEQUENCE DESCRIPTION: SEQ ID NO: 8:

```
                              Arg  Ala  Arg  Gln  Ile  Ala
                               1                    5

Ala  Lys  Ile  Gly  Gly  Asp  Ala  Gly  Thr  Ser  Leu  Asn  Ser
                    10                    15

Asn  Asp  Tyr  Gly  Tyr  Gly  Gly  Gln  Lys  Arg  Pro  Leu  Glu
20                        25                        30

Asp  Gly  Asp  Gly  Ser  Trp  Thr  Ser  Pro  Ser  Ser  Thr  Thr
               35                    40                        45

His  Trp  Glu  Gly  Met  Pro  Ser  Pro  Phe  Lys  Asp  Gln  Pro
```

```
                         50                              55
Asp  Ala  Lys  Lys  Val  Ala  Pro  Gln  Asn  Asp  Ser  Phe  Gly
     60                      65                  70

Thr  Gln  Leu  Pro  Pro  Met  His  Gln  Gln  Arg  Ser  Val
               75                      80

Met  Thr  Glu  Glu  Tyr  Lys  Val  Pro  Asp  Gly  Met  Val  Gly
85                       90                       95

Phe  Ile  Ile  Gly  Arg  Gly  Gly  Glu  Gln  Ile  Ser  Arg  Ile
          100                      105                      110

Gln  Gln  Glu  Ser  Gly  Cys  Lys  Ile  Gln  Ile  Ala  Pro  Asp
               115                      120

Ser  Gly  Gly  Leu  Pro  Glu  Arg  Ser  Cys  Met  Leu  Thr  Gly
     125                 130                           135

Thr  Pro  Glu  Ser  Val  Gln  Ser  Ala  Lys  Arg  Leu  Leu  Asp
               140                      145

Gln  Ile  Val  Glu  Lys  Gly  Arg  Pro  Ala  Pro  Gly  Phe  His
150                      155                      160

His  Gly  Asp  Gly  Pro  Gly  Asn  Ala  Val  Gln  Glu  Ile  Met
          165                 170                           175

Ile  Pro  Ala  Ser  Lys  Ala  Gly  Leu  Val  Ile  Gly  Lys  Gly
                    180                      185

Gly  Glu  Thr  Ile  Lys  Gln  Leu  Gln  Glu  Arg  Ala  Gly  Val
190                      195                      200

Lys  Met  Val  Met  Ile  Gln  Asp  Gly  Pro  Gln  Asn  Thr  Gly
               205                      210

Ala  Asp  Lys  Pro  Leu  Arg  Ile  Thr  Gly  Asp  Pro  Tyr  Lys
215                      220                      225

Val  Gln  Gln  Ala  Lys  Glu  Met  Val  Leu  Glu  Leu  Ile  Arg
     230                      235                           240

Asp  Gln  Gly  Gly  Phe  Arg  Glu  Val  Arg  Asn  Glu  Tyr  Gly
               245                      250

Ser  Arg  Ile  Gly  Gly  Asn  Glu  Gly  Ile  Asp  Val  Pro  Ile
     255                 260                      265

Pro  Arg  Phe  Ala  Val  Gly  Ile  Val  Ile  Gly  Arg  Asn  Gly
               270                      275

Glu  Met  Ile  Lys  Lys  Ile  Gln  Asn  Asp  Ala  Gly  Val  Arg
280                      285                      290

Ile  Gln  Phe  Lys  Pro  Asp  Asp  Gly  Thr  Thr  Pro  Glu  Arg
               295                 300                      305

Ile  Ala  Gln  Ile  Thr  Gly  Pro  Pro  Asp  Arg  Cys  Gln  His
               310                      315

Ala  Ala  Glu  Ile  Ile  Thr  Asp  Leu  Leu  Arg  Ser  Val  Gln
320                      325                      330

Ala  Gly  Asn  Pro  Gly  Gly  Pro  Gly  Pro  Gly  Gly  Arg  Gly
               335                 340

Arg  Gly  Arg  Gly  Gln  Gly  Asn  Trp  Asn  Met  Gly  Pro  Pro
345                      350                      355

Gly  Gly  Leu  Gln  Glu  Phe  Asn  Phe  Ile  Val  Pro  Thr  Gly
          360                      365                      370

Lys  Thr  Gly  Leu  Ile  Ile  Gly  Lys  Gly  Gly  Glu  Thr  Ile
                    375                      380

Lys  Ser  Ile  Ser  Gln  Gln  Ser  Gly  Ala  Arg  Ile  Glu  Leu
     385                      390                           395
```

| | | | | | | | | | | | |
|---|---|---|---|---|---|---|---|---|---|---|---|
|Gln|Arg|Asn|Pro<br>400|Pro|Pro|Asn|Ala|Asp<br>405|Pro|Asn|Met|Lys|
|Leu<br>410|Phe|Thr|Ile|Arg|Gly<br>415|Thr|Pro|Gln|Gln|Ile<br>420|Asp|Tyr|
|Ala|Arg|Gln<br>425|Leu|Ile|Glu|Glu|Lys<br>430|Ile|Gly|Gly|Pro|Val<br>435|
|Asn|Pro|Leu|Gly|Pro<br>440|Pro|Val|Pro|His|Gly<br>445|Pro|His|Gly|
|Val|Pro<br>450|Gly|Pro|His|Gly|Pro<br>455|Pro|Gly|Pro|Pro|Gly<br>460|Pro|
|Gly|Thr|Pro|Met<br>465|Gly|Pro|Tyr|Asn|Pro<br>470|Ala|Pro|Tyr|Asn|
|Pro<br>475|Gly|Pro|Pro|Gly|Pro<br>480|Ala|Pro|His|Gly|Pro<br>485|Pro|Ala|
|Pro|Tyr|Ala<br>490|Pro|Gln|Gly|Trp|Gly<br>495|Asn|Ala|Tyr|Pro|His<br>500|
|Trp|Gln|Gln|Gln|Ala<br>505|Pro|Pro|Asp|Pro|Ala<br>510|Lys|Ala|Gly|
|Thr|Asp<br>515|Pro|Asn|Ser|Ala|Ala<br>520|Trp|Ala|Ala|Tyr|Tyr<br>525|Ala|
|His|Tyr|Tyr|Gln<br>530|Gln|Gln|Ala|Gln|Pro<br>535|Pro|Pro|Ala|Ala|
|Pro<br>540|Ala|Gly|Ala|Pro|Thr<br>545|Thr|Thr|Gln|Thr|Asn|Gly<br>550|Gln|
|Gly|Asp|Gln|Gln<br>555|Asn|Pro|Ala|Pro|Ala<br>560|Gly|Gln|Val|Asp<br>565|
|Tyr|Thr|Lys|Ala|Trp<br>570|Glu|Glu|Tyr|Tyr|Lys<br>575|Lys|Met|Gly|
|Pro<br>580|Ile|Ile|Arg|Ser|Gly<br>585|Gln|Tyr|Ser|Ile|Cys|Phe<br>590|

(2) INFORMATION FOR SEQ ID NO: 9:

(i) SEQUENCE CHARACTERISTICS:
        (A) LENGTH: 2381
        (B) TYPE: Nucleic acid
        (C) STRANDEDNESS: Double
        (D) TOPOLOGY: Unknown (ii) MOLECULE TYPE: cDNA (iii) HYPOTHETICAL: No (iv) ANTI-SENSE: YES (vi) ORIGINAL SOURCE:
        (A) ORGANISM: Human
        (H) CELL LINE: HL60

(ix) FEATURE:
        (D) OTHER INFORMATION: 470 bp variable
            region where R is A or G.

(xi) SEQUENCE DESCRIPTION: SEQ ID NO: 9:

```
GCGGCAGCGG  CTCTTATAGT  GCAACC  ATG  GCA  GAC  TAT  TCA  ACA              44
GTG  CCT  CCC  CCC  TCT  TCT  GGC  TCA  GCT  GGT  GGC  GGT  GGT            83
GGC  GGC  GGT  GGT  GGT  GGA  GGA  GTT  AAC  GAC  GCT  TTC  AAA           122
GAT  GCA  CTG  CAG  AGA  GCC  CGG  CAG  ATT  GCA  GCA  AAA  ATT           161
GGA  GGT  GAT  GCA  GGG  ACA  TCA  CTG  AAT  TCA  AAT  GAC  TAT           200
```

| | |
|---|---|
| GGT TAT GGG GGA CAA AAA AGA CCT TTA GAA GAT GGA GAT | 239 |
| CAA CCA GAT GCT AAG AAA GTT GCT CCT CAA AAT GAC TCT | 278 |
| TTT GGA ACA CAG TTA CCA CCG ATG CAT CAG CAG CAA | 314 |
| AGA TCT GTA ATG ACA GAA GAA TAC AAA GTT CCA GAT GGA | 353 |
| ATG GTT GGA TTC ATA ATT GGC AGA GGA GGT GAA CAG ATC | 392 |
| TCA CGC ATA CAA CAG GAA TCT GGA TGC AAA ATA CAG ATA | 431 |
| GCT CCT GAC AGT GGT GGC CTT CCA GAA AGG TCC TGT ATR | 470 |
| TTA ACT GGA ACA CCT GAA TCT GTC CAG TCA GCA AAA CGG | 509 |
| TTA CTG GAC CAG ATT GTT GAA AAA GGA AGA CCA GCT CCT | 548 |
| GGC TTC CAT CAT GGC GAT GGA CCG GGA AAT GCA GTT CAA | 587 |
| GAA ATC ATG ATT CCA GCT AGC AAG GCA GGA TTA GTC ATT | 626 |
| GGA AAA GGG GGA GAA ACT ATT AAA CAG CTT CAG GAA CGG | 665 |
| GCT GGA GTT AAA ATG GTT ATG ATT CAA GAC GGG CCG CAG | 704 |
| AAC ACT GGT GCT GAC AAA CCT CTT AGG ATT ACA GGA GAC | 743 |
| CCA TAT AAA GTT CAA CAA GCC AAG GAA ATG GTG TTA GAG | 782 |
| TTA ATT CGT GAT CAA GGC GGT TTC AGA GAA GTT CGG AAT | 821 |
| GAG TAT GGG TCA AGA ATA GGA GGA AAT GAA GGG ATA GAT | 860 |
| GTC CCC ATT CCA AGA TTT GCT GTT GGC ATT GTA ATA GGA | 899 |
| AGA AAT GGA GAG ATG ATC AAA AAA ATA CAA AAT GAT GCT | 938 |
| GGT GTT CGC ATT CAG TTT AAG CCA GAT GAT GGG ACA ACA | 977 |
| CCC GAA AGG ATA GCA CAA ATA ACA GGA CCT CCA GAC CGA | 1016 |
| TGT CAA CAT GCT GCA GAA ATT ATT ACA GAC CTT CTT CGA | 1055 |
| AGT GTT CAG GCT GGT AAT CCT GGT GGA CCT GGA CCT GGT | 1094 |
| GGT CGA GGA AGA GGT AGA GGT CAA GGC AAC TGG AAC ATG | 1133 |
| GGA CCA CCT GGT GGA TTA CAG GAA TTT AAT TTT ATT GTG | 1172 |
| CCA ACT GGG AAA ACT GGA TTA ATA ATA GGA AAA GGA GGT | 1211 |
| GAA ACC ATA AAA AGC ATA AGC CAG CAG TCT GGT GCA AGA | 1250 |
| ATA GAA CTT CAG AGA AAT CCT CCA CCA AAT GCA GAT CCT | 1289 |
| AAT ATG AAG TTA TTT ACA ATT CGT GGC ACT CCA CAA CAG | 1328 |
| ATA GAC TAT GCT CGG CAA CTC ATA GAA GAA AAG ATT GGT | 1367 |
| GGC CCA GTA AAT CCT TTA GGG CCA CCT GTA CCC CAT GGG | 1406 |
| CCC CAT GGT GTC CCA GGC CCC CAT GGA CCT CCT GGG CCT | 1445 |
| CCA GGG CCT GGA ACT CCA ATG GGA CCA TAC AAC CCT GCA | 1484 |
| CCT TAT AAT CCT GGA CCA CCA GGC CCG GCT CCT CAT GGT | 1523 |
| CCT CCA GCC CCA TAT GCT CCC CAG GGA TGG GGA AAT GCA | 1562 |
| TAT CCA CAC TGG CAG CAG CAG GCT CCT CCT GAT CCA GCT | 1601 |
| AAG GCA GGA ACG GAT CCA AAT TCA GCA GCT TGG GCT GCT | 1640 |
| TAT TAC GCT CAC TAT TAT CAA CAG CAA GCA CAG CCA CCA | 1679 |
| CCA GCA GCC CCT GCA GGT GCA CCA ACT ACA ACT CAA ACT | 1718 |
| AAT GGA CAA GGA GAT CAG CAG AAT CCA GCC CCA GCT GGA | 1757 |

```
CAG GTT GAT TAT ACC AAG GCT TGG GAA GAG TAC TAC AAG                    1796

AAA ATG GGT CAG GCA GTT CCT GCT CCG ACT GGG GCT CCT                    1835

CCA GGT GGT CAG CCA GAT TAT AGT GCA GCC TGG GCT GAG                    1874

CAT TAT AGA CAA CAA GCA GCC TAT TAT GCC CAG ACA AGT                    1913

CCC CAG GGA ATG CCA CAG CAT CCT CCA GCA CCT CAG GGC                    1952

CAA TAA TAA GAAGTGGACA ATACAGTATT TGCTTCATTG                           1991

TGTGGGGGAA AAAAACCTTT GTTAAATATA TGGATGCAGA                            2031

CGACTTGATG AAGATCTTAA TTTTGTTTTT GGTTTAAAAT                            2071

AGTGTTTCCT TTTTTTTTT TTTTTTTTG AAAATGTACA                              2111

AAATATCTAT CACTACTGAT AGGAGGTTAA TATTTCTGTG                            2151

TAGAAATGAA AATTGGTTTG TTTTAGTAT TTAGTGTAGA                             2191

TGTACACATT CCAGCAAATG TATTTGCAAT TATGTGGTTG                            2231

ATGCTTTGTG ATATAAATGT ACTTTTCAA TGTATACTTT                             2271

CACTTTCCAA ATGCCTGTTT TGTGCTTTAC AATAAATGAT                            2311

ATGAAACCTC AAAAAAAAAA AAAAAAAAAA AAAAAAAAAA                            2351

AAAAAAAAAA AAAAAAAAAA AAAAAAAAA                                        2381
```

( 2 ) INFORMATION FOR SEQ ID NO: 10:

( i ) SEQUENCE CHARACTERISTICS:
        ( A ) LENGTH: 643
        ( B ) TYPE: Amino Acid
        ( C ) STRANDEDNESS: Single
        ( D ) TOPOLOGY: Unknown ( i i ) MOLECULE TYPE: Peptide/Protein ( i i i ) HYPOTHETICAL: No ( v i ) ORIGINAL SOURCE:
        ( A ) ORGANISM: Human
        ( H ) CELL LINE: HL60

( i x ) FEATURE:
        ( D ) OTHER INFORMATION:
            Amino Acid 148 (Xaa) is Met or Ile ( x i ) SEQUENCE DESCRIPTION: SEQ ID NO: 10:

```
Met Ala Asp Tyr Ser Thr Val Pro Pro Pro Ser Ser Gly
 1               5                  10

Ser Ala Gly Gly Gly Gly Gly Gly Gly Gly Gly Gly
     15                  20                  25

Val Asn Asp Ala Phe Lys Asp Ala Leu Gln Arg Ala Arg
                30                  35

Gln Ile Ala Ala Lys Ile Gly Gly Asp Ala Gly Thr Ser
 40              45                  50

Leu Asn Ser Asn Asp Tyr Gly Tyr Gly Gly Gln Lys Arg
         55                  60                  65

Pro Leu Glu Asp Gly Asp Gln Pro Asp Ala Lys Lys Val
                 70                  75

Ala Pro Gln Asn Asp Ser Phe Gly Thr Gln Leu Pro Pro
     80                  85                  90

Met His Gln Gln Gln Arg Ser Val Met Thr Glu Glu
             95                 100

Tyr Lys Val Pro Asp Gly Met Val Gly Phe Ile Ile Gly
```

```
                    105                         110                         115
Arg  Gly  Gly  Glu  Gln  Ile  Ser  Arg  Ile  Gln  Gln  Glu  Ser
               120                      125

Gly  Cys  Lys  Ile  Gln  Ile  Ala  Pro  Asp  Ser  Gly  Gly  Leu
130                      135                      140

Pro  Glu  Arg  Ser  Cys  Xaa  Leu  Thr  Gly  Thr  Pro  Glu  Ser
          145                      150                           155

Val  Gln  Ser  Ala  Lys  Arg  Leu  Leu  Asp  Gln  Ile  Val  Glu
               160                      165

Lys  Gly  Arg  Pro  Ala  Pro  Gly  Phe  His  His  Gly  Asp  Gly
     170                      175                      180

Pro  Gly  Asn  Ala  Val  Gln  Glu  Ile  Met  Ile  Pro  Ala  Ser
               185                      190

Lys  Ala  Gly  Leu  Val  Ile  Gly  Lys  Gly  Gly  Glu  Thr  Ile
195                      200                      205

Lys  Gln  Leu  Gln  Glu  Arg  Ala  Gly  Val  Lys  Met  Val  Met
          210                      215                           220

Ile  Gln  Asp  Gly  Pro  Gln  Asn  Thr  Gly  Ala  Asp  Lys  Pro
                    225                      230

Leu  Arg  Ile  Thr  Gly  Asp  Pro  Tyr  Lys  Val  Gln  Gln  Ala
     235                      240                      245

Lys  Glu  Met  Val  Leu  Glu  Leu  Ile  Arg  Asp  Gln  Gly  Gly
               250                      255

Phe  Arg  Glu  Val  Arg  Asn  Glu  Tyr  Gly  Ser  Arg  Ile  Gly
260                      265                      270

Gly  Asn  Glu  Gly  Ile  Asp  Val  Pro  Ile  Pro  Arg  Phe  Ala
          275                      280                           285

Val  Gly  Ile  Val  Ile  Gly  Arg  Asn  Gly  Glu  Met  Ile  Lys
                    290                      295

Lys  Ile  Gln  Asn  Asp  Ala  Gly  Val  Arg  Ile  Gln  Phe  Lys
     300                      305                      310

Pro  Asp  Asp  Gly  Thr  Thr  Pro  Glu  Arg  Ile  Ala  Gln  Ile
               315                      320

Thr  Gly  Pro  Pro  Asp  Arg  Cys  Gln  His  Ala  Ala  Glu  Ile
325                      330                      335

Ile  Thr  Asp  Leu  Leu  Arg  Ser  Val  Gln  Ala  Gly  Asn  Pro
          340                      345                           350

Gly  Gly  Pro  Gly  Pro  Gly  Gly  Arg  Gly  Arg  Gly  Arg  Gly
                    355                      360

Gln  Gly  Asn  Trp  Asn  Met  Gly  Pro  Pro  Gly  Gly  Leu  Gln
     365                      370                      375

Glu  Phe  Asn  Phe  Ile  Val  Pro  Thr  Gly  Lys  Thr  Gly  Leu
               380                      385

Ile  Ile  Gly  Lys  Gly  Gly  Glu  Thr  Ile  Lys  Ser  Ile  Ser
390                      395                      400

Gln  Gln  Ser  Gly  Ala  Arg  Ile  Glu  Leu  Gln  Arg  Asn  Pro
          405                      410                           415

Pro  Pro  Asn  Ala  Asp  Pro  Asn  Met  Lys  Leu  Phe  Thr  Ile
                    420                      425

Arg  Gly  Thr  Pro  Gln  Gln  Ile  Asp  Tyr  Ala  Arg  Gln  Leu
     430                      435                      440

Ile  Glu  Glu  Lys  Ile  Gly  Gly  Pro  Val  Asn  Pro  Leu  Gly
               445                      450
```

```
Pro   Pro   Val   Pro   His   Gly   Pro   His   Gly   Val   Pro   Gly   Pro
455               460                           465

His   Gly   Pro   Pro   Gly   Pro   Pro   Gly   Pro   Gly   Thr   Pro   Met
            470                     475                                 480

Gly   Pro   Tyr   Asn   Pro   Ala   Pro   Tyr   Asn   Pro   Gly   Pro   Pro
                        485                           490

Gly   Pro   Ala   Pro   His   Gly   Pro   Pro   Ala   Pro   Tyr   Ala   Pro
            495                     500                           505

Gln   Gly   Trp   Gly   Asn   Ala   Tyr   Pro   His   Trp   Gln   Gln   Gln
                  510                           515

Ala   Pro   Pro   Asp   Pro   Ala   Lys   Ala   Gly   Thr   Asp   Pro   Asn
520                           525                           530

Ser   Ala   Ala   Trp   Ala   Ala   Tyr   Tyr   Ala   His   Tyr   Tyr   Gln
            535                     540                                 545

Gln   Gln   Ala   Gln   Pro   Pro   Pro   Ala   Ala   Pro   Ala   Gly   Ala
                        550                           555

Pro   Thr   Thr   Thr   Gln   Thr   Asn   Gly   Gln   Gly   Asp   Gln   Gln
      560                           565                     570

Asn   Pro   Ala   Pro   Ala   Gly   Gln   Val   Asp   Tyr   Thr   Lys   Ala
                  575                     580

Trp   Glu   Glu   Tyr   Tyr   Lys   Lys   Met   Gly   Gln   Ala   Val   Pro
585                           590                           595

Ala   Pro   Thr   Gly   Ala   Pro   Pro   Gly   Gly   Gln   Pro   Asp   Tyr
            600                     605                                 610

Ser   Ala   Ala   Trp   Ala   Glu   His   Tyr   Arg   Gln   Gln   Ala   Ala
                  615                           620

Tyr   Tyr   Ala   Gln   Thr   Ser   Pro   Gln   Gly   Met   Pro   Gln   His
      625                     630                           635

Pro   Pro   Ala   Pro   Gln   Gly   Gln
                  640
```

( 2 ) INFORMATION FOR SEQ ID NO: 11:

( i ) SEQUENCE CHARACTERISTICS:
        ( A ) LENGTH: 33
        ( B ) TYPE: Nucleic acid
        ( C ) STRANDEDNESS: Double
        ( D ) TOPOLOGY: Unknown ( i i ) MOLECULE TYPE: DNA ( v i ) ORIGINAL SOURCE:
        ( A ) ORGANISM: Human ( i x ) FEATURE:
        ( D ) OTHER INFORMATION: FUSE
            oligonucleotide ( x i ) SEQUENCE DESCRIPTION: SEQ ID NO: 11:

GATCACAAAA TAAAAAATCC CGAGGGAATA TAG    33

( 2 ) INFORMATION FOR SEQ ID NO: 12:

( i ) SEQUENCE CHARACTERISTICS:
        ( A ) LENGTH: 33
        ( B ) TYPE: Nucleic acid
        ( C ) STRANDEDNESS: Double
        ( D ) TOPOLOGY: Unknown ( i i ) MOLECULE TYPE: DNA ( i i i ) HYPOTHETICAL: YES ( i x ) FEATURE:
    ( D ) OTHER INFORMATION: Mut A ( x i ) SEQUENCE DESCRIPTION: SEQ ID NO: 12:

GATCACAACT ACGTGCTAGG ACGCCGAATA TAG    33

( 2 ) INFORMATION FOR SEQ ID NO: 13:

( i ) SEQUENCE CHARACTERISTICS:
        ( A ) LENGTH: 39
        ( B ) TYPE: Nucleic acid
        ( C ) STRANDEDNESS: Double
        ( D ) TOPOLOGY: Unknown ( i i ) MOLECULE TYPE: DNA ( i i i ) HYPOTHETICAL: No ( i x ) FEATURE:
        ( D ) OTHER INFORMATION: cAMP response
            element ( x i ) SEQUENCE DESCRIPTION: SEQ ID NO: 13:

GATCTGACGT CATGACTGAC GTCATGACTG ACGTCATCA    39

( 2 ) INFORMATION FOR SEQ ID NO: 14:

( i ) SEQUENCE CHARACTERISTICS:
        ( A ) LENGTH: 32
        ( B ) TYPE: Nucleic acid
        ( C ) STRANDEDNESS: Double
        ( D ) TOPOLOGY: Unknown ( i i ) MOLECULE TYPE: DNA ( i i i ) HYPOTHETICAL: NO ( i x ) FEATURE:
        ( D ) OTHER INFORMATION: CT element in c-myc
            5'- flanking region ("CTE")

( x i ) SEQUENCE DESCRIPTION: SEQ ID NO: 14:

AATTCTCCTC CCCACCTTCC CCACCCTCCC CA    32

( 2 ) INFORMATION FOR SEQ ID NO: 15:

( i ) SEQUENCE CHARACTERISTICS:
        ( A ) LENGTH: 33
        ( B ) TYPE: Nucleic acid
        ( C ) STRANDEDNESS: Double
        ( D ) TOPOLOGY: Unknown ( i i ) MOLECULE TYPE: DNA ( i i i ) HYPOTHETICAL: YES ( i x ) FEATURE:
        ( D ) OTHER INFORMATION: Mut B ( x i ) SEQUENCE DESCRIPTION: SEQ ID NO: 15:

GATCACAAAA TAAAAAATGG ACGCCGAATA TAG    33

( 2 ) INFORMATION FOR SEQ ID NO: 16:

( i ) SEQUENCE CHARACTERISTICS:
        ( A ) LENGTH: 33
        ( B ) TYPE: Nucleic acid
        ( C ) STRANDEDNESS: Double
        ( D ) TOPOLOGY: Unknown ( i i ) MOLECULE TYPE: DNA (iii) HYPOTHETICAL: YES (ix) FEATURE:
(D) OTHER INFORMATION: Mut C (xi) SEQUENCE DESCRIPTION: SEQ ID NO: 16:

GATCACAACT ACGTGCTAGG CGAGGGAATA TAG    33

(2) INFORMATION FOR SEQ ID NO: 17:

(i) SEQUENCE CHARACTERISTICS:
(A) LENGTH: 9
(B) TYPE: Amino Acid
(C) STRANDEDNESS: Single
(D) TOPOLOGY: Unknown (ii) MOLECULE TYPE: Peptide/Protein (iii) HYPOTHETICAL: No (xi) SEQUENCE DESCRIPTION: SEQ ID NO: 17:

Lys Glu Ile Glu Gln Lys Val Gln Glu
 1                   5

(2) INFORMATION FOR SEQ ID NO: 18:

(i) SEQUENCE CHARACTERISTICS:
(A) LENGTH: 12
(B) TYPE: Nucleic acid
(C) STRANDEDNESS: Double
(D) TOPOLOGY: Unknown (ii) MOLECULE TYPE: DNA (xi) SEQUENCE DESCRIPTION: SEQ ID NO: 18:

TTAGTTAACT AA    12

(2) INFORMATION FOR SEQ ID NO: 19:

(i) SEQUENCE CHARACTERISTICS:
(A) LENGTH: 6
(B) TYPE: Amino Acid
(C) STRANDEDNESS: Single
(D) TOPOLOGY: Unknown (ii) MOLECULE TYPE: Peptide/Protein (ix) FEATURE:
(D) OTHER INFORMATION: Mutant 2

(ix) SEQUENCE DESCRIPTION: SEQ ID NO: 19:

Ile Gly Ser Arg Ile Arg
 1                 5

(2) INFORMATION FOR SEQ ID NO: 20:

(i) SEQUENCE CHARACTERISTICS:
(A) LENGTH: 4
(B) TYPE: Amino Acid
(C) STRANDEDNESS: Single
(D) TOPOLOGY: Unknown (ii) MOLECULE TYPE: Peptide/Protein (ix) FEATURE:
(D) OTHER INFORMATION: Mutant 3

(xi) SEQUENCE DESCRIPTION: SEQ ID NO: 20:

Ile Arg Ile Arg
 1           5

(2) INFORMATION FOR SEQ ID NO: 21:

(i) SEQUENCE CHARACTERISTICS:
        (A) LENGTH: 5
        (B) TYPE: Amino Acid
        (C) STRANDEDNESS: Single
        (D) TOPOLOGY: Unknown (ii) MOLECULE TYPE: Peptide/Protein (ix) FEATURE:
        (D) OTHER INFORMATION: Mutant 4

(xi) SEQUENCE DESCRIPTION: SEQ ID NO: 21:

Pro Arg Ile Arg Glu
1               5

(2) INFORMATION FOR SEQ ID NO: 22:

(i) SEQUENCE CHARACTERISTICS:
        (A) LENGTH: 4
        (B) TYPE: Amino Acid
        (C) STRANDEDNESS: Single
        (D) TOPOLOGY: Unknown (ii) MOLECULE TYPE: Peptide/Protein (ix) FEATURE:
        (D) OTHER INFORMATION: Mutant 6

(xi) SEQUENCE DESCRIPTION: SEQ ID NO: 22:

Gly Ile Pro Arg
1               5

(2) INFORMATION FOR SEQ ID NO: 23:

(i) SEQUENCE CHARACTERISTICS:
        (A) LENGTH: 4
        (B) TYPE: Amino Acid
        (C) STRANDEDNESS: Single
        (D) TOPOLOGY: Unknown (ii) MOLECULE TYPE: Peptide/Protein (ix) FEATURE:
        (D) OTHER INFORMATION: Mutant 8

(xi) SEQUENCE DESCRIPTION: SEQ ID NO: 23:

Arg Asp Pro Ala
1               5

(2) INFORMATION FOR SEQ ID NO: 24:

(i) SEQUENCE CHARACTERISTICS:
        (A) LENGTH: 4
        (B) TYPE: Amino Acid
        (C) STRANDEDNESS: Single
        (D) TOPOLOGY: Unknown (ii) MOLECULE TYPE: Peptide/Protein (ix) FEATURE:
        (D) OTHER INFORMATION: Mutant 9

(xi) SEQUENCE DESCRIPTION: SEQ ID NO: 24:

Arg Gly Ser Gly
1               5

FUSE BINDING PROTEIN AND CDNA THEREFOR

FIELD OF THE INVENTION

The present invention relates to a novel human cDNA and the encoded protein which interacts with a cis-element activator, known as the FUSE binding protein. A novel DNA-binding regulator of c-myc expression ("DROME") was purified, and then proteolytically and chemically degraded to peptides. These peptides were separated by HPLC and the sequences of multiple peptides were determined. Using the information from the peptide sequence, specific oligonucleotide primers were synthesized and then used as primers for the polymerase chain reaction employing human cDNA as a template. The resulting products were cloned and sequenced, and shown to encode additional peptides of the DROME protein. These DNA segments were then employed as probes to screen multiple phage libraries in order to reconstruct a full length reading frame from several overlapping clones. This information allows the expression of a full length protein. As used herein, the terms DROME and FUSE binding protein ("FBP") are synonymous.

BACKGROUND OF THE INVENTION

The c-myc proto-oncogene plays a central role in normal cell proliferation and programmed cell death (Y. Shi, J. Glynn, L. Guilbert, T. Cotter, R. Bissonnette, and D. Green, "Role for c-myc in activation-induced apoptotic cell death in T cell hybridomas," Science, 257:212–214 (1992)) and its deregulation contributes to the formation of a variety of tumors. (J. M. Bishop, Annu. Rev. Biochem. 52,301–354 (1983); M. D. Cole, "The myc oncogene: its role in transformation and differentiation." Annu. Rev. Genet. 20, 361–384 (1986); S. Cory, Adv. Cancer Res. 47, 189–234 (1986)).

Down regulation of the c-myc proto-oncogene occurs in the human promonomyelocytic leukemia cell line HL60 and human monoblastic line, U937, upon induction of differentiation. (C. Dony, M. Kessel, and P. Gruss, Nature. 317, 636–639 (1985); L. E. Grosso, and H. C. Pitot, Cancer Res. 45, 847–850 (1985); T. Watanabe, E. Sariban, T. Mitchell, and D. Kufe, Biochem. Biophys. Res. Commun. 126, 999–1005 (1985); D. L. Bentley, and M. Groudine, Nature, 321, 702–706 (1986); D. Eick and G. W. Bornkamm, Nucleic Acids Res. 14, 8331–8346 (1986); T. Endo, and B. Nadal-Ginard, Mol. Cell. Biol. 6, 1412–1421 (1986)). This suppression of c-myc expression occurs by two mechanisms; within three hours there is a block to elongation which can be reversed by removal of the differentiation agent. Subsequently, transcriptional initiation ceases, coinciding with irreversible commitment to the differentiation pathway. (U. Siebenlist, P. Bressler, and K. Kelly, Mol. Cel. Biol. 8, 867–874 (1988)).

A Far Upstream Element ("FUSE") which is required for maximal transcription of c-myc, binds a factor (DROME or FUSE binding protein ("FBP")) which is present in extracts of undifferentiated cells, but disappears upon differentiation. (M. I. Avigan, B. Strober, and D. Levens, "A Far Upstream Element Stimulates c-myc Expression In Undifferentiated Leukemia Cells." J. Biol. Chem. 265, 18538–18545 (1990)). The disappearance of this binding activity occurs 24 hours after addition of the differentiation agent coinciding with the loss of initiation of c-myc transcription. The FUSE site differs from other described positive regulatory elements for myc in a number of ways. Despite its placement a long distance from the transcription start site (–1500 bp relative to the myc P1 promoter), the FUSE element will not act as a traditional enhancer; multiple copies inserted upstream of a heterologous promoter do not stimulate transcription in transection experiments. However, when the FUSE site is present with additional c-myc regulatory sequences, specific stimulation of the c-myc promoter is observed, indicating that FUSE works in concert with other myc elements. These features suggest that the factor binding to this site may act to stimulate transcription by an unusual mechanism.

SUMMARY OF THE INVENTION

The nucleotide sequence for a novel DNA-binding regulator of c-myc expression is provided, together with the amino acid sequence for the encoded protein. The protein interacts with an activator cis-element approximately 1500 basepairs 5' of the human c-myc gene promoter P1. The cDNA and variations thereof have the nucleotide sequences of SEQ ID NO:1, SEQ ID NO:5, SEQ ID NO:7 and SEQ ID NO:9, and the proteins have the amino acid sequences of SEQ ID NO:2, SEQ ID NO:6, SEQ ID NO:8 and SEQ ID NO:10.

With the given sequence for the cDNA and protein of the present invention, one may now study genetic abnormalities of c-myc expression, in addition to numerous other uses of the gene and encoded protein.

The gene encoding the DROME or FUSE binding protein is useful in the diagnosis of disease states. Specific nucleic acid probes derived from knowledge of the DROME sequence and genetic map for PCR or hybridization are useful to analyze mutations, translocations and other genetic derangements that are associated with abnormalities of DROME or c-myc expression. Because DROME is highly activated during T-cell stimulation, these probes are useful to analyze immune system abnormalities. The DROME probes are also useful to analyze a variety of physiologic and pathologic conditions.

Knowledge of the cDNA and genomic structures of DROME allows the construction of vectors which express DROME or which express anti-sense DROME sequence. Oligonucleotide and expression vector anti-sense approaches to block DROME expression are useful to modulate DROME expression in vivo, which results in therapeutic modification of the levels of expression of genes regulated by DROME. Such strategies are of therapeutic value to certain pathologic conditions or can be used to provide prophylactic or beneficial changes in DROME expression in pre-pathologic conditions. If genetic disorders can be ascribed to abnormalities of the DROME protein or its expression, then gene therapy for such disorders will be heavily dependent on the information and materials derived from the characterization of the DROME gene and its cDNA.

Expression of the DROME protein itself in prokaryotic and eukaryotic expression vectors is useful in several regards. The DROME protein or fragments thereof are useful as an immunogen to generate polyclonal and monoclonal antibodies which can then be used to detect and quantitate the DROME protein. The DROME protein itself is useful as a probe to identify and quantify proteins which interact with or modify DROME; similarly, if the DROME protein is immobilized as a ligand for larger scale operations, the DROME interacting or modifying molecules can be purified. All of these proteins can be employed singly or in combination together with existing technologies as assay kits to detect, quantitate and analyze DROME protein.

Structural analysis of the DROME protein has defined a new DNA binding motif composed of a unique repeating element followed by an amphipathic helix. Knowledge of these structural elements together with knowledge of the complete cDNA sequence permits the identification, cloning and characterization of the genes for related proteins and DROME homologs using hybridization based or PCR based methods.

Because proteins which share structural motifs often share biochemical properties as well as functional and physiological roles, it is expected that DROME homologs and other proteins with the newly defined DNA binding motif are also important regulators of cell growth and other cellular processes. The same approaches used to modify DROME expression by sense and anti-sense vectors and anti-sense oligonucleotides is applied to DROME homologs and proteins sharing the DROME DNA binding motif in order to alter cell growth and cellular properties. These proteins or fragments thereof, which are either DROME homologs or recognizable as DNA binding proteins because they possess the DNA binding motif described herein, are useful for the generation of antibodies and diagnostic kits to relate these molecules to cancer, genetic and other human maladies. These proteins, antibodies and kits are useful in the diagnosis, treatment and study of human diseases.

Similarly, altered forms of the protein, either due to post-translational modification or altered RNA processing resulting from altered splicing or other RNA modifications, are identified and characterized utilizing the protein, antibody and nucleic acid probes outlined above. Each of these new proteins and/or genes all related to DROME are then subjected to similar analyses.

DETAILED DESCRIPTION OF THE INVENTION

A 70 kilodalton (kd) FUSE binding protein (FBP) has been purified from undifferentiated HL60 cells, the protein eluted from an SDS acrylamide gel and the amino acid sequence of internal peptides determined. The peptide sequences enabled the design of oligonucleotide PCR primers used to amplify cDNA template prepared from undifferentiated U937 cell total RNA.

Reverse transcriptase-polymerase chain reaction (RT-PCR) was performed as described in D. Rappolee, A. Wang, D. Mark, and Z. Werb, *J. Cell. Biochem.* 39,1 (1989). In the RT step 5µg total U937 RNA, 1.5µg of random hexamer primers (Promega) and 20µMoles of each deoxynucleotide triphosphate (dNTP) were incubated in a 40µl reaction with Superscript Reverse Transcriptase (BRL) and the manufacturer's reaction buffer adjusted to 10 mM dithiothreitol at 45° C. for 1 hour. After ethanol precipitation and reconstitution in 40µl dH$_2$O, 2µl of the RT reaction products were used as template in a 50µl PCR reaction with 20 pMoles of each degenerate primer, 20 nMoles each dNTP, 1.5 units Amplitaq polymerase (Perkin Elmer Cetus) and the manufacturer's buffer adjusted to 7.5 mM MgCL$_2$. Samples were incubated through 25 cycles of 94° C., 55° C. and 72° C., 2 minutes at each temperature Two amplified products contained open reading frames encoding segments identical to peptide sequences from purified FBP confirming that the authentic cDNA had been obtained.

Figure 1A:
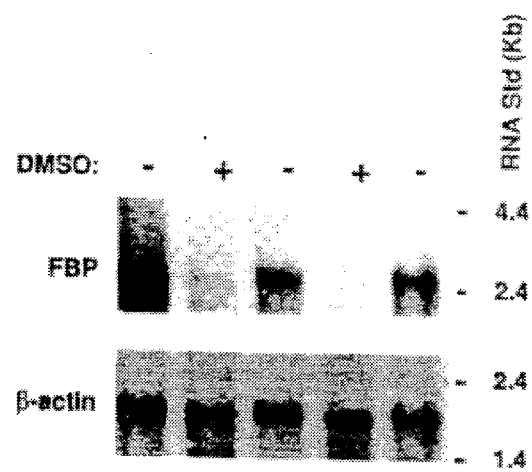
FIGS. 1A & B depict radiographs showing reduced expression over time of FBP mRNA.
Figure 1B:
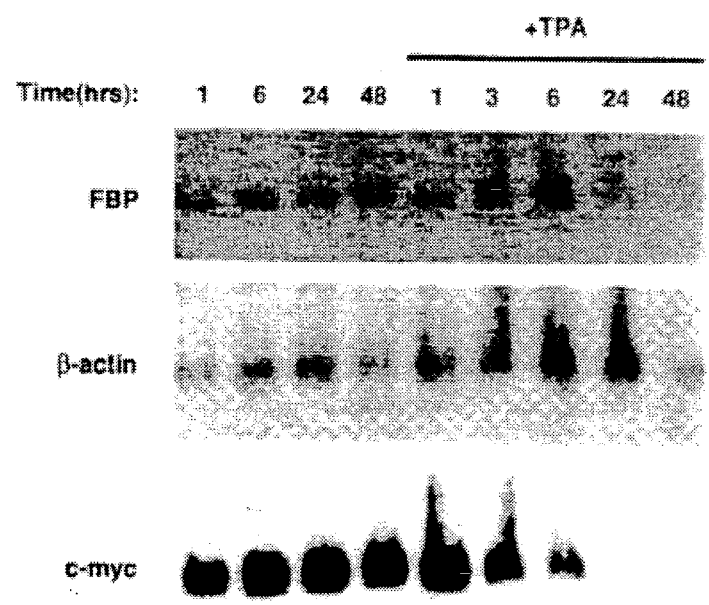

The PCR fragments hybridized to a single 2.6 kilobase (kb) RNA which disappeared after DMSO induced differentiation (FIG. 1A) consistent with the loss of FUSE binding activity after DMSO treatment. Polyadenylated RNA (10 µg) from cultured cells (J. M. Chirgwin et al., Biochemistry, 18, 5294 (1979)) was separated on a 1% agarose-formaldehyde gel, transferred to nitrocellulose and hybridized with a $^{32}$P probe from FBP, B-actin, or human c-myc cDNAs. FIG. 1A shows RNA prepared from HL60 cells grown 48 hrs. in the presence (+) or absence (−) of 1.3% Dimethyl Sulfoxide (DMSO) in RPMI medium supplemented with 10% fetal calf serum, glutamine, penicillin and streptomycin. FIG. 1B shows RNA prepared from HL60 cells cultured as indicated with or without 50 ng/ml 12-o-tetradecanohlphorbol 13-acetate (TPA) in the same medium as above.

As depicted in FIG. 1B, expression of the 2.6 kb transcript sharply declined after 24 hours of treatment with TPA and was undetectable at 48 hours paralleling: 1) the disappearance of the FUSE binding activity, 2) a dramatic decrease in c-myc transcriptional initiation and, 3) irreversible commitment to terminal differentiation. Hence, FBP mRNA and binding activity are shut off synchronously during differention.

A full length FBP cDNA sequence was assembled from overlapping clones obtained from three libraries using the PCR fragments as probes. All three cDNA libraries were prepared from poly A selected RNA and ligated into the lambda Zap II vector (Stratagene). Source RNAs were from undifferentiated HL60 cells, the B lymphoma cell line, BJAB, and PMA/PHA stimulated pooled human peripheral blood lymphocytes (PBLs).

Figure 2:
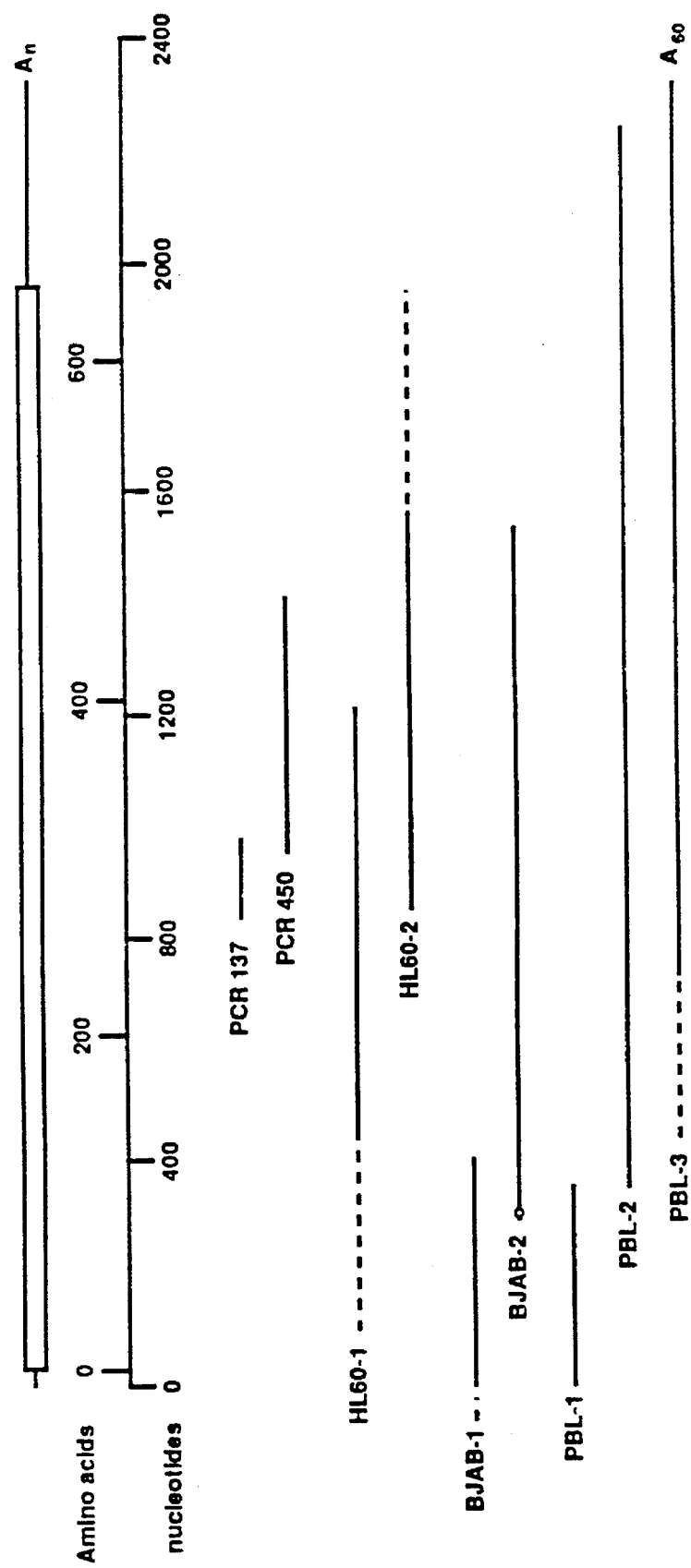
FIG. 2 gives the primary structure of DROME or FUSE binding protein (FBP) cDNA sequences.

The composite 2,384 bp cDNA contains 26 bp of 5' untranslated sequence, 1932 bp of open reading frame, and 426 bp of 3' untranslated including a poly A addition signal and 60 bp of poly A tail, as shown in FIG. 2.

The open box (FIG. 2) in the composite cDNA indicates the coding region, A$_n$ the poly A tail. The position of PCR products and clones are shown, solid lines represent vertically aligned identical sequence, dashed lines represent non-homologous sequence. Clone names at left indicate source or library of origin. The nonhomologous sequences in the HL60 clones, BJAB-1, and PBL-3 most likely are from reverse transcribed, unspliced pre-mRNA or extraneous cDNA fragments ligated together during the preparation of the libraries. The open circle on clone BJAB-2 indicates the position of the 3 base pair deletion. Dideoxy sequencing (Sequenase, U.S. Biochemical) followed the manufacturer's protocol.

The nucleic acid sequence (SEQ ID NO:1) of the full length cDNA is as follows:

| | | | | | | | | | | | | |
|---|---|---|---|---|---|---|---|---|---|---|---|---|
| GCGGCAGCGG<br>CGCCGTCGCC | | CTCTTATAGT<br>GAGAATATCA | | GCAACC<br>CGTTGG | ATG<br>TAC<br>Met<br>1 | GCA<br>CGT<br>Ala | GAC<br>CTG<br>Asp | TAT<br>ATA<br>Tyr | TCA<br>AGT<br>Ser<br>5 | ACA<br>TGT<br>Thr | | 44 |
| GTG<br>CAC<br>Val | CCT<br>GGA<br>Pro | CCC<br>GGG<br>Pro | CCC<br>GGG<br>Pro<br>10 | TCT<br>AGA<br>Ser | TCT<br>AGA<br>Ser | GGC<br>CCG<br>Gly | TCA<br>AGT<br>Ser | GCT<br>CGA<br>Ala<br>15 | GGT<br>CCA<br>Gly | GGC<br>CCG<br>Gly | GGT<br>CCA<br>Gly | GGT<br>CCA<br>Gly | 83 |
| GGC<br>CCG<br>Gly<br>20 | GGC<br>CCG<br>Gly | GGT<br>CCA<br>Gly | GGT<br>CCA<br>Gly | GGT<br>CCA<br>Gly | GGA<br>CCT<br>Gly<br>25 | GGA<br>CCT<br>Gly | GTT<br>CAA<br>Val | AAC<br>TTG<br>Asn | GAC<br>CTG<br>Asp | GCT<br>CGA<br>Ala<br>30 | TTC<br>AAG<br>Phe | AAA<br>TTT<br>Lys | 122 |
| GAT<br>CTA<br>Asp | GCA<br>CGT<br>Ala | CTG<br>GAC<br>Leu<br>35 | CAG<br>GTC<br>Gln | AGA<br>TCT<br>Arg | GCC<br>CGG<br>Ala | CGG<br>GCC<br>Arg | CAG<br>GTC<br>Gln<br>40 | ATT<br>TAA<br>Ile | GCA<br>CGT<br>Ala | GCA<br>CGT<br>Ala | AAA<br>TTT<br>Lys | ATT<br>TAA<br>Ile<br>45 | 161 |
| GGA<br>CCT<br>Gly | GGT<br>CCA<br>Gly | GAT<br>CTA<br>Asp | GCA<br>CGT<br>Ala | GGG<br>CCC<br>Gly<br>50 | ACA<br>TGT<br>Thr | TCA<br>AGT<br>Ser | CTG<br>GAC<br>Leu | AAT<br>TTA<br>Asn | TCA<br>AGT<br>Ser<br>55 | AAT<br>TTA<br>Asn | GAC<br>CTG<br>Asp | TAT<br>ATA<br>Tyr | 200 |
| GGT<br>CCA<br>Gly | TAT<br>ATA<br>Tyr<br>60 | GGG<br>CCC<br>Gly | GGA<br>CCT<br>Gly | CAA<br>GTT<br>Gln | AAA<br>TTT<br>Lys | AGA<br>TCT<br>Arg<br>65 | CCT<br>GGA<br>Pro | TTA<br>AAT<br>Leu | GAA<br>CTT<br>Glu | GAT<br>CTA<br>Asp | GGA<br>CCT<br>Gly<br>70 | GAT<br>CTA<br>Asp | 239 |
| CAA<br>GTT<br>Gln | CCA<br>GGT<br>Pro | GAT<br>CTA<br>Asp | GCT<br>CGA<br>Ala<br>75 | AAG<br>TTC<br>Lys | AAA<br>TTT<br>Lys | GTT<br>CAA<br>Val | GCT<br>CGA<br>Ala | CCT<br>GGA<br>Pro<br>80 | CAA<br>GTT<br>Gln | AAT<br>TTA<br>Asn | GAC<br>CTG<br>Asp | TCT<br>AGA<br>Ser | 278 |
| TTT<br>AAA<br>Phe<br>85 | GGA<br>CCT<br>Gly | ACA<br>TGT<br>Thr | CAG<br>GTC<br>Gln | TTA<br>AAT<br>Leu | CCA<br>GGT<br>Pro<br>90 | CCG<br>GGC<br>Pro | ATG<br>TAC<br>Met | CAT<br>GTA<br>His | CAG<br>GTC<br>Gln | CAG<br>GTC<br>Gln<br>95 | CAA<br>GTT<br>Gln | AGC<br>TCG<br>Ser | 317 |
| AGA<br>TCT<br>Arg | TCT<br>AGA<br>Ser | GTA<br>CAT<br>Val<br>100 | ATG<br>TAC<br>Met | ACA<br>TGT<br>Thr | GAA<br>CTT<br>Glu | GAA<br>CTT<br>Glu | TAC<br>ATG<br>Tyr<br>105 | AAA<br>TTT<br>Lys | GTT<br>CAA<br>Val | CCA<br>GGT<br>Pro | GAT<br>CTA<br>Asp | GGA<br>CCT<br>Gly<br>110 | 356 |
| ATG<br>TAC<br>Met | GTT<br>CAA<br>Val | GGA<br>CCT<br>Gly | TTC<br>AAG<br>Phe | ATA<br>TAT<br>Ile<br>115 | ATT<br>TAA<br>Ile | GGC<br>CCG<br>Gly | AGA<br>TCT<br>Arg | GGA<br>CCT<br>Gly | GGT<br>CCA<br>Gly<br>120 | GAA<br>CTT<br>Glu | CAG<br>GTC<br>Gln | ATC<br>TAG<br>Ile | 395 |
| TCA<br>AGT<br>Ser | CGC<br>GCG<br>Arg<br>125 | ATA<br>TAT<br>Ile | CAA<br>GTT<br>Gln | CAG<br>GTC<br>Gln | GAA<br>CTT<br>Glu | TCT<br>AGA<br>Ser<br>130 | GGA<br>CCT<br>Gly | TGC<br>ACG<br>Cys | AAA<br>TTT<br>Lys | ATA<br>TAT<br>Ile | CAG<br>GTC<br>Gln<br>135 | ATA<br>TAT<br>Ile | 434 |
| GCT<br>CGA<br>Ala | CCT<br>GGA<br>Pro | GAC<br>CTG<br>Asp | AGT<br>TCA<br>Ser<br>140 | GGT<br>CCA<br>Gly | GGC<br>CCG<br>Gly | CTT<br>GAA<br>Leu | CCA<br>GGT<br>Pro | GAA<br>CTT<br>Glu<br>145 | AGG<br>TCC<br>Arg | TCC<br>AGG<br>Ser | TGT<br>ACA<br>Cys | ATG<br>TAC<br>Met | 473 |
| TTA<br>AAT<br>Leu<br>150 | ACT<br>TGA<br>Thr | GGA<br>CCT<br>Gly | ACA<br>TGT<br>Thr | CCT<br>GGA<br>Pro | GAA<br>CTT<br>Glu<br>155 | TCT<br>AGA<br>Ser | GTC<br>CAG<br>Val | CAG<br>GTC<br>Gln | TCA<br>AGT<br>Ser | GCA<br>CGT<br>Ala<br>160 | AAA<br>TTT<br>Lys | CGG<br>GCC<br>Arg | 512 |
| TTA<br>AAT<br>Leu | CTG<br>GAC<br>Leu | GAC<br>CTG<br>Asp<br>165 | CAG<br>GTC<br>Gln | ATT<br>TAA<br>Ile | GTT<br>CAA<br>Val | GAA<br>CTT<br>Glu | AAA<br>TTT<br>Lys<br>170 | GGA<br>CCT<br>Gly | AGA<br>TCT<br>Arg | CCA<br>GGT<br>Pro | GCT<br>CGA<br>Ala | CCT<br>GGA<br>Pro<br>175 | 551 |
| GGC<br>CCG<br>Gly | TTC<br>AAG<br>Phe | CAT<br>GTA<br>His | CAT<br>GTA<br>His | GGC<br>CCG<br>Gly<br>180 | GAT<br>CTA<br>Asp | GGA<br>CCT<br>Gly | CCG<br>GGC<br>Pro | GGA<br>CCT<br>Gly | AAT<br>TTA<br>Asn<br>185 | GCA<br>CGT<br>Ala | GTT<br>CAA<br>Val | CAA<br>GTT<br>Gln | 590 |
| GAA<br>CTT<br>Glu | ATC<br>TAG<br>Ile<br>190 | ATG<br>TAC<br>Met | ATT<br>TAA<br>Ile | CCA<br>GGT<br>Pro | GCT<br>CGA<br>Ala | AGC<br>TCG<br>Ser<br>195 | AAG<br>TTC<br>Lys | GCA<br>CGT<br>Ala | GGA<br>CCT<br>Gly | TTA<br>AAT<br>Leu | GTC<br>CAG<br>Val<br>200 | ATT<br>TAA<br>Ile | 629 |

| | | | | | | | | | | | | | |
|---|---|---|---|---|---|---|---|---|---|---|---|---|---|
| GGA | AAA | GGG | GGA | GAA | ACT | ATT | AAA | CAG | CTT | CAG | GAA | CGG | 668 |
| CCT | TTT | CCC | CCT | CTT | TGA | TAA | TTT | GTC | GAA | GTC | CTT | GCC | |
| Gly | Lys | Gly | Gly | Glu | Thr | Ile | Lys | Gln | Leu | Gln | Glu | Arg | |
| | | | 205 | | | | 210 | | | | | | |
| GCT | GGA | GTT | AAA | ATG | GTT | ATG | ATT | CAA | GAC | GGG | CCG | CAG | 707 |
| CGA | CCT | CAA | TTT | TAC | CAA | TAC | TAA | GTT | CTG | CCC | GGC | GTC | |
| Ala | Gly | Val | Lys | Met | Val | Met | Ile | Gln | Asp | Gly | Pro | Gln | |
| 215 | | | | | 220 | | | | | 225 | | | |
| AAC | ACT | GGT | GCT | GAC | AAA | CCT | CTT | AGG | ATT | ACA | GGA | GAC | 746 |
| TTG | TGA | CCA | CGA | CTG | TTT | GGA | GAA | TCC | TAA | TGT | CCT | CTG | |
| Asn | Thr | Gly | Ala | Asp | Lys | Pro | Leu | Arg | Ile | Thr | Gly | Asp | |
| | | 230 | | | | | 235 | | | | | 240 | |
| CCA | TAT | AAA | GTT | CAA | CAA | GCC | AAG | GAA | ATG | GTG | TTA | GAG | 785 |
| GGT | ATA | TTT | CAA | GTT | GTT | CGG | TTC | CTT | TAC | CAC | AAT | CTC | |
| Pro | Tyr | Lys | Val | Gln | Gln | Ala | Lys | Glu | Met | Val | Leu | Glu | |
| | | | | 245 | | | | | 250 | | | | |
| TTA | ATT | CGT | GAT | CAA | GGC | GGT | TTC | AGA | GAA | GTT | CGG | AAT | 824 |
| AAT | TAA | GCA | CTA | GTT | CCG | CCA | AAG | TCT | CTT | CAA | GCC | TTA | |
| Leu | Ile | Arg | Asp | Gln | Gly | Gly | Phe | Arg | Glu | Val | Arg | Asn | |
| | 255 | | | | | 260 | | | | | 265 | | |
| GAG | TAT | GGG | TCA | AGA | ATA | GGA | GGA | AAT | GAA | GGG | ATA | GAT | 863 |
| CTC | ATA | CCC | AGT | TCT | TAT | CCT | CCT | TTA | CTT | CCC | TAT | CTA | |
| Glu | Tyr | Gly | Ser | Arg | Ile | Gly | Gly | Asn | Glu | Gly | Ile | Asp | |
| | | | 270 | | | | | 275 | | | | | |
| GTC | CCC | ATT | CCA | AGA | TTT | GCT | GTT | GGC | ATT | GTA | ATA | GGA | 902 |
| CAG | GGG | TAA | GGT | TCT | AAA | CGA | CAA | CCG | TAA | CAT | TAT | CCT | |
| Val | Pro | Ile | Pro | Arg | Phe | Ala | Val | Gly | Ile | Val | Ile | Gly | |
| 280 | | | | | 285 | | | | | 290 | | | |
| AGA | AAT | GGA | GAG | ATG | ATC | AAA | AAA | ATA | CAA | AAT | GAT | GCT | 941 |
| TCT | TTA | CCT | CTC | TAC | TAG | TTT | TTT | TAT | GTT | TTA | CTA | CGA | |
| Arg | Asn | Gly | Glu | Met | Ile | Lys | Lys | Ile | Gln | Asn | Asp | Ala | |
| | | 295 | | | | | 300 | | | | | 305 | |
| GGT | GTT | CGC | ATT | CAG | TTT | AAG | CCA | GAT | GAT | GGG | ACA | ACA | 980 |
| CCA | CAA | GCG | TAA | GTC | AAA | TTC | GGT | CTA | CTA | CCC | TGT | TGT | |
| Gly | Val | Arg | Ile | Gln | Phe | Lys | Pro | Asp | Asp | Gly | Thr | Thr | |
| | | | | 310 | | | | | 315 | | | | |
| CCC | GAA | AGG | ATA | GCA | CAA | ATA | ACA | GGA | CCT | CCA | GAC | CGA | 1019 |
| GGG | CTT | TCC | TAT | CGT | GTT | TAT | TGT | CCT | GGA | GGT | CTG | GCT | |
| Pro | Glu | Arg | Ile | Ala | Gln | Ile | Thr | Gly | Pro | Pro | Asp | Arg | |
| | 320 | | | | | 325 | | | | | 330 | | |
| TGT | CAA | CAT | GCT | GCA | GAA | ATT | ATT | ACA | GAC | CTT | CTT | CGA | 1058 |
| ACA | GTT | GTA | CGA | CGT | CTT | TAA | TAA | TGT | CTG | GAA | GAA | GCT | |
| Cys | Gln | His | Ala | Ala | Glu | Ile | Ile | Thr | Asp | Leu | Leu | Arg | |
| | | | 335 | | | | | 340 | | | | | |
| AGT | GTT | CAG | GCT | GGT | AAT | CCT | GGT | GGA | CCT | GGA | CCT | GGT | 1097 |
| TCA | CAA | GTC | CGA | CCA | TTA | GGA | CCA | CCT | GGA | CCT | GGA | CCA | |
| Ser | Val | Gln | Ala | Gly | Asn | Pro | Gly | Gly | Pro | Gly | Pro | Gly | |
| 345 | | | | | 350 | | | | | 355 | | | |
| GGT | CGA | GGA | AGA | GGT | AGA | GGT | CAA | GGC | AAC | TGG | AAC | ATG | 1136 |
| CCA | GCT | CCT | TCT | CCA | TCT | CCA | GTT | CCG | TTG | ACC | TTG | TAC | |
| Gly | Arg | Gly | Arg | Gly | Arg | Gly | Gln | Gly | Asn | Trp | Asn | Met | |
| | | 360 | | | | | 365 | | | | | 370 | |
| GGA | CCA | CCT | GGT | GGA | TTA | CAG | GAA | TTT | AAT | TTT | ATT | GTG | 1175 |
| CCT | GGT | GGA | CCA | CCT | AAT | GTC | CTT | AAA | TTA | AAA | TAA | CAC | |
| Gly | Pro | Pro | Gly | Gly | Leu | Gln | Glu | Phe | Asn | Phe | Ile | Val | |
| | | | | 375 | | | | | 380 | | | | |
| CCA | ACT | GGG | AAA | ACT | GGA | TTA | ATA | ATA | GGA | AAA | GGA | GGT | 1214 |
| GGT | TGA | CCC | TTT | TGA | CCT | AAT | TAT | TAT | CCT | TTT | CCT | CCA | |
| Pro | Thr | Gly | Lys | Thr | Gly | Leu | Ile | Ile | Gly | Lys | Gly | Gly | |
| | 385 | | | | | 390 | | | | | 395 | | |
| GAA | ACC | ATA | AAA | AGC | ATA | AGC | CAG | CAG | TCT | GGT | GCA | AGA | 1253 |
| CTT | TGG | TGT | TTT | TCG | TAT | TCG | GTC | GTC | AGA | CCA | CGT | TCT | |
| Glu | Thr | Ile | Lys | Ser | Ile | Ser | Gln | Gln | Ser | Gly | Ala | Arg | |
| | | | 400 | | | | | 405 | | | | | |

| | | | | | | | | | | | | | |
|---|---|---|---|---|---|---|---|---|---|---|---|---|---|
| ATA | GAA | CTT | CAG | AGA | AAT | CCT | CCA | CCA | AAT | GCA | GAT | CCT | 1292 |
| TAT | CTT | GAA | GTC | TCT | TTA | GGA | GGT | GGT | TTA | CGT | CTA | GGA | |
| Ile | Glu | Leu | Gln | Arg | Asn | Pro | Pro | Pro | Asn | Ala | Asp | Pro | |
| 410 | | | | | 415 | | | | | 420 | | | |
| AAT | ATG | AAG | TTA | TTT | ACA | ATT | CGT | GGC | ACT | CCA | CAA | CAG | 1331 |
| TTA | TAC | TTC | AAT | AAA | TGT | TAA | GCA | CCG | TGA | GGT | GTT | GTC | |
| Asn | Met | Lys | Leu | Phe | Thr | Ile | Arg | Gly | Thr | Pro | Gln | Gln | |
| | | 425 | | | | | 430 | | | | | 435 | |
| ATA | GAC | TAT | GCT | CGG | CAA | CTC | ATA | GAA | GAA | AAG | ATT | GGT | 1370 |
| TAT | CTG | ATA | CGA | GCC | GTT | GAG | TAT | CTT | CTT | TTC | TAA | CCA | |
| Ile | Asp | Tyr | Ala | Arg | Gln | Leu | Ile | Glu | Glu | Lys | Ile | Gly | |
| | | | | 440 | | | | | 445 | | | | |
| GGC | CCA | GTA | AAT | CCT | TTA | GGG | CCA | CCT | GTA | CCC | CAT | GGG | 1409 |
| CCG | GGT | CAT | TTA | GGA | AAT | CCC | GGT | GGA | CAT | GGG | GTA | CCC | |
| Gly | Pro | Val | Asn | Pro | Leu | Gly | Pro | Pro | Val | Pro | His | Gly | |
| | 450 | | | | | 455 | | | | | 460 | | |
| CCC | CAT | GGT | GTC | CCA | GGC | CCC | CAT | GGA | CCT | CCT | GGG | CCT | 1448 |
| GGG | GTA | CCA | CAG | GGT | CCG | GGG | GTA | CCT | GGA | GGA | CCC | GGA | |
| Pro | His | Gly | Val | Pro | Gly | Pro | His | Gly | Pro | Pro | Gly | Pro | |
| | | | 465 | | | | | 470 | | | | | |
| CCA | GGG | CCT | GGA | ACT | CCA | ATG | GGA | CCA | TAC | AAC | CCT | GCA | 1487 |
| GGT | CCC | GGA | CCT | TGA | GGT | TAC | CCT | GGT | ATG | TTG | GGA | CGT | |
| Pro | Gly | Pro | Gly | Thr | Pro | Met | Gly | Pro | Tyr | Asn | Pro | Ala | |
| 475 | | | | | 480 | | | | | 485 | | | |
| CCT | TAT | AAT | CCT | GGA | CCA | CCA | GGC | CCG | GCT | CCT | CAT | GGT | 1526 |
| GGA | ATA | TTA | GGA | CCT | GGT | GGT | CCG | GGC | CGA | GGA | GTA | CCA | |
| Pro | Tyr | Asn | Pro | Gly | Pro | Pro | Gly | Pro | Ala | Pro | His | Gly | |
| | | 490 | | | | | 495 | | | | | 500 | |
| CCT | CCA | GCC | CCA | TAT | GCT | CCC | CAG | GGA | TGG | GGA | AAT | GCA | 1565 |
| GGA | GGT | CGG | GGT | ATA | CGA | GGG | GTC | CCT | ACC | CCT | TTA | CGT | |
| Pro | Pro | Ala | Pro | Tyr | Ala | Pro | Gln | Gly | Trp | Gly | Asn | Ala | |
| | | | | 505 | | | | | 510 | | | | |
| TAT | CCA | CAC | TGG | CAG | CAG | CAG | GCT | CCT | CCT | GAT | CCA | GCT | 1604 |
| ATA | GGT | GTG | ACC | GTC | GTC | GTC | CGA | GGA | GGA | CTA | GGT | CGA | |
| Tyr | Pro | His | Trp | Gln | Gln | Gln | Ala | Pro | Pro | Asp | Pro | Ala | |
| | 515 | | | | | 520 | | | | | 525 | | |
| AAG | GCA | GGA | ACG | GAT | CCA | AAT | TCA | GCA | GCT | TGG | GCT | GCT | 1643 |
| TTC | CGT | CCT | TGC | CTA | GGT | TTA | AGT | CGT | CGA | ACC | CGA | CGA | |
| Lys | Ala | Gly | Thr | Asp | Pro | Asn | Ser | Ala | Ala | Trp | Ala | Ala | |
| | | | 530 | | | | | 535 | | | | | |
| TAT | TAC | GCT | CAC | TAT | TAT | CAA | CAG | CAA | GCA | CAG | CCA | CCA | 1682 |
| ATA | ATG | CGA | GTG | ATA | ATA | GTT | GTC | GTT | CGT | GTC | GGT | GGT | |
| Tyr | Tyr | Ala | His | Tyr | Tyr | Gln | Gln | Gln | Ala | Gln | Pro | Pro | |
| 540 | | | | | 545 | | | | | 550 | | | |
| CCA | GCA | GCC | CCT | GCA | GGT | GCA | CCA | ACT | ACA | ACT | CAA | ACT | 1721 |
| GGT | CGT | CGG | GGA | CGT | CCA | CGT | GGT | TGA | TGT | TGA | GTT | TGA | |
| Pro | Ala | Ala | Pro | Ala | Gly | Ala | Pro | Thr | Thr | Thr | Gln | Thr | |
| | | 555 | | | | | 560 | | | | | 565 | |
| AAT | GGA | CAA | GGA | GAT | CAG | CAG | AAT | CCA | GCC | CCA | GCT | GGA | 1760 |
| TTA | CCT | GTT | CCT | CTA | GTC | GTC | TTA | GGT | CGG | GGT | CGA | CCT | |
| Asn | Gly | Gln | Gly | Asp | Gln | Gln | Asn | Pro | Ala | Pro | Ala | Gly | |
| | | | | 570 | | | | | 575 | | | | |
| CAG | GTT | GAT | TAT | ACC | AAG | GCT | TGG | GAA | GAG | TAC | TAC | AAG | 1799 |
| GTC | CAA | CTA | ATA | TGG | TTC | CGA | ACC | CTT | CTC | ATG | ATG | TTC | |
| Gln | Val | Asp | Tyr | Thr | Lys | Ala | Trp | Glu | Glu | Tyr | Tyr | Lys | |
| | 580 | | | | | 585 | | | | | 590 | | |
| AAA | ATG | GGT | CAG | GCA | GTT | CCT | GCT | CCG | ACT | GGG | GCT | CCT | 1838 |
| TTT | TAC | CCA | GTC | CGT | CAA | GGA | CGA | GGC | TGA | CCC | CGA | GGA | |
| Lys | Met | Gly | Gln | Ala | Val | Pro | Ala | Pro | Thr | Gly | Ala | Pro | |
| | | | 595 | | | | | 600 | | | | | |
| CCA | GGT | GGT | CAG | CCA | GAT | TAT | AGT | GCA | GCC | TGG | GCT | GAG | 1877 |
| GGT | CCA | CCA | GTC | GGT | CTA | ATA | TCA | CGT | CGG | ACC | CGA | CTC | |
| Pro | Gly | Gly | Gln | Pro | Asp | Tyr | Ser | Ala | Ala | Trp | Ala | Glu | |
| 605 | | | | | 610 | | | | | 615 | | | |

| | | | | | | | | | | | | | |
|---|---|---|---|---|---|---|---|---|---|---|---|---|---|
| CAT | TAT | AGA | CAA | CAA | GCA | GCC | TAT | TAT | GCC | CAG | ACA | AGT | 1916 |
| GTA | ATA | TCT | GTT | GTT | CGT | CGG | ATA | ATA | CGG | GTC | TGT | TCA | |
| His | Tyr | Arg | Gln | Gln | Ala | Ala | Tyr | Tyr | Ala | Gln | Thr | Ser | |
| | | 620 | | | | | 625 | | | | | 630 | |
| CCC | CAG | GGA | ATG | CCA | CAG | CAT | CCT | CCA | GCA | CCT | CAG | GGC | 1955 |
| GGG | GTC | CCT | TAC | GGT | GTC | GTA | GGA | GGT | CGT | GGA | GTC | CCG | |
| Pro | Gln | Gly | Met | Pro | Gln | His | Pro | Pro | Ala | Pro | Gln | Gly | |
| | | | | 635 | | | | | 640 | | | | |
| CAA | TAA | TAA | GAAGTGGACA | | ATACAGTATT | | TGCTTCATTG | | | | | | 1994 |
| GTT | ATT | ATT | CTTCACCTGT | | TATGTCATAA | | ACGAAGTAAC | | | | | | |
| Gln | | | | | | | | | | | | | |

| | | | | |
|---|---|---|---|---|
| TGTGGGGGAA | AAAAACCTTT | GTTAAATATA | TGGATGCAGA | 2034 |
| ACACCCCCTT | TTTTTGGAAA | CAATTTATAT | ACCTACGTCT | |
| CGACTTGATG | AAGATCTTAA | TTTTGTTTTT | GGTTTAAAAT | 2074 |
| GCTGAACTAC | TTCTAGAATT | AAAACAAAAA | CCAAATTTTA | |
| AGTGTTTCCT | TTTTTTTTTT | TTTTTTTTTG | AAAATGTACA | 2114 |
| TCACAAGGA | AAAAAAAAAA | AAAAAAAAAC | TTTTACATGT | |
| AAATATCTAT | CACTACTGAT | AGGAGGTTAA | TATTTCTGTG | 2154 |
| TTTATAGATA | GTGATGACTA | TCCTCCAATT | ATAAAGACAC | |
| TAGAAATGAA | AATTGGTTTG | TTTTTAGTAT | TTAGTGTAGA | 2194 |
| ATCTTTACTT | TTAACCAAAC | AAAAATCATA | AATCACATCT | |
| TGTACACATT | CCAGCAAATG | TATTTGCAAT | TATGTGGTTG | 2234 |
| ACATGTGTAA | GGTCGTTTAC | ATAAACGTTA | ATACACCAAC | |
| ATGCTTTGTG | ATATAAATGT | ACTTTTTCAA | TGTATACTTT | 2274 |
| TACGAAACAC | TATATTTACA | TGAAAAAGTT | ACATATGAAA | |
| CACTTTCCAA | ATGCCTGTTT | TGTGCTTTAC | AATAAATGAT | 2314 |
| GTGAAAGGTT | TACGGACAAA | ACACGAAATG | TTATTTACTA | |
| ATGAAACCTC | AAAAAAAAAA | AAAAAAAAAA | AAAAAAAAAA | 2354 |
| TACTTTGGAG | TTTTTTTTTT | TTTTTTTTTT | TTTTTTTTTT | |
| AAAAAAAAAA | AAAAAAAAAA | AAAAAAAAAA | | 2384 |
| TTTTTTTTTT | TTTTTTTTTT | TTTTTTTTTT | | |

Three clones from a BJAB cDNA library and three clones from an activated, human peripheral blood lymphocyte cDNA library contain the above sequence. Three clones from the same BJAB library and two clones from the activated lymphocyte library are lacking nucleotides 316, 317 and 318 (SEQ ID NO:9). The mRNA lacking these three nucleotides would encode a variant protein lacking serine (SEQ ID NO:10).

Though the 5' untranslated region of the message appears to be unusually short and contains no in-frame stop codons, the initiator methionine is contained in a nine out of ten match with the Kozak consensus. (M. Kozak, "Structural features in eukaryotic mRNAs that modulate the initiation of translation". *J. Biol. Chem.* 266(30), 19867–19870 (1991)). The deduced polypeptide, 644 amino acids in length, has a calculated molecular weight of 67.5kd consistent with the molecular weight of the purified protein. The amino acid sequence can be found in SEQ ID NO:2.

To create the full length cDNA, pools of degenerate oligonucleotides were synthesized to correspond to the amino acid sequence of the peptide encoded by nucleotides 843 to 860 and used as primers in a PCR reaction. The oligo sequences (SEQ ID NO:3) are:

5'-CAGAATTCGGIGGIAAYGARGGIANCG-3' where I indicates an inosine residue, and Y is either T or C, R is either A or G, and N is either I or T.

Degenerate oligonucleotides were also synthesized to correspond to the peptide encoded by nucleotides 957 to 971 and used together with the above primer (SEQ ID NO:3) in a PCR reaction which amplified the PCR product encoded by nucleotides 861 to 956 from human cDNA. The sequences (SEQ ID NO:4) of this degenerate oligo pool are:

5'-GAGTCGACRTCRTCRTCIGGYTTRAA-3' where R is either A or G, and Y is either C or T.

The full length cDNA sequence has features which suggest multiple modes of FBP regulation. There is an unusual codon bias. For every amino acid with a degenerate codon, except glutamine, the FBP sequence avoids the codons preferred in a survey of 2,681 human genes (K-n. Wada, Y. Wada, F. Ishibashi, T. Gojobori and T. Ikemura. Codon usage tabulated from the GenBank genetic sequence data. *Nucleic Acids Res.* 20(supplement), 2111–2118 (1992)) suggesting translational regulation. The existence of alternate isoforms of FBP generated by regulation of RNA processing is suggested by multiple independent clones, half of which exhibit a precise deletion of 3 nucleotides at basepair 316, 317 and 318, removing serine 97 (see FIG. 2B). The surrounding sequence is consistent with an alternate splice acceptor site (S. M. Mount, *Nuc. Acids Res.* 10,459 (1982)) which could generate this deletion.

Other variations of the cDNA sequence and encoded protein were found in separate clones. In a clone labeled "25-1" an A residue was found at nucleic acid position 473, which resulted in a complementary base T and a codon specifying an isoleucine at amino acid 149.

The clone from an HL60 cDNA library labeled "3-1" contains 10 basepairs of 5' untranslated sequence, followed by an open reading frame comprised of the nucleotides from position 858 to position 1561 shown above in SEQ ID NO:1 and a unique 3' end cDNA sequence of 25 base pairs, followed by two adjacent stop codons and additional 3' untranslated sequence. The sequence of clone 3-1 is as follows (SEQ ID NO: 5):

| | | | | | | | | | | | | |
|---|---|---|---|---|---|---|---|---|---|---|---|---|
| GGAATTCCGG CCTTAAGGCC | ATA TAT Ile 1 | GAT CTA Asp | GTC CAG Val | CCC GGG Pro | ATT TAA Ile 5 | CCA GGT Pro | AGA TCT Arg | TTT AAA Phe | GCT CGA Ala | GTT CAA Val 10 | | 40 |
| GGC CCG Gly | ATT TAA Ile | GTA CAT Val | ATA TAT Ile | GGA CCT Gly 15 | AGA TCT Arg | AAT TTA Asn | GGA CCT Gly | GAG CTC Glu | ATG TAC Met 20 | ATC TAG Ile | AAA TTT Lys | AAA TTT Lys | 79 |
| ATA TAT Ile | CAA GTT Gln 25 | AAT TTA Asn | GAT CTA Asp | GCT CGA Ala | GGT CCA Gly | GTT CAA Val 30 | CGC GCG Arg | ATT TAA Ile | CAG GTC Gln | TTT AAA Phe | AAG TTC Lys 35 | CCA GGT Pro | 118 |
| GAT CTA Asp | GAT CTA Asp | GGG CCC Gly | ACA TGT Thr 40 | ACA TGT Thr | CCC GGG Pro | GAA CTT Glu | AGG TCC Arg | ATA TAT Ile 45 | GCA CGT Ala | CAA GTT Gln | ATA TAT Ile | ACA TGT Thr | 157 |
| GGA CCT Gly 50 | CCT GGA Pro | CCA GGT Pro | GAC CTG Asp | CGA GCT Arg | TGT ACA Cys 55 | CAA GTT Gln | CAT GTA His | GCT CGA Ala | GCA CGT Ala | GAA CTT Glu 60 | ATT TAA Ile | ATT TAA Ile | 196 |
| ACA TGT Thr | GAC CTG Asp | CTT GAA Leu 65 | CTT GAA Leu | CGA GCT Arg | AGT TCA Ser | GTT CAA Val | CAG GTC Gln 70 | GCT CGA Ala | GGT CCA Gly | AAT TTA Asn | CCT GGA Pro | GGT CCA Gly 75 | 235 |
| GGA CCT Gly | CCT GGA Pro | GGA CCT Gly | CCT GGA Pro | GGT CCA Gly 80 | GGT CCA Gly | CGA GCT Arg | GGA CCT Gly | AGA TCT Arg | GGT CCA Gly 85 | AGA TCT Arg | GGT CCA Gly | CAA GTT Gln | 274 |
| GGC CCG Gly | AAC TTG Asn 90 | TGG ACC Trp | AAC TTG Asn | ATG TAC Met | GGA CCT Gly | CCA GGT Pro 95 | CCT GGA Pro | GGT CCA Gly | GGA CCT Gly | TTA AAT Leu | CAG GTC Gln 100 | GAA CTT Glu | 313 |
| TTT AAA Phe | AAT TTA Asn | TTT AAA Phe | ATT TAA Ile 105 | GTG CAC Val | CCA GGT Pro | ACT TGA Thr | GGG CCC Gly | AAA TTT Lys 110 | ACT TGA Thr | GGA CCT Gly | TTA AAT Leu | ATA TAT Ile | 352 |
| ATA TAT Ile 115 | GGA CCT Gly | AAA TTT Lys | GGA CCT Gly | GGT CCA Gly | GAA CTT Glu 120 | ACC TGG Thr | ATA TAT Ile | AAA TTT Lys | AGC TCG Ser | ATA TAT Ile 125 | AGC TCG Ser | CAG GTC Gln | 391 |
| CAG GTC Gln | TCT AGA Ser | GGT CCA Gly 130 | GCA CGT Ala | AGA TCT Arg | ATA TAT Ile | GAA CTT Glu | CTT GAA Leu 135 | CAG GTC Gln | AGA TCT Arg | AAT TTA Asn | CCT GGA Pro | CCA GGT Pro 140 | 430 |
| CCA GGT Pro | AAT TTA Asn | GCA CGT Ala | GAT CTA Asp | CCT GGA Pro 145 | AAT TTA Asn | ATG TAC Met | AAG TTC Lys | TTA AAT Leu | TTT AAA Phe 150 | ACA TGT Thr | ATT TAA Ile | CGT GCA Arg | 469 |
| GGC CCG Gly | ACT TGA Thr 155 | CCA GGT Pro | CAA GTT Gln | CAG GTC Gln | ATA TAT Ile | GAC CTG Asp 160 | TAT ATA Tyr | GCT CGA Ala | CGG GCC Arg | CAA GTT Gln | CTC GAG Leu 165 | ATA TAT Ile | 508 |
| GAA CTT Glu | GAA CTT Glu | AAG TTC Lys | ATT TAA Ile 170 | GGT CCA Gly | GGC CCG Gly | CCA GGT Pro | GTA CAT Val | AAT TTA Asn 175 | CCT GGA Pro | TTA AAT Leu | GGG CCC Gly | CCA GGT Pro | 547 |
| CCT GGA Pro 180 | GTA CAT Val | CCC GGG Pro | CAT GTA His | GGG CCC Gly | CCC GGG Pro 185 | CAT GTA His | GGT CCA Gly | GTC CAG Val | CCA GGT Pro | GGC CCG Gly 190 | CCC GGG Pro | CAT GTA His | 586 |
| GGA CCT Pro | CCT GGA | CCT GGA | GGG CCC | CCT GGA | CCA GGT | GGG CCC | CCT GGA | GGA CCT | ACT TGA | CCA GGT | ATG TAC | GGA CCT | 625 |

| | | | | | | | | | | | | |
|---|---|---|---|---|---|---|---|---|---|---|---|---|
| CCT Gly | GGA Pro 195 | GGA Pro | CCC Gly | GGA Pro | GGT Pro | CCC Gly | GGA Pro 200 | CCT Gly | TGA Thr | GGT Pro | TAC Met | CCT Gly 205 | |
| CCA GGT Pro | TAC ATG Tyr | AAC TTG Asn | CCT GGA Pro | GCA CGT Ala 210 | CCT GGA Pro | TAT ATA Tyr | AAT TTA Asn | CCT GGA Pro | GGA CCT Gly 215 | CCA GGT Pro | CCA GGT Pro | GGC CCG Gly | 664 |
| CCG GGC Pro | GCT CGA Ala 220 | CCT GGA Pro | CAT GTA His | GGT CCA Gly | CCT GGA Pro | CCA GGT Pro 225 | GCC CGG Ala | CCA GGT Pro | TAT ATA Tyr | GCT CGA Ala | CCC GGG Pro 230 | CAG GTC Gln | 703 |
| GGA CCT Gly | TGG ACC Trp | GGA CCT Gly | AAG TTC Lys 235 | GAA CTT Glu | ATT TAA Ile | GAG CTC Glu | CAG GTC Gln | AAG TTC Lys 240 | GTA CAT Val | CAG GTC Gln | GAG CTC Glu | TAA ATT | 742 |
| TAG ATC | CAATTCCTG GTTAAGGGAC | | TAGCTCTCAA ATCGAGAGTT | | AGCAAATTTT TCGTTTAAAA | | GAGCTCATTT CTCGAGTAAA | | | | | | 785 |
| TTCTTTTTCT AAGAAAAAGA | | GCAAGCTCAG CGTTCGAGTC | | CAGCAGAATG GTCGTCTTAC | | CCCAGAGTCT GGGTCTCAGA | | | | | | | 825 |
| TCCCTGGTAG AGGGACCATC | | ATGCAGGTTC TACGTCCAAG | | CATAGCGACG GTATCGCTGC | | TTCTCCTGCA AAGAGGACGT | | | | | | | 865 |
| ATGCACGCTG TACGTGCGAC | | GTATTCTGCA CATAAGACGT | | ATAGCAGGCC TATCGTCCGG | | ATGTTTTCCT TACAAAAGGA | | | | | | | 905 |
| TGAGCCTGGA ACTCGGACCT | | TGCTTTGGAG ACGAAACCTC | | CCAAGCTTTC GGTTCGAAAG | | GTCCCATGCA CAGGGTACGT | | | | | | | 945 |
| AGGGAAACAA TCCCTTTGTT | | CCACTTCTGG GGTGAAGACC | | GATGTCCGCT CTACAGGCGA | | GCAATCTGCT CGTTAGACGA | | | | | | | 985 |
| CCGGGGCTGC GGCCCCGACG | | AGCAACCTCA TCGTTGGAGT | | TCAGCTCTCT AGTCGAGAGA | | TGCCTGGAGT ACGGACCTCA | | | | | | | 1025 |
| GGCTCAGCCT CCGAGTCGGA | | GGCCTGCAGG CCGGACGTCC | | GCCACCAGGA CGGTGGTCCT | | GAATGGCAGC CTTACCGTCG | | | | | | | 1065 |
| AAGGATGGCG TTCCTACCGC | | AGGGTCCTCA TCCCAGGAGT | | TGGCTGGAAT ACCGACCTTA | | TC AG | | | | | | | 1097 |

The amino acid sequence for the protein encoded by the cDNA sequence for clone 3-1 can be found in SEQ ID NO:6.

In addition, the clone from an activated, human peripheral blood lymphocyte cDNA library labeled "31-10" contains 24 basepairs of 5' untranslated sequence, followed by an open reading frame comprised of the basepairs from position 135 to position 1991 of the DROME sequence given in SEQ ID NO:1 with two exceptions. Clone 31-10 contains 63 nucleotides inserted at position 238 in the DROME cDNA sequence which probably result from an intron which had not been spliced out in the DROME mRNA molecule that gave rise to the 31-10 clone. The inserted nucleotides remain in the open reading frame and are translated into an alternate form of the DROME protein.

The 31-10 clone also deviates in that nucleotides from position 1807 to 1952 in the DROME cDNA sequence are deleted. This deletion shifts out of frame the stop codons which would terminate translation in the other clones. When the mRNA represented by the 31-10 cDNA is translated, additional amino acids must be added to the C-terminal end of the DROME protein.

The sequence of clone 31-10 is as follows (SEQ ID NO:7):

| | | | | | | | | | | | | |
|---|---|---|---|---|---|---|---|---|---|---|---|---|
| GAATTCCGGA CTTAAGGCCT | | CGACAGCGGC GCTGTCGCCG | | TCTG AGAC | AGA TCT Arg 1 | GCC CGG Ala | CGG GCC Arg | CAG GTC Gln | ATT TAA Ile 5 | GCA CGT Ala | | | 42 |
| | GCA CGT Ala | AAA TTT Lys | ATT TAA Ile | GGA CCT Gly 10 | GGT CCA Gly | GAT CTA Asp | GCA CGT Ala | GGG CCC Gly | ACA TGT Thr 15 | TCA AGT Ser | CTG GAC Leu | AAT TTA Asn | TCA AGT Ser | 81 |
| | AAT TTA Asn 20 | GAC CTG Asp | TAT ATA Tyr | GGT CCA Gly | TAT ATA Tyr | GGG CCC Gly 25 | GGA CCT Gly | CAA GTT Gln | AAA TTT Lys | AGA TCT Arg | CCT GGA Pro 30 | TTA AAT Leu | GAA CTT Glu | 120 |

| | | | | | | | | | | | | |
|---|---|---|---|---|---|---|---|---|---|---|---|---|
| GAT | GGA | GAT | GGC | TCT | TGG | ACA | AGT | CCG | AGC | AGT | ACA | ACA | 159 |
| CTA | CCT | CTA | CCG | AGA | ACC | TGT | TCA | GGC | TCG | TCA | TGT | TGT | |
| Asp | Gly | Asp 35 | Gly | Ser | Trp | Thr | Ser 40 | Pro | Ser | Ser | Thr | Thr 45 | |
| CAC | TGG | GAG | GGA | ATG | CCC | TCT | CCT | TTT | AAA | GAT | CAA | CCA | 198 |
| GTG | ACC | CTC | CCT | TAC | GGG | AGA | GGA | AAA | TTT | CTA | GTT | GGT | |
| His | Trp | Glu | Gly | Met 50 | Pro | Ser | Pro | Phe | Lys 55 | Asp | Gln | Pro | |
| GAT | GCT | AAG | AAA | GTT | GCT | CCT | CAA | AAT | GAC | TCT | TTT | GGA | 237 |
| CTA | CGA | TTC | TTT | CAA | CGA | GGA | GTT | TTA | CTG | AGA | AAA | CCT | |
| Asp | Ala 60 | Lys | Lys | Val | Ala | Pro 65 | Gln | Asn | Asp | Ser | Phe 70 | Gly | |
| ACA | CAG | TTA | CCA | CCG | ATG | CAT | CAG | CAG | CAA | AGA | TCT | GTA | 276 |
| TGT | GTC | AAT | GGT | GGC | TAC | GTA | GTC | GTC | GTT | TCT | AGA | CAT | |
| Thr | Gln | Leu | Pro 75 | Pro | Met | His | Gln | Gln 80 | Gln | Arg | Ser | Val | |
| ATG | ACA | GAA | GAA | TAC | AAA | GTT | CCA | GAT | GGA | ATG | GTT | GGA | 315 |
| TAC | TGT | CTT | CTT | ATG | TTT | CAA | GGT | CTA | CCT | TAC | CAA | CCT | |
| Met 85 | Thr | Glu | Glu | Tyr | Lys 90 | Val | Pro | Asp | Gly | Met 95 | Val | Gly | |
| TTC | ATA | ATT | GGC | AGA | GGA | GGT | GAA | CAG | ATC | TCA | CGC | ATA | 354 |
| AAG | TAT | TAA | CCG | TCT | CCT | CCA | CTT | GTC | TAG | AGT | GCG | TAT | |
| Phe | Ile | Ile 100 | Gly | Arg | Gly | Gly | Glu 105 | Gln | Ile | Ser | Arg | Ile 110 | |
| CAA | CAG | GAA | TCT | GGA | TGC | AAA | ATA | CAG | ATA | GCT | CCT | GAC | 393 |
| GTT | GTC | CTT | AGA | CCT | ACG | TTT | TAT | GTC | TAT | CGA | GGA | CTG | |
| Gln | Gln | Glu | Ser | Gly 115 | Cys | Lys | Ile | Gln | Ile 120 | Ala | Pro | Asp | |
| AGT | GGT | GGC | CTT | CCA | GAA | AGG | TCC | TGT | ATG | TTA | ACT | GGA | 432 |
| TCA | CCA | CCG | GAA | GGT | CTT | TCC | AGG | ACA | TAC | AAT | TGA | CCT | |
| Ser | Gly 125 | Gly | Leu | Pro | Glu | Arg 130 | Ser | Cys | Met | Leu | Thr 135 | Gly | |
| ACA | CCT | GAA | TCT | GTC | CAG | TCA | GCA | AAA | CGG | TTA | CTG | GAC | 471 |
| TGT | GGA | CTT | AGA | CAG | GTC | AGT | CGT | TTT | GCC | AAT | GAC | CTG | |
| Thr | Pro | Glu | Ser 140 | Val | Gln | Ser | Ala | Lys 145 | Arg | Leu | Leu | Asp | |
| CAG | ATT | GTT | GAA | AAA | GGA | AGA | CCA | GCT | CCT | GGC | TTC | CAT | 510 |
| GTC | TAA | CAA | CTT | TTT | CCT | TCT | GGT | CGA | GGA | CCG | AAG | GTA | |
| Gln 150 | Ile | Val | Glu | Lys | Gly 155 | Arg | Pro | Ala | Pro | Gly 160 | Phe | His | |
| CAT | GGC | GAT | GGA | CCG | GGA | AAT | GCA | GTT | CAA | GAA | ATC | ATG | 549 |
| GTA | CCG | CTA | CCT | GGC | CCT | TTA | CGT | CAA | GTT | CTT | TAG | TAC | |
| His | Gly | Asp 165 | Gly | Pro | Gly | Asn | Ala 170 | Val | Gln | Glu | Ile | Met 175 | |
| ATT | CCA | GCT | AGC | AAG | GCA | GGA | TTA | GTC | ATT | GGA | AAA | GGG | 588 |
| TAA | GGT | CGA | TCG | TTC | CGT | CCT | AAT | CAG | TAA | CCT | TTT | CCC | |
| Ile | Pro | Ala | Ser | Lys 180 | Ala | Gly | Leu | Val | Ile 185 | Gly | Lys | Gly | |
| GGA | GAA | ACT | ATT | AAA | CAG | CTT | CAG | GAA | CGG | GCT | GGA | GTT | 627 |
| CCT | CTT | TGA | TAA | TTT | GTC | GAA | GTC | CTT | GCC | CGA | CCT | CAA | |
| Gly | Glu 190 | Thr | Ile | Lys | Gln | Leu 195 | Gln | Glu | Arg | Ala | Gly 200 | Val | |
| AAA | ATG | GTT | ATG | ATT | CAA | GAC | GGG | CCG | CAG | AAC | ACT | GGT | 666 |
| TTT | TAC | CAA | TAC | TAA | GTT | CTG | CCC | GGC | GTC | TTG | TGA | CCA | |
| Lys | Met | Val | Met 205 | Ile | Gln | Asp | Gly | Pro 210 | Gln | Asn | Thr | Gly | |
| GCT | GAC | AAA | CCT | CTT | AGG | ATT | ACA | GGA | GAC | CCA | TAT | AAA | 705 |
| CGA | CTG | TTT | GGA | GAA | TCC | TAA | TGT | CCT | CTG | GGT | ATA | TTT | |
| Ala 215 | Asp | Lys | Pro | Leu | Arg 220 | Ile | Thr | Gly | Asp | Pro 225 | Tyr | Lys | |
| GTT | CAA | CAA | GCC | AAG | GAA | ATG | GTG | TTA | GAG | TTA | ATT | CGT | 744 |
| CAA | GTT | GTT | CGG | TTC | CTT | TAC | CAC | AAT | CTC | AAT | TAA | GCA | |
| Val | Gln | Gln 230 | Ala | Lys | Glu | Met | Val 235 | Leu | Glu | Leu | Ile | Arg 240 | |

| | | | | | | | | | | | | | |
|---|---|---|---|---|---|---|---|---|---|---|---|---|---|
| GAT | CAA | GGC | GGT | TTC | AGA | GAA | GTT | CGG | AAT | GAG | TAT | GGG | 783 |
| CTA | GTT | CCG | CCA | AAG | TCT | CTT | CAA | GCC | TTA | CTC | ATA | CCC | |
| Asp | Gln | Gly | Gly | Phe | Arg | Glu | Val | Arg | Asn | Glu | Tyr | Gly | |
| | | | | 245 | | | | | 250 | | | | |
| TCA | AGA | ATA | GGA | GGA | AAT | GAA | GGG | ATA | GAT | GTC | CCC | ATT | 822 |
| AGT | TCT | TAT | CCT | CCT | TTA | CTT | CCC | TAT | CTA | CAG | GGG | TAA | |
| Ser | Arg | Ile | Gly | Gly | Asn | Glu | Gly | Ile | Asp | Val | Pro | Ile | |
| | 255 | | | | | 260 | | | | | 265 | | |
| CCA | AGA | TTT | GCT | GTT | GGC | ATT | GTA | ATA | GGA | AGA | AAT | GGA | 861 |
| GGT | TCT | AAA | CGA | CAA | CCG | TAA | CAT | TAT | CCT | TCT | TTA | CCT | |
| Pro | Arg | Phe | Ala | Val | Gly | Ile | Val | Ile | Gly | Arg | Asn | Gly | |
| | | | 270 | | | | | 275 | | | | | |
| GAG | ATG | ATC | AAA | AAA | ATA | CAA | AAT | GAT | GCT | GGT | GTT | CGC | 900 |
| CTC | TAC | TAG | TTT | TTT | TAT | GTT | TTA | CTA | CGA | CCA | CAA | GCG | |
| Glu | Met | Ile | Lys | Lys | Ile | Gln | Asn | Asp | Ala | Gly | Val | Arg | |
| 280 | | | | | 285 | | | | | 290 | | | |
| ATT | CAG | TTT | AAG | CCA | GAT | GAT | GGG | ACA | ACA | CCC | GAA | AGG | 939 |
| TAA | GTC | AAA | TTC | GGT | CTA | CTA | CCC | TGT | TGT | GGG | CTT | TCC | |
| Ile | Gln | Phe | Lys | Pro | Asp | Asp | Gly | Thr | Thr | Pro | Glu | Arg | |
| | | 295 | | | | | 300 | | | | | 305 | |
| ATA | GCA | CAA | ATA | ACA | GGA | CCT | CCA | GAC | CGA | TGT | CAA | CAT | 978 |
| TAT | CGT | GTT | TAT | TGT | CCT | GGA | GGT | CTG | GCT | ACA | GTT | GTA | |
| Ile | Ala | Gln | Ile | Thr | Gly | Pro | Pro | Asp | Arg | Cys | Gln | His | |
| | | | | 310 | | | | | 315 | | | | |
| GCT | GCA | GAA | ATT | ATT | ACA | GAC | CTT | CTT | CGA | AGT | GTT | CAG | 1017 |
| CGA | CGT | CTT | TAA | TAA | TGT | CTG | GAA | GAA | GCT | TCA | CAA | GTC | |
| Ala | Ala | Glu | Ile | Ile | Thr | Asp | Leu | Leu | Arg | Ser | Val | Gln | |
| | 320 | | | | | 325 | | | | | 330 | | |
| GCT | GGT | AAT | CCT | GGT | GGA | CCT | GGA | CCT | GGT | GGT | CGA | GGA | 1056 |
| CGA | CCA | TTA | GGA | CCA | CCT | GGA | CCT | GGA | CCA | CCA | GCT | CCT | |
| Ala | Gly | Asn | Pro | Gly | Gly | Pro | Gly | Pro | Gly | Gly | Arg | Gly | |
| | | | 335 | | | | | 340 | | | | | |
| AGA | GGT | AGA | GGT | CAA | GGC | AAC | TGG | AAC | ATG | GGA | CCA | CCT | 1095 |
| TCT | CCA | TCT | CCA | GTT | CCG | TTG | ACC | TTG | TAC | CCT | GGT | GGA | |
| Arg | Gly | Arg | Gly | Gln | Gly | Asn | Trp | Asn | Met | Gly | Pro | Pro | |
| 345 | | | | | 350 | | | | | 355 | | | |
| GGT | GGA | TTA | CAG | GAA | TTT | AAT | TTT | ATT | GTG | CCA | ACT | GGG | 1134 |
| CCA | CCT | AAT | GTC | CTT | AAA | TTA | AAA | TAA | CAC | GGT | TGA | CCC | |
| Gly | Gly | Leu | Gln | Glu | Phe | Asn | Phe | Ile | Val | Pro | Thr | Gly | |
| | | 360 | | | | | 365 | | | | | 370 | |
| AAA | ACT | GGA | TTA | ATA | ATA | GGA | AAA | GGA | GGT | GAA | ACC | ATA | 1173 |
| TTT | TGA | CCT | AAT | TAT | TAT | CCT | TTT | CCT | CCA | CTT | TGG | TGT | |
| Lys | Thr | Gly | Leu | Ile | Ile | Gly | Lys | Gly | Glu | Thr | Ile | | |
| | | | | 375 | | | | | 380 | | | | |
| AAA | AGC | ATA | AGC | CAG | CAG | TCT | GGT | GCA | AGA | ATA | GAA | CTT | 1212 |
| TTT | TCG | TAT | TCG | GTC | GTC | AGA | CCA | CGT | TCT | TAT | CTT | GAA | |
| Lys | Ser | Ile | Ser | Gln | Gln | Ser | Gly | Ala | Arg | Ile | Glu | Leu | |
| | 385 | | | | | 390 | | | | | 395 | | |
| CAG | AGA | AAT | CCT | CCA | CCA | AAT | GCA | GAT | CCT | AAT | ATG | AAG | 1251 |
| GTC | TCT | TTA | GGA | GGT | GGT | TTA | CGT | CTA | GGA | TTA | TAC | TTC | |
| Gln | Arg | Asn | Pro | Pro | Pro | Asn | Ala | Asp | Pro | Asn | Met | Lys | |
| | | | 400 | | | | | 405 | | | | | |
| TTA | TTT | ACA | ATT | CGT | GGC | ACT | CCA | CAA | CAG | ATA | GAC | TAT | 1290 |
| AAT | AAA | TGT | TAA | GCA | CCG | TGA | GGT | GTT | GTC | TAT | CTG | ATA | |
| Leu | Phe | Thr | Ile | Arg | Gly | Thr | Pro | Gln | Gln | Ile | Asp | Tyr | |
| 410 | | | | | 415 | | | | | 420 | | | |
| GCT | CGG | CAA | CTC | ATA | GAA | GAA | AAG | ATT | GGT | GGC | CCA | GTA | 1329 |
| CGA | GCC | GTT | GAG | TAT | CTT | CTT | TTC | TAA | CCA | CCG | GGT | CAT | |
| Ala | Arg | Gln | Leu | Ile | Glu | Glu | Lys | Ile | Gly | Gly | Pro | Val | |
| | | 425 | | | | | 430 | | | | | 435 | |
| AAT | CCT | TTA | GGG | CCA | CCT | GTA | CCC | CAT | GGG | CCC | CAT | GGT | 1368 |
| TTA | GGA | AAT | CCC | GGT | GGA | CAT | GGG | GTA | CCC | GGG | GTA | CCA | |
| Asn | Pro | Leu | Gly | Pro | Pro | Val | Pro | His | Gly | Pro | His | Gly | |
| | | | | 440 | | | | | 445 | | | | |

| | | | | | | | | | | | | | |
|---|---|---|---|---|---|---|---|---|---|---|---|---|---|
| GTC | CCA | GGC | CCC | CAT | GGA | CCT | CCT | GGG | CCT | CCA | GGG | CCT | 1407 |
| CAG | GGT | CCG | GGG | GTA | CCT | GGA | GGA | CCC | GGA | GGT | CCC | GGA | |
| Val | Pro 450 | Gly | Pro | His | Gly | Pro 455 | Pro | Gly | Pro | Pro | Gly 460 | Pro | |
| GGA | ACT | CCA | ATG | GGA | CCA | TAC | AAC | CCT | GCA | CCT | TAT | AAT | 1446 |
| CCT | TGA | GGT | TAC | CCT | GGT | ATG | TTG | GGA | CGT | GGA | ATA | TTA | |
| Gly | Thr | Pro | Met 465 | Gly | Pro | Tyr | Asn | Pro 470 | Ala | Pro | Tyr | Asn | |
| CCT | GGA | CCA | CCA | GGC | CCG | GCT | CCT | CAT | GGT | CCT | CCA | GCC | 1485 |
| GGA | CCT | GGT | GGT | CCG | GGC | CGA | GGA | GTA | CCA | GGA | GGT | CGG | |
| Pro 475 | Gly | Pro | Pro | Gly | Pro 480 | Ala | Pro | His | Gly | Pro 485 | Pro | Ala | |
| CCA | TAT | GCT | CCC | CAG | GGA | TGG | GGA | AAT | GCA | TAT | CCA | CAC | 1524 |
| GGT | ATA | CGA | GGG | GTC | CCT | ACC | CCT | TTA | CGT | ATA | GGT | GTG | |
| Pro | Tyr | Ala 490 | Pro | Gln | Gly | Trp | Gly 495 | Asn | Ala | Tyr | Pro | His 500 | |
| TGG | CAG | CAG | CAG | GCT | CCT | CCT | GAT | CCA | GCT | AAG | GCA | GGA | 1563 |
| ACC | GTC | GTC | GTC | CGA | GGA | GGA | CTA | GGT | CGA | TTC | CGT | CCT | |
| Trp | Gln | Gln | Gln | Ala 505 | Pro | Pro | Asp | Pro | Ala 510 | Lys | Ala | Gly | |
| ACG | GAT | CCA | AAT | TCA | GCA | GCT | TGG | GCT | GCT | TAT | TAC | GCT | 1602 |
| TGC | CTA | GGT | TTA | AGT | CGT | CGA | ACC | CGA | CGA | ATA | ATG | CGA | |
| Thr | Asp 515 | Pro | Asn | Ser | Ala | Ala 520 | Trp | Ala | Ala | Tyr | Tyr 525 | Ala | |
| CAC | TAT | TAT | CAA | CAG | CAA | GCA | CAG | CCA | CCA | CCA | GCA | GCC | 1641 |
| GTG | ATA | ATA | GTT | GTC | GTT | CGT | GTC | GGT | GGT | GGT | CGT | CGG | |
| His | Tyr | Tyr | Gln 530 | Gln | Gln | Ala | Gln | Pro 535 | Pro | Pro | Ala | Ala | |
| CCT | GCA | GGT | GCA | CCA | ACT | ACA | ACT | CAA | ACT | AAT | GGA | CAA | 1680 |
| GGA | CGT | CCA | CGT | GGT | TGA | TGT | TGA | GTT | TGA | TTA | CCT | GTT | |
| Pro 540 | Ala | Gly | Ala | Pro | Thr 545 | Thr | Thr | Gln | Thr | Asn 550 | Gly | Gln | |
| GGA | GAT | CAG | CAG | AAT | CCA | GCC | CCA | GCT | GGA | CAG | GTT | GAT | 1719 |
| CCT | CTA | GTC | GTC | TTA | GGT | CGG | GGT | CGA | CCT | GTC | CAA | CTA | |
| Gly | Asp | Gln 555 | Gln | Asn | Pro | Ala | Pro 560 | Ala | Gly | Gln | Val | Asp 565 | |
| TAT | ACC | AAG | GCT | TGG | GAA | GAG | TAC | TAC | AAG | AAA | ATG | GGG | 1758 |
| ATA | TGG | TTC | CGA | ACC | CTT | CTC | ATG | ATG | TTC | TTT | TAC | CCC | |
| Tyr | Thr | Lys | Ala | Trp 570 | Glu | Glu | Tyr | Tyr | Lys 575 | Lys | Met | Gly | |
| CCA | ATA | ATA | AGA | AGT | GGA | CAA | TAC | AGT | ATT | TGC | TTC | | 1794 |
| GGT | TAT | TAT | TCT | TCA | CCT | GTT | ATG | TCA | TAA | ACG | AAG | | |
| Pro | Ile 580 | Ile | Arg | Ser | Gly | Gln 585 | Tyr | Ser | Ile | Cys | Phe 590 | | |
| AGGAATTCC | | | | | | | | | | | | | 1803 |
| TCCTTAAGG | | | | | | | | | | | | | |

The amino acid sequence for the protein encoded by the cDNA sequence for clone 31-10 can be found in SEQ ID NO:8.

The following examples are for illustration only, and should not be used to limit the scope of the invention.

EXAMPLE 1

The cloned cDNA encodes a protein with FUSE binding activity, referred to as DROME or FUSE binding protein ("FBP"). The coding region contained in the HL60 clones was expressed as a fusion protein in bacteria, purified from extracts and tested with electrophoretic mobility shift assays (EMSAs) for binding to an oligonucleotide containing the FUSE site. Recombinant fusion protein (GST-FBP) bound effectively to the FUSE oligonucleotide.

The open reading frame present in the HL60-1 and HL60-2 clones (amino acid residues 145 to 511) was expressed as a Glutathione-S-transferase fusion protein (GST-FBP) in the pGEX system. The inserts from the HL60-1 and HL60-2 clones were spliced together and the open reading frame region subcloned into the Sma I site of the pGEX-2T plasmid (AMARAD Corp.; D. B. Smith and K. S. Johnson, Gene. 67,31 (1988)) to express a GST-FBP fusion protein. Recombinant protein was purified from E. coli extracts on a glutathione-agarose matrix (Sigma Chemical Co.), GST alone was prepared from a pGEX-2T plasmid with no insert in a similar manner. Fusion proteins were eluted with 20 mM glutathione, checked for purity, correct size and concentration with SDS PAGE.

Purified recombinant proteins were incubated with double stranded, $^{32}P$ labeled, oligonucleotide (Probe) in the presence or absence of the indicated quantity of unlabeled, double stranded oligonucleotide as competitor, and subjected to EMSA. (M. Fried and D. M. Crothers, *Nucleic Acids Res.* 9, 6505 (1981)).

DNA binding assays were performed with an equivalent amount of GST-FBP or GST alone incubated in 25 mM Tris, 200 mM Glycine, 1 mM EDTA, 0.5 mg/ml BSA, 0.1% Tween20, 10% glycerol, 100 µg/ml poly(dI:dC), and 0.2 ng of labeled probe. The probe was prepared by annealing two complementary synthetic oligonucleotides and 5' end labeling with $T_4$ polynucleotide kinase in the presence of $\gamma$-$^{32}$P-ATP. The top strand of the FUSE oligonucleotide was 5'-GATCACAAAATAAAAAATCCCGAGGGAATATAG-3'(SEQ ID NO: 11). The top strand of Mut A was 5'-GATCACAActacgtgctaggacgccGAATATAG-3' (SEQ ID NO: 12) (lower case indicates changes from FUSE oligomer sequence). The top strand of CRE was 5'-GATCTGACGTCATGACTGACGTCATGACTGACGTCATCA-3' (SEQ ID NO: 13). The top strand of CTE was 5'-AATTCTCCTCCCCACCTTCCCCACCCTCCCCA-3' (SEQ ID NO: 14). Reaction mixtures were incubated 30 minutes at room temperature and protein-DNA complexes resolved by electrophoresis on a 4.2% acrylamide gel in 25 mM Tris, 200 mM Glycine, 1 mM EDTA buffer.

Figure 3A:
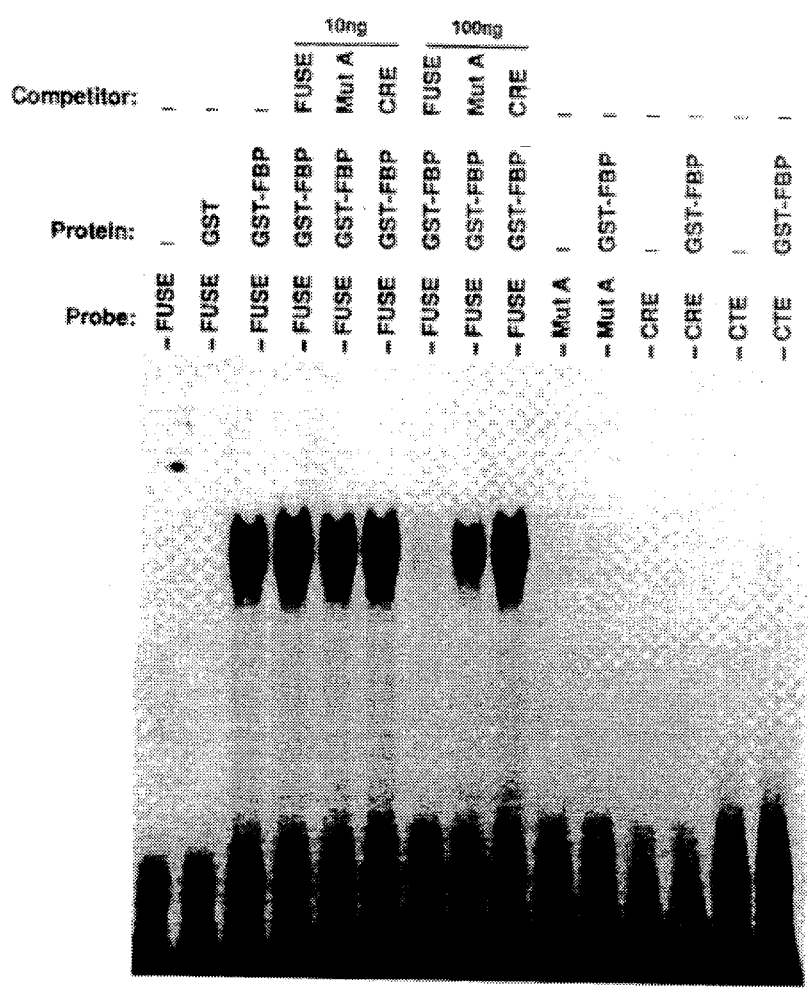
FIGS. 3A & B depict DNA binding assay radiographs showing that recombinant FBP binds specifically to the far upstream element.

Radioactive DNA and DNA-protein complexes were visualized by autoradiography (FIG. 3A). Glutathione-S-transferase (GST) alone did not bind to the probe. Competitor oligonucleotides were as follows: Mut A, a mutant FUSE oligonucleotide with 17 residues covering the binding site changed; CRE, CAMP response element; CTE, CT element in c-myc 5' flanking region.

Figure 3B:
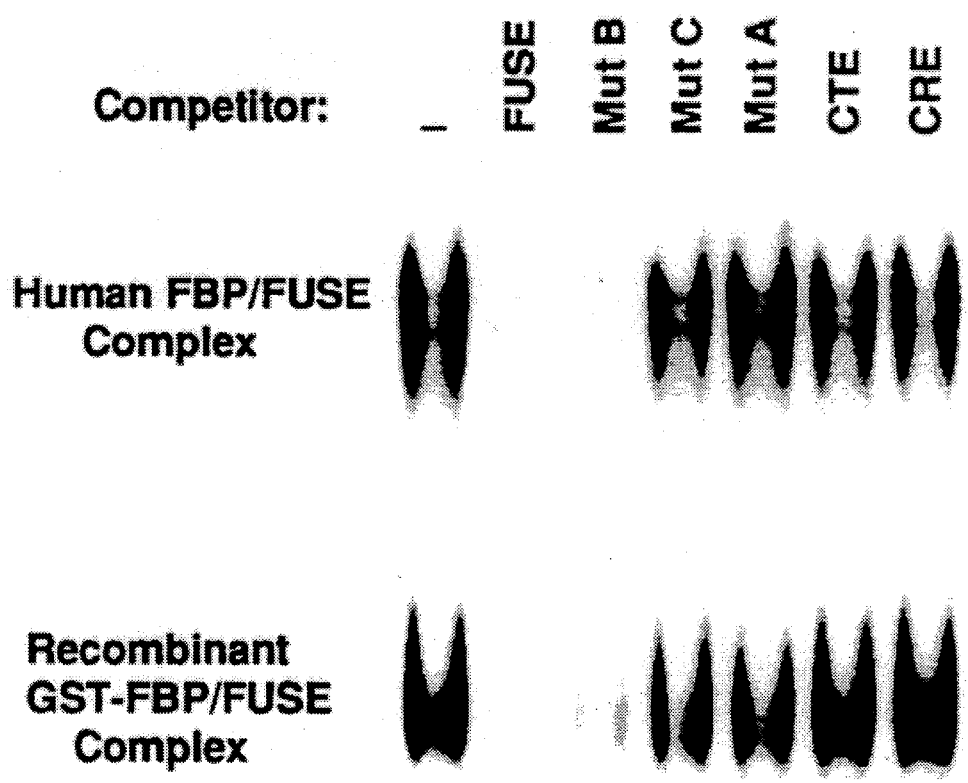

Recombinant FBP and purified human FBP were also demonstrated to display similar DNA binding specificity. Full length GST-FBP and human FBP purified from HL60 cells by oligo-affinity chromatography were assayed for FUSE binding using EMSA. The DNA-protein complexes formed by human FBP in the presence of 25ng of the indicated nonradioactive competitors, visualized by autoradiography, are shown in the upper panel of FIG. 3B. The lower panel of FIG. 3B shows recombinant GST-FBP binding the FUSE probe in the presence of 25 ng of the same competitors. Competitor oligonucleotides are the same as in (A) with the addition of Mut B and Mut C, each with a different mutation in the FUSE sequence. The top strand of Mut B was 5'-GATCACAAAATAAAAAATggacgcGAATATAG-3' (SEQ ID NO:15) and the top strand of Mut C was 5'-GATCACAActacgtgctaggCGAGGGAATATAG-3' (SEQ ID NO:16).

Recombinant fusion protein also failed to bind to the nonhomologous oligonucleotides when they were used as radioactive probes. The full length recombinant protein, and purified human FBP shared the same DNA binding specificity as indicated by challenging their binding to FUSE with a panel of competitors (FIG. 3B). An excess of cold FUSE significantly reduced binding of human and recombinant FBP to the radioactive probe; the same amount of the Mut B oligo which has minor changes in the FUSE sequence, bound both as well; but more divergent oligonucleotides did not significantly compete for binding to either protein.

EXAMPLE 2

Figure 4:
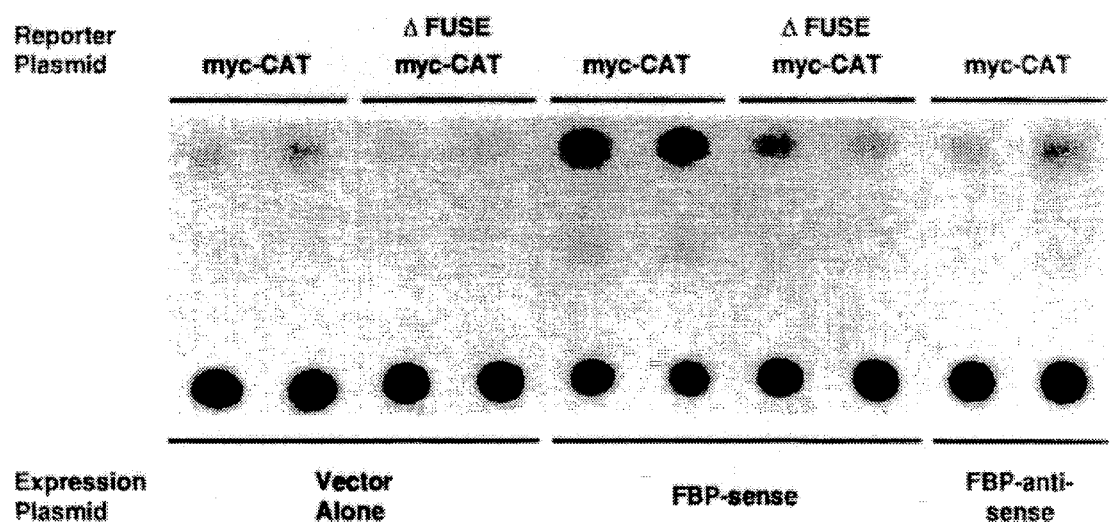
FIG. 4 shows assays depicting recombinant FBP activated expression of a chloramphenicol acetyltransferase (CAT) gene under the control of human c-myc regulatory sequence.

Recombinant FBP activated expression of a chloramphenicol acetyltransferase (CAT) gene under the control of human c-myc regulatory sequence was tested in co-transection experiments (FIG. 4).

Full length FBP was inserted into an expression vector downstream from the cytomegalovirus enhancer/promoter in both the sense and anti-sense orientations. These plasmids or the expression vector alone were transfected into U937 cells with another vector containing a CAT gene under the control of myc regulator sequence (myc-CAT) or the reporter plasmid with the FUSE site deleted (ΔFUSE myc-CAT). The myc-CAT and ΔFUSE myc-CAT reporter plasmids are derivatives of pMP CAT (M. Avigan, B. Strober, and D. Levens, *J. Biol. Chem.*, 265,18538 (1990)) with the deletion of a 580bp Nsi I fragment from position −669 to −1249 relative to the myc P1 promoter. The Nsi I deletion results in more consistent CAT expression without disrupting FUSE mediated activation. The ΔFUSE myc-CAT plasmid was produced from pMP CAT by cutting the parent plasmid at the Ava I site located in the FUSE element, partial digestion with mung bean exonuclease (Bethesda Research Labs) and religation. The DNA sequence of the deleted plasmid revealed that 68 nucleotides between position −1493 and −1561 relative to myc P1 were removed, completely deleting the FUSE element.

U937 cells ($5\times10^6$) were electroporated (Cell-porator, BRL, 200V, 1180µF) with 10µg of each plasmid in 250µl of RPMI supplemented with 10% fetal calf serum. Transfected cells were added to 8ml additional medium and incubated 48 hours before harvesting for CAT assays. (C. M. Gorman, L. F. Moffat, B. H. Howard, *Mol. Cell. Biol.* 2, 1044 (1982)). The same quantity of protein (Bradford method) was assayed for each extract. Two independent transfections are shown for each plasmid combination.

In the presence of the FBP expression plasmid (FBP-sense), the FUSE containing myc-CAT plasmid (myc-CAT) gave a 5-fold higher level of CAT activity than in the presence of the expression vector alone. In contrast, this level of stimulation did not occur when the reporter plasmid had a 68 bp deletion that eliminated the FUSE site (ΔFUSE myc-CAT) nor when the expression plasmid contained the FBP cDNA in the reverse orientation (FBP-antisense). The minor increase in the ΔFUSE myc-CAT expression with FBP co-transection could be due to secondary binding sites present in the myc regulatory sequence.

FBP shows no significant homology to known DNA binding motifs in a search against the GenBank databases, however the primary amino acid sequence of FBP has distinct structural features which could constitute a DNA binding domain, as well as other features with potential functional significance.

EXAMPLE 3

A Pustell matrix self-comparison of FBP revealed three domains in the primary amino acid sequence, each containing internally repeated sequences.

Figure 5A:
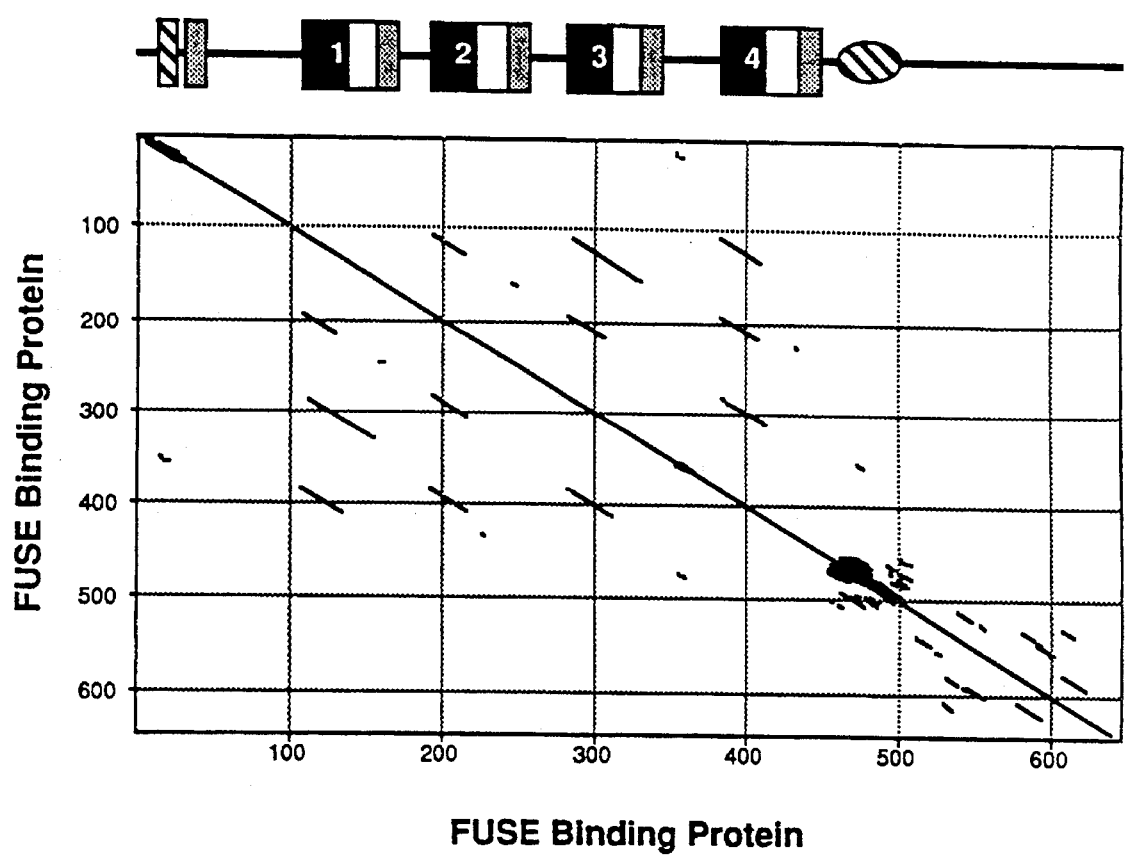
FIGS. 5A, 5B and 5C show the structural features of the primary amino acid sequence of FBP.

The Pustell matrix (J. Pustell, F. C. Kafatos, *N. A. R.* 10, 4765 (1982); W. R. Pearson, *Meth. Enzymol.* 183, 63 (1990); MacVector software, International Biotechnologies, Inc.) revealed the repeated sequences in the three domains of FBP. The repeated glycines in the N-terminal domain, the four copies of the FBP repeat in the central domain, the proline/glycine rich segment and the WAAYY (where W is Trp, A is Ala and Y is Tyr) repeat in the C-terminal domain all score as diagonals. A window size of 20 residues and a minimum score of 35% were used for this analysis. The diagram above the box in FIG. 5A symbolizes the structures in FBP: striped fill indicates glycine rich segments, the solid boxes indicate the FBP repeats, and the shaded boxes represent amphipathic helices.

The amino-terminal domain is comprised of 106 amino acids featuring a string of 11 repeated glycine residues and the first of 5 predicted amphipathic alpha helices found in FBP. Following the helix, residues 63 to 106 are enriched for glutamine (16%) relative to the whole protein (9%).

Figures 5B, 5C:
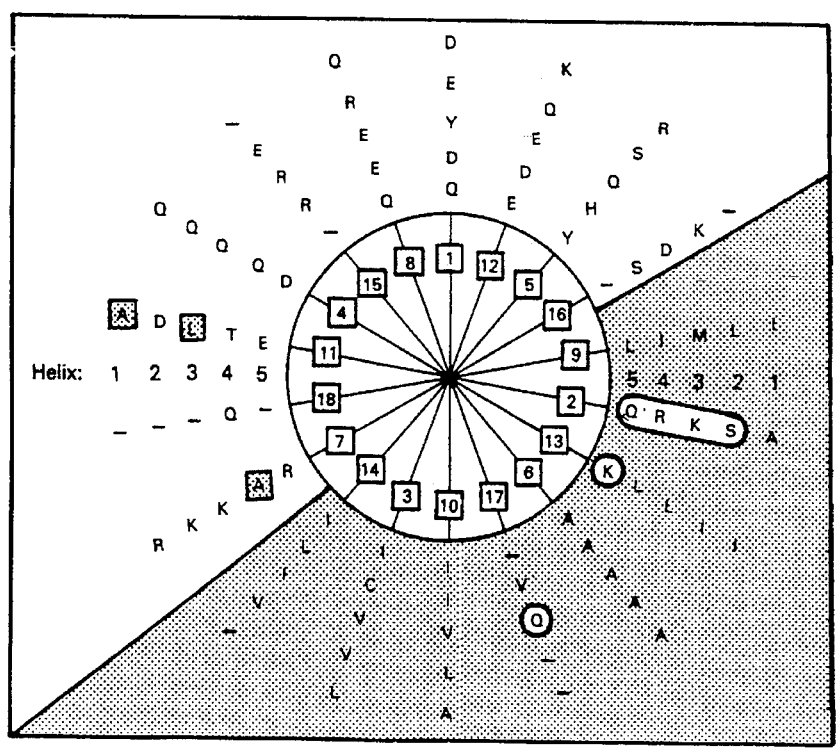

The central and largest FBP domain contains structures sufficient for sequence specific binding because a recombinant protein comprised of only this domain bound DNA specifically. The central domain is made up of four evenly spaced units each unit containing (1) a highly conserved 30 residue segment termed here the FBP repeat (FIG. 5B), followed by (2) a potential amphipathic alpha helix (FIG. 5C). Each FBP repeat is comprised of three structures in sequential order: a region of predicted β-sheet, separated by a turn at conserved glycines 13 and 14, from a segment of alpha-helix as predicted by Chou-Fasman and Robson-Garnier analysis. (P. Y. Chou and G. D. Fasman, "Prediction of the secondary structure of proteins from their amino acid sequence." *Adv. Enzymol. Relat. Areas Mol. Biol.* 47:45–148 (1978); B. Robson and E. Suzuki, "Conformational properties of amino acid residues in globular proteins." *J. Mol. Biol.* 107:327–356 (1976); J. Garnier, D. J. Osguthorpe, and B. Robson, "Analysis of the accuracy and implications of simple methods for predicting the secondary structure of globular proteins." *J. Mol. Biol.* 120:97–120 (1978). Analysis was performed with MacVector Software (International Biotechnologies, Inc.)). The FBP repeats are found at amino acid positions 107–136, 192–221, 282–311 and 383–412.

The invariant glycine at position 25 may not disrupt helix formation due to the hydrophilic character of neighboring residues in the predicted helix. (L. Serrano, J. L. Neira, J. Sancho, and A. R. Fersht, "Effect of alanine versus glycine in alpha-helices on protein stability." *Nature*, 356:453–455 (1992)). This sheet-turn-helix pattern evokes the DNA-binding domain of the papilloma virus E2 protein. (R. S. Hegde, S. R. Grossman, L. A. Laimins, and P. Sigler, "Crystal structure at 1.7 Å of the bovine papillomavirus-1 E2 DNA-binding domain bound to its DNA target." Nature 359:505–512 (1992)). An amphipathic helix follows each repeat after a spacer of 18–21 residues. The amphipathic helices are found at amino acid positions 155–170, 242–258, 330–347 and 434–447. The amphipathic character of the four central domain helices extends uniformly over their 16–18 residue lengths with the exception of hydrophilic residues at position 2 (FIG. 5C). The lack of a hydrophobic residue at this position deviates from the heptad repeat pattern shown to be important in coiled-coiled interactions. (F. H. C. Crick, *Nature*. 170, 882 (1952)). The helices are not flanked by basic regions as in basic-coiled-coil (S. C. Harrison, "Structural taxonomy of DNA-binding proteins." *Nature*, 353:715–719 (1991); W. H. Landschulz, P. F. Johnson, and S. L. McKnight. *Science*, 240:1759–1764 (1988)) or helix-loop-helix motifs. (C. Murre, P. Schonleber McCaw, and D. Baltimore, "A new DNA binding and dimerization motif in immunoglobulin enhancer binding, daughterless, MyoD, and myc proteins." *Cell* 56:777–783 (1989)). Thus the repeat-helix unit found in the central domain of FBP does not resemble known DNA binding motifs.

The C-terminal domain is separated from the central domain by a highly flexible, proline-glycine rich segment. This domain is also glutamine rich (22/140=15.7% from amino acid 505 to the C-terminal) and tyrosine rich (13/140=9.3%) including repeated tyrosine dyad motifs some of which conform to a tyrosine phosphorylation recognition site. (J. A. Cooper, F. S. Esch, S. S. Taylor, and T. Hunter, "Phosphorylation sites in enolase and lactate dehydrogenase utilized by tyrosine protein kinases in vivo and in vitro." *J. Biol. Chem.* 259:7835–7841 (1984)).

EXAMPLE 4

To define a minimum DNA binding motif within the central domain, further truncations were constructed as well as short insertions to disrupt the predicted structures. Mutant constructs were expressed as bacterial fusion proteins, purified and tested for DNA binding to the FUSE oligonucleotide.

The plasmid which encodes the 278-511 mutant was constructed by inserting an EcoR I-Sac I fragment from the HL60-2 clone into the pGEX-1 vector. The fusion protein contains amino acids 278-511 of FBP plus the residues KEIEQKVQE (SEQ ID NO:17) (where K is Lys, E is Glu, I is Ile, Q is Gln, and V is Val) at the carboxyterminal end stopping at a termination codon unique to the HL60-2 clone. The 278-474 encoding plasmid was constructed from the 278-511 plasmid by inserting a 12 bp double stranded oligonucleotide with the sequence TTAGTTAACTAA (SEQ ID NO.18) into an Sfi I site. This oligonucleotide encodes stop codons in all 3 reading frames so that a truncated protein is produced. The 278-372 encoding plasmid was similarly constructed by inserting the termination oligonucleotide into a Dra III site. The 298-511 encoding plasmid was constructed from the 278-511 plasmid by deleting a fragment between the BamH I site in the pGEX vector and a Bcl I in the FBP cDNA.

Figure 6A:
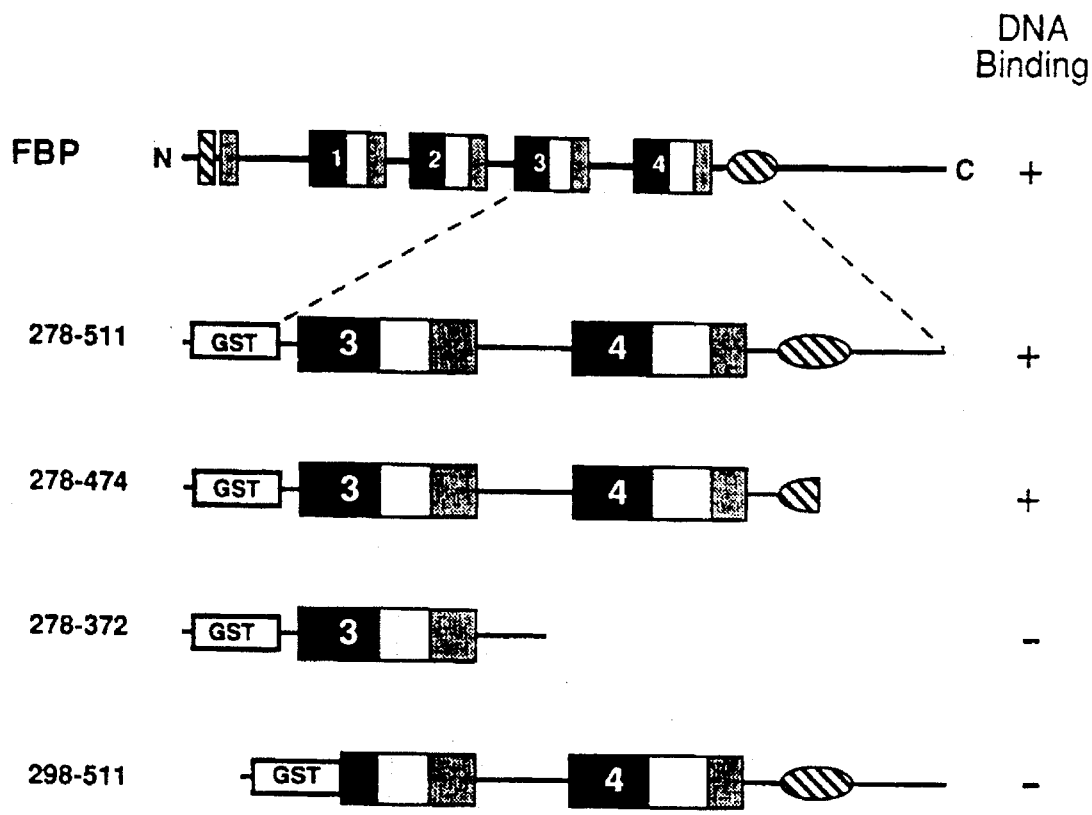
FIGS. 6A–6C illustrate a mutational analysis of the minimum DNA binding domain of recombinant FBP.

The ability of each construct to bind (+) or failure to bind (−) the FUSE DNA sequence is indicated at the right in FIG. 6A. The open boxes labeled "GST" indicate the glutathione-S-transferase fragment present in the fusion proteins. Other symbols are the same as in FIG. 5A.

Figure 6B:
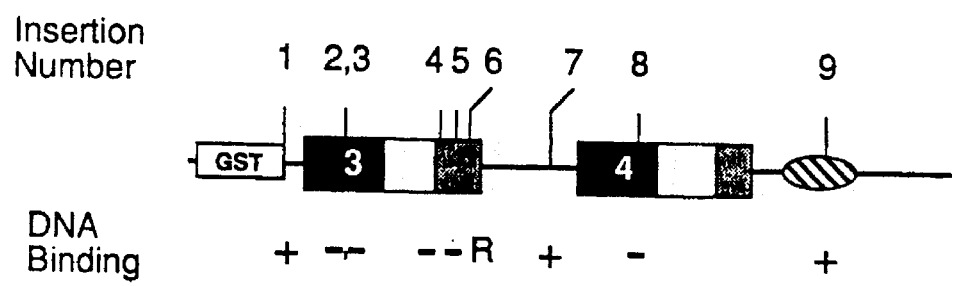
Figure 6C:
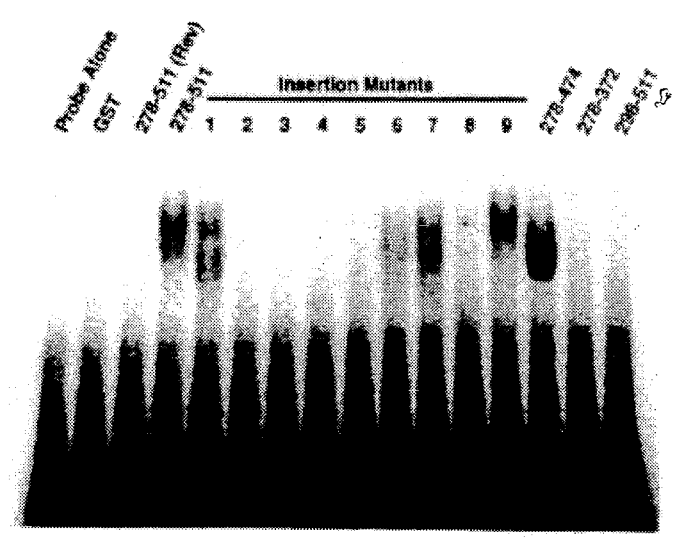

The truncated protein containing the third and fourth units of the central domain and the proline/glycine rich region (278-511, FIG. 6A) bound DNA with the same specificity as full length DROME or FPB (FIG. 6C). A truncation mutant lacking a portion of the proline-glycine rich region (278-474) still bound DNA. In contrast, the removal of FBP repeat 4 and the rest of the C-terminus in a mutant with a larger truncation (278-372) or removal of the NH$_2$-terminal portion of repeat 3 (298-511) abrogated binding. These truncations suggest that at least two intact FBP repeat-helix units are required to constitute a DNA binding domain and that at least half of the Pro—Gly region is not required.

EXAMPLE 5

Insertion mutants further demonstrated the importance of two repeat-helix units for DNA binding. Three to six amino acids were introduced at eight positions throughout the 278-511 construct (FIG. 6B) without altering the reading frame.

The insertion mutants were constructed by cutting the 278-511 plasmid at restriction sites, treating the ends with the large fragment of DNA polymerase I (if not already blunt) and inserting linkers of 8, 10 or 12 base pairs. The appropriate length was chosen to insert a small number of amino acids but restore the original reading frame leaving the rest of the sequence unchanged. Insertion mutant 1 had the amino acids ArgIleArg added between GST and the FBP polypeptide. Mutant 2 had residues IleGlySerArgIleArg (SEQ ID NO:19) added after the Met at position 297 in FBP, mutant 3 had IleArgIleArg (SEQ ID NO:20) added after Met297. Mutant 4 had ProArgIleArgGlu (SEQ ID NO:21) added while deleting Gln at amino acid 333. Mutant 5 had GlyIlePro added after amino acid 336. Mutant 6 had GlyIleProArg (SEQ ID NO:22) added after amino acid 343. Mutant 7 ArgIleArg added after amino acid 373. Mutant 8 had ArgAspProAla (SEQ ID NO:23) added while deleting GlnSer after amino acid 404. Mutant 9 had ArgGlySerGly (SEQ ID NO:24) inserted while deleting Pro after amino acid 475. All constructs were confirmed by DNA sequencing. The DNA binding property of each insertion mutant is indicated by a +, − or R (reduced binding) below the insertion site.

An insertion at the junction between GST and the FBP sequence (insertion mutant number 1) does not effect binding. Neither do insertions into the region between helix 4 and repeat 4 (number 7) or the Pro-Gly region (number 9). In contrast, insertions 2 and 3 in repeat three, insertions 4 and 5 in helix four, and insertion 8 in repeat four all resulted in mutant proteins failing to bind DNA. Insertion number 6, near the end of helix four, reduced but did not eliminate binding.

The combined evidence from RNA expression, DNA binding specificity and transection experiments indicate the presence of a human FUSE binding protein (referred to as FBP or DROME) that activates myc expression. FBP binds DNA through a novel, repeated motif. The presence of four sets of the repeat-helix unit in FBP, when only two are required for FUSE binding, suggests that this protein has the potential to form at least two binding sites. A dual binding capability may be important for its cellular function. For example, binding of FBP could facilitate DNA looping which stimulates the interaction of distant elements, a mechanism consistent with the far upstream location and the requirement for additional regulatory sequence to observe the stimulatory effect of the FUSE site.

EXAMPLE 6

The purified FUSE binding protein is also useful in the production of monoclonal antibodies. Thus, a mouse is injected with purified FUSE binding protein, or a fragment thereof, which activates a number of B-lymphocytes in the mouse which produce antibodies against the protein. The mouse is sacrificed and spleen lymphoid cells, containing large quantities of these B-lymphocytes, are isolated and tested to assure production of antibody to FUSE binding protein. The lymphocytes producing antibody to FUSE binding protein are then fused with mouse plasmacytoma cells, ensuring a reproducible source of monoclonal antibody (Kohler, G. and Milstein, C. *Nature,* 256:495–97 (1975)). These antibodies, or fragments thereof, can then be used to detect and quantitate the FUSE binding protein.

EXAMPLE 7

The anti-sense sequence for the FUSE binding protein cDNA is useful therapeutically to arrest cell development in a target area of uncontrolled cell growth. An expression vector or oligonucleotide is constructed incorporating the anti-sense sequence of the FUSE binding protein cDNA. The oligonucleotide or vector is then incorporated into the cells of the target area, and acts to antagonize or block expression of the FUSE binding protein, inhibiting cell division and proliferation.

This is effective, for example, in arresting tumor cell growth, or an unwarranted immune response (i.e., arresting B- or T-lymphocytes).

The invention has been described in detail with particular reference to a preferred embodiment thereof, but it will be understood that the invention is capable of other and different embodiments. As is readily apparent to those skilled in the art, variations and modifications can be effected within the spirit and scope of the invention. Accordingly, the foregoing disclosure, description, and figures are for illustrative purposes only, and do not in any way limit the invention, which is defined only by the claims.

We claim:

1. A human cDNA that encodes a protein which binds specifically to an activator cis-element approximately 1500 basepairs 5' of the transcription start site of the human c-myc gene promoter P1, said cDNA comprised of the following sequence (SEQ ID NO: 1):

| | |
|---|---|
| GCGGCAGCGG CTCTTATAGT GCAACC ATG GCA 44 | AGT GTT CAG GCT GGT AAT CCT GGT GGA CCT 1097 |
| GAC TAT TCA ACA | GGA CCT GGT |
| GTG CCT CCC CCC TCT TCT GGC TCA GCT GGT 83 | GGT CGA GGA AGA GGT AGA GGT CAA GGC ACC 1136 |
| GGC GGT GGT | TGG AAC ATG |
| GGC GGC GGT GGT GGT GGA GGA GTT AAC GAC 122 | GGA CCA CCT GGT GGA TTA CAG GAA TTT AAT 1175 |
| GCT TTC AAA | TTT ATT GTG |
| GAT GCA CTG CAG AGA GCC CGG CAG ATT GCA 161 | CCA ACT GGG AAA ACT GGA TTA ATA ATA GGA 1214 |
| GCA AAA ATT | AAA GGA GGT |
| GGA GGT GAT GCA GGG ACA TCA CTG AAT TCA 200 | GAA ACC ATA AAA AGC ATA AGC CAG CAG TCT 1253 |
| AAT GAC TAT | GGT GCA AGA |
| GGT TAT GGG GGA CAA AAA AGA CCT TTA GAA 239 | ATA GAA CTT CAG AGA AAT CCT CCA CCA AAT 1292 |
| GAT GGA GAT | GCA GAT CCT |
| CAA CCA GAT GCT AAG AAA GTT GCT CCT CAA 278 | AAT ATG AAG TTA TTT ACA ATT CGT GGC ACT 1331 |
| AAT GAC TCT | CCA CAA CAG |
| TTT GGA ACA CAG TTA CCA CCG ATG CAT CAG 317 | ATA GAC TAT GCT CGG CAA CTC ATA GAA GAA 1370 |
| CAG CAA AGC | AAG ATT GGT |
| AGA TCT GTA ATG ACA GAA GAA TAC AAA GTT 356 | GGC CCA GTA AAT CCT TTA GGG CCA CCT GTA 1409 |
| CCA GAT GGA | CCC CAT GGG |
| ATG GTT GGA TTC ATA ATT GGC AGA GGA GGT 395 | CCC CAT GGT GTC CCA GGC CCC CAT GGA CCT 1448 |
| GAA CAG ATC | CCT GGG CCT |
| TCA CGC ATA CAA CAG GAA TCT GGA TGC AAA 434 | CCA GGG CCT GGA ACT CCA ATG GGA CCA TAC 1487 |
| ATA CAG ATA | AAC CCT GCA |
| GCT CCT GAC AGT GGT GGC CTT CCA GAA AGG 473 | CCT TAT AAT CCT GGA CCA CCA GGC CCG GCT 1526 |
| TCC TGT ATR | CCT CAT GGT |
| TTA ACT GGA ACA CCT GAA TCT GTC CAG TCA 512 | CCT CCA GCC CCA TAT GCT CCC CAG GGA TGG 1565 |
| GCA AAA CGG | GGA AAT GCA |
| TTA CTG GAC CAG ATT GTT GAA AAA GGA AGA 551 | TAT CCA CAC TGG CAG CAG CAG GCT CCT CCT 1604 |
| CCA GCT CCT | GAT CCA GCT |
| GGC TTC CAT CAT GGC GAT GGA CCG GGA AAT 590 | AAG GCA GGA ACG GAT CCA AAT TCA GCA GCT 1643 |
| GCA GTT CAA | TGG GCT GCT |
| GAA ATC ATG ATT CCA GCT AGC AAG GCA GGA 629 | TAT TAC GCT CAC TAT TAT CAA CAG CAA GCA 1682 |
| TTA GTC ATT | CAG CCA CCA |
| GGA AAA GGG GGA GAA ACT ATT AAA CAG CTT 668 | CCA GCA GCC CCT GCA GGT GCA CCA ACT ACA 1721 |
| CAG GAA CGG | ACT CAA ACT |
| GCT GGA GTT AAA ATG GTT ATG ATT CAA GAC 707 | AAT GGA CAA GGA GAT CAG CAG AAT CCA GCC 1760 |
| GGG CCG CAG | CCA GCT GGA |
| AAC ACT GGT GCT GAC AAA CCT CTT AGG ATT 746 | CAG GTT GAT TAT ACC AAG GCT TGG GAA GAG 1799 |
| ACA GGA GAC | TAC TAC AAG |
| CCA TAT AAA GTT CAA CAA GCC AAG GAA ATG 785 | AAA ATG GGT CAG GCA GTT CCT GCT CCG ACT 1838 |
| GTG TTA GAG | GGG GCT CCT |
| TTA ATT CGT GAT CAA GGC GGT TTC AGA GAA 824 | CCA GGT GGT CAG CCA GAT TAT AGT GCA GCC 1877 |
| GTT CGG AAT | TGG GCT GAG |
| GAG TAT GGG TCA AGA ATA GGA GGA AAT GAA 863 | CAT TAT AGA CAA CAA GCA GCC TAT TAT GCC 1916 |
| GGG ATA GAT | CAG ACA AGT |
| GTC CCC ATT CCA AGA TTT GCT GTT GGC ATT 902 | CCC CAG GGA ATG CCA CAG CAT CCT CCA GCA 1955 |
| GTA ATA GGA | CCT CAG GGC |
| ATA AAT GGA GAG ATG ATC AAA AAA ATA CAA 941 | CAA TAA TAA GAAGTGGACA ATACAGTATT 1994 |
| AAT GAT GCT | TGCTTCATTG |
| GGT GTT CGC ATT CAG TTT AAG CCA GAT GAT 980 | TGTGGGGGAA AAAAACCTTT GTTAAATATA 2034 |
| GGG ACA ACA | TGGATGCAGA |
| CCC GAA AGG ATA GCA CAA ATA ACA GGA CCT 1019 | CGACTTGATG AAGATCTTAA TTTTGTTTTT 2074 |
| CCA GAC CGA | GGTTTAAAAT |
| TGT CAA CAT GCT GCA GAA ATT ATT ACA GAC 1058 | AGTGTTTCCT TTTTTTTTTT TTTTTTTTG 2114 |
| CTT CTT CGA | |

| | | | | | | | | | | |
|---|---|---|---|---|---|---|---|---|---|---|
| AAATATCTAT | CACTACTGAT | AGGAGGTTAA | | | AAAATGTACA | | | | | 2154 |
| | | | | | TATTTCTGTG | | | | | |
| TAGAAATGAA | AATTGGTTTG | TTTTTAGTAT | | | | | | | | 2194 |
| | | | | | TTAGTGTAGA | | | | | |
| TGTACACATT | CCAGCAAATG | TATTTGCAAT | | | | | | | | 2234 |
| | | | | | TATGTGGTTG | | | | | |
| ATGCTTTGTG | ATATAAATGT | ACTTTTTCAA | | | | | | | | 2274 |
| | | | | | TGTATACTTT | | | | | |
| CACTTTCCAA | ATGCCTGTTT | TGTGCTTTAC | | | | | | | | 2314 |
| | | | | | AATAAATGAT | | | | | |
| ATGAAACCTC | AAAAAAAAAA | AAAAAAAAAA | | | | | | | | 2354 |

| | | |
|---|---|---|
| | AAAAAAAAAA | |
| AAAAAAAAAA AAAAAAAAAA AAAAAAAAAA | | 2384 | wherein R is A or G.

2. The cDNA sequence of claim 1, wherein R is G.

3. The cDNA sequence of claim 1, wherein R is A.

4. A cDNA comprised of the anti-sense sequence of SEQ ID NO:1.

5. A human cDNA that encodes a protein which binds specifically to an activator cis-element approximately 1500 basepairs 5' of the transcription start site of the human c-myc gene promoter P1, said cDNA comprised of the following sequence (SEQ ID NO: 9):

| | | | | | | | | | | | |
|---|---|---|---|---|---|---|---|---|---|---|---|
| GCGGCAGCGG | | CTCTTATAGT | | GCAACC | ATG | GCA | GAC | TAT | TCA | ACA | 44 |
| GTG | CCT | CCC | CCC | TCT | TCT | GGC | TCA | GCT | GGT | GGC | GGT | GGT | 83 |
| GGC | GGC | GGT | GGT | GGT | GGA | GGA | GTT | AAC | GAC | GCT | TTC | AAA | 122 |
| GAT | GCA | CTG | CAG | AGA | GCC | CGG | CAG | ATT | GCA | GCA | AAA | ATT | 161 |
| GGA | GGT | GAT | GCA | GGG | ACA | TCA | CTG | AAT | TCA | AAT | GAC | TAT | 200 |
| GGT | TAT | GGG | GGA | CAA | AAA | AGA | CCT | TTA | GAA | GAT | GGA | GAT | 239 |
| CAA | CCA | GAT | GCT | AAG | AAA | GTT | GCT | CCT | CAA | AAT | GAC | TCT | 278 |
| TTT | GGA | ACA | CAG | TTA | CCA | CCG | ATG | CAT | CAG | CAG | CAA | | 314 |
| AGA | TCT | GTA | ATG | ACA | GAA | GAA | TAC | AAA | GTT | CCA | GAT | GGA | 353 |
| ATG | GTT | GGA | TTC | ATA | ATT | GGC | AGA | GGA | GGT | GAA | CAG | ATC | 392 |
| TCA | CGC | ATA | CAA | CAG | GAA | TCT | GGA | TGC | AAA | ATA | CAG | ATA | 431 |
| GCT | CCT | GAC | AGT | GGT | GGC | CTT | CCA | GAA | AGG | TCC | TGT | ATR | 470 |
| TTA | ACT | GGA | ACA | CCT | GAA | TCT | GTC | CAG | TCA | GCA | AAA | CGG | 509 |
| TTA | CTG | GAC | CAG | ATT | GTT | GAA | AAA | GGA | AGA | CCA | GCT | CCT | 548 |
| GGC | TTC | CAT | CAT | GGC | GAT | GGA | CCG | GGA | AAT | GCA | GTT | CAA | 587 |
| GAA | ATC | ATG | ATT | CCA | GCT | AGC | AAG | GCA | GGA | TTA | GTC | ATT | 626 |
| GGA | AAA | GGG | GGA | GAA | ACT | ATT | AAA | CAG | CTT | CAG | GAA | CGG | 665 |
| GCT | GGA | GTT | AAA | ATG | GTT | ATG | ATT | CAA | GAC | GGG | CCG | CAG | 704 |
| AAC | ACT | GGT | GCT | GAC | AAA | CCT | CTT | AGG | ATT | ACA | GGA | GAC | 743 |
| CCA | TAT | AAA | GTT | CAA | CAA | GCC | AAG | GAA | ATG | GTG | TTA | GAG | 782 |
| TTA | ATT | CGT | GAT | CAA | GGC | GGT | TTC | AGA | GAA | GTT | CGG | AAT | 821 |
| GAG | TAT | GGG | TCA | AGA | ATA | GGA | GGA | AAT | GAA | GGG | ATA | GAT | 860 |
| GTC | CCC | ATT | CCA | AGA | TTT | GCT | GTT | GGC | ATT | GTA | ATA | GGA | 899 |
| AGA | AAT | GGA | GAG | ATG | ATC | AAA | AAA | ATA | CAA | AAT | GAT | GCT | 938 |
| GGT | GTT | CGC | ATT | CAG | TTT | AAG | CCA | GAT | GAT | GGG | ACA | ACA | 977 |
| CCC | GAA | AGG | ATA | GCA | CAA | ATA | ACA | GGA | CCT | CCA | GAC | CGA | 1016 |
| TGT | CAA | CAT | GCT | GCA | GAA | ATT | ATT | ACA | GAC | CTT | CTT | CGA | 1055 |
| AGT | GTT | CAG | GCT | GGT | AAT | CCT | GGT | GGA | CCT | GGA | CCT | GGT | 1094 |
| GGT | CGA | GGA | AGA | GGT | AGA | GGT | CAA | GGC | AAC | TGG | AAC | ATG | 1133 |

-continued

| | | | | | | | | | | | | |
|---|---|---|---|---|---|---|---|---|---|---|---|---|
| GGA | CCA | CCT | GGT | GGA | TTA | CAG | GAA | TTT | AAT | TTT | ATT | GTG | 1172 |
| CCA | ACT | GGG | AAA | ACT | GGA | TTA | ATA | ATA | GGA | AAA | GGA | GGT | 1211 |
| GAA | ACC | ATA | AAA | AGC | ATA | AGC | CAG | CAG | TCT | GGT | GCA | AGA | 1250 |
| ATA | GAA | CTT | CAG | AGA | AAT | CCT | CCA | CCA | AAT | GCA | GAT | CCT | 1289 |
| AAT | ATG | AAG | TTA | TTT | ACA | ATT | CGT | GGC | ACT | CCA | CAA | CAG | 1328 |
| ATA | GAC | TAT | GCT | CGG | CAA | CTC | ATA | GAA | GAA | AAG | ATT | GGT | 1367 |
| GGC | CCA | GTA | AAT | CCT | TTA | GGG | CCA | CCT | GTA | CCC | CAT | GGG | 1406 |
| CCC | CAT | GGT | GTC | CCA | GGC | CCC | CAT | GGA | CCT | CCT | GGG | CCT | 1445 |
| CCA | GGG | CCT | GGA | ACT | CCA | ATG | GGA | CCA | TAC | AAC | CCT | GCA | 1484 |
| CCT | TAT | AAT | CCT | GGA | CCA | CCA | GGC | CCG | GCT | CCT | CAT | GGT | 1523 |
| CCT | CCA | GCC | CCA | TAT | GCT | CCC | CAG | GGA | TGG | GGA | AAT | GCA | 1562 |
| TAT | CCA | CAC | TGG | CAG | CAG | CAG | GCT | CCT | CCT | GAT | CCA | GCT | 1601 |
| AAG | GCA | GGA | ACG | GAT | CCA | AAT | TCA | GCA | GCT | TGG | GCT | GCT | 1640 |
| TAT | TAC | GCT | CAC | TAT | TAT | CAA | CAG | CAA | GCA | CAG | CCA | CCA | 1679 |
| CCA | GCA | GCC | CCT | GCA | GGT | GCA | CCA | ACT | ACA | ACT | CAA | ACT | 1718 |
| AAT | GGA | CAA | GGA | GAT | CAG | CAG | AAT | CCA | GCC | CCA | GCT | GGA | 1757 |
| CAG | GTT | GAT | TAT | ACC | AAG | GCT | TGG | GAA | GAG | TAC | TAC | AAG | 1796 |
| AAA | ATG | GGT | CAG | GCA | GTT | CCT | GCT | CCG | ACT | GGG | GCT | CCT | 1835 |
| CCA | GGT | GGT | CAG | CCA | GAT | TAT | AGT | GCA | GCC | TGG | GCT | GAG | 1874 |
| CAT | TAT | AGA | CAA | CAA | GCA | GCC | TAT | TAT | GCC | CAG | ACA | AGT | 1913 |
| CCC | CAG | GGA | ATG | CCA | CAG | CAT | CCT | CCA | GCA | CCT | CAG | GGC | 1952 |
| CAA | TAA | TAA | GAAGTGGACA | ATACAGTATT | TGCTTCATTG | | | | | | | | 1991 |
| TGTGGGGGAA | AAAAACCTTT | GTTAAATATA | TGGATGCAGA | | | | | | | | | | 2031 |
| CGACTTGATG | AAGATCTTAA | TTTTGTTTTT | GGTTTAAAAT | | | | | | | | | | 2071 |
| AGTGTTTCCT | TTTTTTTTTT | TTTTTTTTTG | AAAATGTACA | | | | | | | | | | 2111 |
| AAATATCTAT | CACTACTGAT | AGGAGGTTAA | TATTTCTGTG | | | | | | | | | | 2151 |
| TAGAAATGAA | AATTGGTTTG | TTTTTAGTAT | TTAGTGTAGA | | | | | | | | | | 2191 |
| TGTACACATT | CCAGCAAATG | TATTTGCAAT | TATGTGGTTG | | | | | | | | | | 2231 |
| ATGCTTTGTG | ATATAAATGT | ACTTTTTCAA | TGTATACTTT | | | | | | | | | | 2271 |
| CACTTTCCAA | ATGCCTGTTT | TGTGCTTTAC | AATAAATGAT | | | | | | | | | | 2311 |
| ATGAAACCTC | AAAAAAAAAA | AAAAAAAAAA | AAAAAAAAAA | | | | | | | | | | 2351 |
| AAAAAAAAAA | AAAAAAAAAA | AAAAAAAAAA | 2381 | | | | | | | | | | | wherein R is A or G.

6. The cDNA sequence of claim 5, wherein R is G.
7. The cDNA sequence of claim 5, wherein R is A.
8. A cDNA comprised of the anti-sense sequence of SEQ ID NO:9.

9. A human cDNA that encodes a protein which binds specifically to an activator cis-element approximately 1500 basepairs 5' of the transcription start site of the human c-myc gene promoter P1, said cDNA comprised of the following sequence (SEQ ID NO: 5):

| | | | | | | | | | | | |
|---|---|---|---|---|---|---|---|---|---|---|---|
| GGAATTCCGG | ATA | GAT | GTC | CCC | ATT | CCA | AGA | TTT | GCT | GTT | 40 |
| GGC | ATT | GTA | ATA | GGA | AGA | AAT | GGA | GAG | ATG | ATC | AAA | AAA | 79 |
| ATA | CAA | AAT | GAT | GCT | GGT | GTT | CGC | ATT | CAG | TTT | AAG | CCA | 118 |

| | | | | | | | | | | | | |
|---|---|---|---|---|---|---|---|---|---|---|---|---|
| GAT | GAT | GGG | ACA | ACA | CCC | GAA | AGG | ATA | GCA | CAA | ATA | ACA | 157 |
| GGA | CCT | CCA | GAC | CGA | TGT | CAA | CAT | GCT | GCA | GAA | ATT | ATT | 196 |
| ACA | GAC | CTT | CTT | CGA | AGT | GTT | CAG | GCT | GGT | AAT | CCT | GGT | 235 |
| GGA | CCT | GGA | CCT | GGT | GGT | CGA | GGA | AGA | GGT | AGA | GGT | CAA | 274 |
| GGC | AAC | TGG | AAC | ATG | GGA | CCA | CCT | GGT | GGA | TTA | CAG | GAA | 313 |
| TTT | AAT | TTT | ATT | GTG | CCA | ACT | GGG | AAA | ACT | GGA | TTA | ATA | 352 |
| ATA | GGA | AAA | GGA | GGT | GAA | ACC | ATA | AAA | AGC | ATA | AGC | CAG | 391 |
| CAG | TCT | GGT | GCA | AGA | ATA | GAA | CTT | CAG | AGA | AAT | CCT | CCA | 430 |
| CCA | AAT | GCA | GAT | CCT | AAT | ATG | AAG | TTA | TTT | ACA | ATT | CGT | 469 |
| GGC | ACT | CCA | CAA | CAG | ATA | GAC | TAT | GCT | CGG | CAA | CTC | ATA | 508 |
| GAA | GAA | AAG | ATT | GGT | GGC | CCA | GTA | AAT | CCT | TTA | GGG | CCA | 547 |
| CCT | GTA | CCC | CAT | GGG | CCC | CAT | GGT | GTC | CCA | GGC | CCC | CAT | 586 |
| GGA | CCT | CCT | GGG | CCT | CCA | GGG | CCT | GGA | ACT | CCA | ATG | GGA | 625 |
| CCA | TAC | AAC | CCT | GCA | CCT | TAT | AAT | CCT | GGA | CCA | CCA | GGC | 664 |
| CCG | GCT | CCT | CAT | GGT | CCT | CCA | GCC | CCA | TAT | GCT | CCC | CAG | 703 |
| GGA | TGG | GGA | AAG | GAA | ATT | GAG | CAG | AAG | GTA | CAG | GAG | TAA | 742 |
| TAG | CAATTCCCTG | | TAGCTCTCAA | | AGCAAATTTT | | GAGCTCATTT | | | | | | 785 |
| TTCTTTTTCT | | GCAAGCTCAG | | CAGCAGAATG | | CCCAGAGTCT | | | | | | | 825 |
| TCCCTGGTAG | | ATGCAGGTTC | | CATAGCGACG | | TTCTCCTGCA | | | | | | | 865 |
| ATGCACGCTG | | GTATTCTGCA | | ATAGCAGGCC | | ATGTTTTCCT | | | | | | | 905 |
| TGAGCCTGGA | | TGCTTTGGAG | | CCAAGCTTTC | | GTCCCATGCA | | | | | | | 945 |
| AGGGAAACAA | | CCACTTCTGG | | GATGTCCGCT | | GCAATCTGCT | | | | | | | 985 |
| CCGGGGCTGC | | AGCAACCTCA | | TCAGCTCTCT | | TGCCTGGAGT | | | | | | | 1025 |
| GGCTCAGCCT | | GGCCTGCAGG | | GCCACCAGGA | | GAATGGCAGC | | | | | | | 1065 |
| AAGGATGGCG | | AGGGTCCTCA | | TGGCTGGAAT | | TC | | | | | | | 1097. |

10. A cDNA comprised of the anti-sense sequence of SEQ ID NO: 5.

11. A human cDNA that encodes a protein which binds specifically to an activator cis-element approximately 1500 basepairs 5' of the transcription start site of the human c-myc gene promoter P1, comprised of the following sequence (SEQ ID NO: 7):

| | | | | | | | | | | | | |
|---|---|---|---|---|---|---|---|---|---|---|---|---|
| GAATTCCGGA | | CGACAGCGGC | | TCTG | AGA | GCC | CGG | CAG | ATT | GCA | | 42 |
| GCA | AAA | ATT | GGA | GGT | GAT | GCA | GGG | ACA | TCA | CTG | AAT | TCA | 81 |
| AAT | GAC | TAT | GGT | TAT | GGG | GGA | CAA | AAA | AGA | CCT | TTA | GAA | 120 |
| GAT | GGA | GAT | GGC | TCT | TGG | ACA | AGT | CCG | AGC | AGT | ACA | ACA | 159 |
| CAC | TGG | GAG | GGA | ATG | CCC | TCT | CCT | TTT | AAA | GAT | CAA | CCA | 198 |
| GAT | GCT | AAG | AAA | GTT | GCT | CCT | CAA | AAT | GAC | TCT | TTT | GGA | 237 |
| ACA | CAG | TTA | CCA | CCG | ATG | CAT | CAG | CAG | CAA | AGA | TCT | GTA | 276 |
| ATG | ACA | GAA | GAA | TAC | AAA | GTT | CCA | GAT | GGA | ATG | GTT | GGA | 315 |
| TTC | ATA | ATT | GGC | AGA | GGA | GGT | GAA | CAG | ATC | TCA | CGC | ATA | 354 |
| CAA | CAG | GAA | TCT | GGA | TGC | AAA | ATA | CAG | ATA | GCT | CCT | GAC | 393 |

| | | | | | | | | | | | | |
|---|---|---|---|---|---|---|---|---|---|---|---|---|
| AGT | GGT | GGC | CTT | CCA | GAA | AGG | TCC | TGT | ATG | TTA | ACT | GGA | 432 |
| ACA | CCT | GAA | TCT | GTC | CAG | TCA | GCA | AAA | CGG | TTA | CTG | GAC | 471 |
| CAG | ATT | GTT | GAA | AAA | GGA | AGA | CCA | GCT | CCT | GGC | TTC | CAT | 510 |
| CAT | GGC | GAT | GGA | CCG | GGA | AAT | GCA | GTT | CAA | GAA | ATC | ATG | 549 |
| ATT | CCA | GCT | AGC | AAG | GCA | GGA | TTA | GTC | ATT | GGA | AAA | GGG | 588 |
| GGA | GAA | ACT | ATT | AAA | CAG | CTT | CAG | GAA | CGG | GCT | GGA | GTT | 627 |
| AAA | ATG | GTT | ATG | ATT | CAA | GAC | GGG | CCG | CAG | AAC | ACT | GGT | 666 |
| GCT | GAC | AAA | CCT | CTT | AGG | ATT | ACA | GGA | GAC | CCA | TAT | AAA | 705 |
| GTT | CAA | CAA | GCC | AAG | GAA | ATG | GTG | TTA | GAG | TTA | ATT | CGT | 744 |
| GAT | CAA | GGC | GGT | TTC | AGA | GAA | GTT | CGG | AAT | GAG | TAT | GGG | 783 |
| TCA | AGA | ATA | GGA | GGA | AAT | GAA | GGG | ATA | GAT | GTC | CCC | ATT | 822 |
| CCA | AGA | TTT | GCT | GTT | GGC | ATT | GTA | ATA | GGA | AGA | AAT | GGA | 861 |
| GAG | ATG | ATC | AAA | AAA | ATA | CAA | AAT | GAT | GCT | GGT | GTT | CGC | 900 |
| ATT | CAG | TTT | AAG | CCA | GAT | GAT | GGG | ACA | ACA | CCC | GAA | AGG | 939 |
| ATA | GCA | CAA | ATA | ACA | GGA | CCT | CCA | GAC | CGA | TGT | CAA | CAT | 978 |
| GCT | GCA | GAA | ATT | ATT | ACA | GAC | CTT | CTT | CGA | AGT | GTT | CAG | 1017 |
| GCT | GGT | AAT | CCT | GGT | GGA | CCT | GGA | CCT | GGT | GGT | CGA | GGA | 1056 |
| AGA | GGT | AGA | GGT | CAA | GGC | AAC | TGG | AAC | ATG | GGA | CCA | CCT | 1095 |
| GGT | GGA | TTA | CAG | GAA | TTT | AAT | TTT | ATT | GTG | CCA | ACT | GGG | 1134 |
| AAA | ACT | GGA | TTA | ATA | ATA | GGA | AAA | GGA | GGT | GAA | ACC | ATA | 1173 |
| AAA | AGC | ATA | AGC | CAG | CAG | TCT | GGT | GCA | AGA | ATA | GAA | CTT | 1212 |
| CAG | AGA | AAT | CCT | CCA | CCA | AAT | GCA | GAT | CCT | AAT | ATG | AAG | 1251 |
| TTA | TTT | ACA | ATT | CGT | GGC | ACT | CCA | CAA | CAG | ATA | GAC | TAT | 1290 |
| GCT | CGG | CAA | CTC | ATA | GAA | GAA | AAG | ATT | GGT | GGC | CCA | GTA | 1329 |
| AAT | CCT | TTA | GGG | CCA | CCT | GTA | CCC | CAT | GGG | CCC | CAT | GGT | 1368 |
| GTC | CCA | GGC | CCC | CAT | GGA | CCT | CCT | GGG | CCT | CCA | GGG | CCT | 1407 |
| GGA | ACT | CCA | ATG | GGA | CCA | TAC | AAC | CCT | GCA | CCT | TAT | AAT | 1446 |
| CCT | GGA | CCA | CCA | GGC | CCG | GCT | CCT | CAT | GGT | CCT | CCA | GCC | 1485 |
| CCA | TAT | GCT | CCC | CAG | GGA | TGG | GGA | AAT | GCA | TAT | CCA | CAC | 1524 |
| TGG | CAG | CAG | CAG | GCT | CCT | CCT | GAT | CCA | GCT | AAG | GCA | GGA | 1563 |
| ACG | GAT | CCA | AAT | TCA | GCA | GCT | TGG | GCT | GCT | TAT | TAC | GCT | 1602 |
| CAC | TAT | TAT | CAA | CAG | CAA | GCA | CAG | CCA | CCA | CCA | GCA | GCC | 1641 |
| CCT | GCA | GGT | GCA | CCA | ACT | ACA | ACT | CAA | ACT | AAT | GGA | CAA | 1680 |
| GGA | GAT | CAG | CAG | AAT | CCA | GCC | CCA | GCT | GGA | CAG | GTT | GAT | 1719 |
| TAT | ACC | AAG | GCT | TGG | GAA | GAG | TAC | TAC | AAG | AAA | ATG | GGG | 1758 |
| CCA | ATA | ATA | AGA | AGT | GGA | CAA | TAC | AGT | ATT | TGC | TTC | | 1794 |
| AGGAATTCC | | | | | | | | | | | | | 1803. |

12. A cDNA comprised of the anti-sense sequence of SEQ ID NO:7.

13. A method of producing a human cDNA that codes for a protein which binds specifically to an activator cis-element approximately 1500 basepairs 5' of the transcription start site of the human c-myc gene promoter P1, comprising the steps of providing a set of oligonucleotide primers comprising (SEQ ID NO:3 and SEQ ID NO:4):

5'-CAGAATTCGGIGGIAAYGARGGIANCG-3'

5'-GAGTCGACRTCRTCRTCIGGYTTRAA-3, wherein I indicates an inosine residue, and Y is either T or C, R is either A or G, and N is either I or T, applying said primers in a polymerase chain reaction employing human cDNA as a template to produce target products corresponding to said primers, cloning said target products, and constructing a full length reading frame from overlapping target products.

14. A primer having the sequence of SEQ ID NO: 3.

15. A primer having the sequence of SEQ ID NO: 4.

16. A biologically functional circular plasmid or viral DNA vector including a cDNA sequence according to claim 1, 2, 3, 4, 5, 6, 7, 8, 9, 10, 11 or 12.

17. A prokaryotic or eukaryotic host cell transformed or transfected with a DNA vector according to claim 16.

18. A transformed or transfected human HL60 cell according to claim 17.

19. A kit for detecting mRNA encoding FUSE binding protein including at least one of the cDNA sequences, or fragments comprising at least 26 nucleotides thereof, shown in SEQ ID NO: 1, SEQ ID NO: 3, SEQ ID NO: 4, SEQ ID NO: 5, SEQ ID NO: 7, or SEQ ID NO: 9.

20. A fragment of the cDNA of claim 1 encoding at least two intact fuse binding protein repeat-helix units.

21. A fragment of the cDNA of claim 1 comprising at least 26 nucleotides.

22. A fragment of the cDNA of claim 4 comprising at least 26 nucleotides.

23. A fragment of the cDNA of claim 5 encoding at least two intact fuse binding protein repeat-helix units.

24. A fragment of the cDNA of claim 5 comprising at least 26 nucleotides.

25. A fragment of the cDNA of claim 8 comprising at least 26 nucleotides.

26. A fragment of the cDNA of claim 9 encoding at least two intact fuse binding protein repeat-helix units.

27. A fragment of the cDNA of claim 9 comprising at least 26 nucleotides.

28. A fragment of the cDNA of claim 10 comprising at least 26 nucleotides.

29. A fragment of the cDNA of claim 11 encoding at least two intact fuse binding protein repeat-helix units.

30. A fragment of the cDNA of claim 11 comprising at least 26 nucleotides.

31. A fragment of the cDNA of claim 12 comprising at least 26 nucleotides.

32. A vector comprising the cDNA of claim 1.
33. A vector comprising the cDNA of claim 4.
34. A vector comprising the cDNA of claim 8.
35. A vector comprising the cDNA of claim 9.
36. A vector comprising the cDNA of claim 10.
37. A vector comprising the cDNA of claim 11.
38. A vector comprising the cDNA of claim 12.
39. A vector comprising the fragment of claim 20.
40. A vector comprising the fragment of claim 21.
41. A vector comprising the fragment of claim 22.
42. A vector comprising the fragment of claim 23.
43. A vector comprising the fragment of claim 24.
44. A vector comprising the fragment of claim 25.
45. A vector comprising the fragment of claim 26.
46. A vector comprising the fragment of claim 27.
47. A vector comprising the fragment of claim 28.
48. A vector comprising the fragment of claim 29.
49. A vector comprising the fragment of claim 30.
50. A vector comprising the fragment of claim 31.

* * * * *